United States Patent
Derenne et al.

(10) Patent No.: US 10,121,070 B2
(45) Date of Patent: Nov. 6, 2018

(54) VIDEO MONITORING SYSTEM

(71) Applicant: Stryker Corporation, Kalamazoo, MI (US)

(72) Inventors: Richard A. Derenne, Portage, MI (US); Richard Thomas DeLuca, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 15/808,465

(22) Filed: Nov. 9, 2017

(65) Prior Publication Data

US 2018/0068179 A1 Mar. 8, 2018

Related U.S. Application Data

(63) Continuation of application No. 14/578,630, filed on Dec. 22, 2014, which is a continuation-in-part of (Continued)

(51) Int. Cl.
*G06K 9/00* (2006.01)
*A61B 5/00* (2006.01)
(Continued)

(52) U.S. Cl.
CPC .......... *G06K 9/00369* (2013.01); *A61B 5/002* (2013.01); *A61B 5/0013* (2013.01);
(Continued)

(58) Field of Classification Search
None
See application file for complete search history.

(56) References Cited

U.S. PATENT DOCUMENTS 5,425,148 A 6/1995 Ashcraft et al.
5,699,038 A * 12/1997 Ulrich .................... A61G 12/00
340/286.06
(Continued)

FOREIGN PATENT DOCUMENTS

WO 2015070416 A1 5/2015

OTHER PUBLICATIONS

Fall Risk Assessment for Older Adults: The Hendrich II Fall Risk Model, by Deanna Gray-Miceli, DNSc, APRN, BC, FAANP, University of Pennsylvania; from the Hartford Institute for Geriatric Nursing, New York University, College of Nursing, Issue No. 8, Revised 2007.

(Continued)

*Primary Examiner* — Peter D Le
(74) *Attorney, Agent, or Firm* — Warner Norcross + Judd LLP

(57) ABSTRACT

A monitoring system includes cameras adapted to capture images and depth data of the images. A computer device processes the image signals and depth data from the cameras according to various software modules that monitor one or more of the following: (a) compliance with patient care protocols; (b) patient activity; (c) equipment usage; (d) the location and/or usage of assets; (e) patient visitation metrics; (f) data from other sensors that is integrated with the image and depth data; (g) gestures by the patient or caregivers that are used as signals or for controls of equipment, and other items. Alerts may be issued if any conditions of importance are detected.

19 Claims, 17 Drawing Sheets

Related U.S. Application Data application No. 13/242,022, filed on Sep. 23, 2011, now Pat. No. 9,204,823.

(60) Provisional application No. 61/385,607, filed on Sep. 23, 2010.

(51) Int. Cl.

| | | |
|---|---|---|
| *A61B 5/11* | (2006.01) | |
| *G08B 21/04* | (2006.01) | |
| *H04N 7/18* | (2006.01) | |
| *G06F 17/30* | (2006.01) | |
| *G06F 19/00* | (2018.01) | |
| *G08B 21/24* | (2006.01) | |
| *G16H 50/30* | (2018.01) | |
| *G16H 80/00* | (2018.01) | |

(52) U.S. Cl.
CPC ........... *A61B 5/1113* (2013.01); *A61B 5/1128* (2013.01); *A61B 5/7445* (2013.01); *G06F 17/30817* (2013.01); *G06F 19/00* (2013.01); *G06F 19/3418* (2013.01); *G08B 21/043* (2013.01); *G08B 21/0476* (2013.01); *G08B 21/245* (2013.01); *G16H 50/30* (2018.01); *G16H 80/00* (2018.01); *H04N 7/185* (2013.01); *A61B 5/1115* (2013.01); *A61B 5/1117* (2013.01); *A61B 5/1123* (2013.01); *A61B 5/6889* (2013.01); *A61B 5/6892* (2013.01); *A61B 5/7475* (2013.01)

(56) References Cited

U.S. PATENT DOCUMENTS

| | | | |
|---|---|---|---|
| 6,049,281 A | | 4/2000 | Osterweil |
| 8,620,625 B2 | | 12/2013 | Sing et al. |
| 8,727,981 B2 | | 5/2014 | Bechtel et al. |
| 9,123,229 B2 | | 9/2015 | Slavin et al. |
| 9,295,390 B2 | | 3/2016 | Receveur et al. |
| 2005/0084179 A1 | | 4/2005 | Hanna et al. |
| 2006/0049936 A1 | * | 3/2006 | Collins, Jr. ............ A61B 5/1115 340/539.11 |
| 2008/0021731 A1 | | 1/2008 | Rodgers |
| 2008/0172789 A1 | * | 7/2008 | Elliot ................... A61G 7/0528 5/616 |
| 2009/0119843 A1 | | 5/2009 | Rodgers et al. |
| 2009/0216775 A1 | | 8/2009 | Ratliff et al. |
| 2009/0259113 A1 | | 10/2009 | Liu et al. |
| 2009/0278934 A1 | | 11/2009 | Ecker et al. |
| 2010/0328443 A1 | | 12/2010 | Lynam et al. |
| 2011/0025817 A1 | * | 2/2011 | Carter ................... A61B 5/1112 348/14.02 |
| 2011/0153361 A1 | * | 6/2011 | Hanina ................. G06Q 10/10 705/3 |
| 2011/0208541 A1 | * | 8/2011 | Wilson ................. A61B 7/018 705/3 |
| 2012/0025990 A1 | * | 2/2012 | Tallent ............... G08B 21/0461 340/573.4 |
| 2012/0026308 A1 | * | 2/2012 | Johnson ............ G06K 9/00369 348/77 |
| 2012/0075464 A1 | | 3/2012 | Derenne et al. |
| 2014/0092247 A1 | | 4/2014 | Clark et al. |
| 2014/0342330 A1 | | 11/2014 | Freeman et al. |
| 2015/0268739 A1 | | 9/2015 | Sanaullah et al. |

OTHER PUBLICATIONS

Morse Fall Scale, Sage Publications, a document believed to be publicly available prior to Dec. 22, 2013.

\* cited by examiner

VIDEO MONITORING SYSTEM

CROSS-REFERENCE TO RELATED APPLICATIONS

This application is a continuation of U.S. patent application Ser. No. 14/578,630 filed Dec. 22, 2014, by inventors Richard Derenne et al. and entitled VIDEO MONITORING SYSTEM, which in turn is a continuation-in-part of U.S. patent application Ser. No. 13/242,022 filed Sep. 23, 2011 by inventors Richard A. Derenne et al. and entitled VIDEO MONITORING SYSTEM, which claims the benefit of U.S. provisional patent application Ser. No. 61/385,607, filed Sep. 23, 2010, by applicants Richard A. Derenne et al. and entitled VIDEO MONITORING SYSTEM, the complete disclosures of all of which are incorporated by reference herein in their entirety.

BACKGROUND

The present invention relates to systems and methods utilizing video cameras for monitoring patients, caregivers, equipment, and other items within a room in a caregiver setting, such as a hospital, nursing home, treatment center, or the like.

SUMMARY

According to various aspects of the systems and methods of the present invention, improved patient care is accomplished through the use of one or more video cameras positioned within a patient's room in order to provide patient care assistance in one or more of a variety of different manners. Such patient care assistance results from the analysis of video camera images that are used for any one or more of the following purposes: preventing patient falls, reducing the chances and/or spread of infection, ensuring patient care protocols are properly executed, and/or monitoring patient activity. Such analysis takes place using one or more computer devices programmed to process and analyze video images. The computer devices are either positioned inside the room of the patient, or located remotely.

According to one embodiment, a monitoring system is provided that includes a camera, a database, and a computer device. The camera is adapted to capture images of at least a portion of a person support apparatus and output image data representative of the images. The database contains fall prevention protocol data that defines one or more conditions that are to be met prior to an occupant exiting the person support apparatus in order to reduce a fall risk of the occupant. The computer device communicates with the camera and the database, and the computer device is adapted to analyze the image data to determine if the one or more conditions have been met.

In some embodiments, the system also includes a user interface in communication with the database. The user interface allows an authorized user to enter information into the database defining the one or more conditions.

In at least one embodiment, the user interface allows a caregiver to enter a fall risk assessment of the occupant into the database, and the computer device determines if the one or more conditions have been met only if the fall risk assessment is present in the database and meets a threshold. If the fall risk assessment of the occupant is not present in the database, the computer device automatically determines if the one or more conditions have been met. The computer device communicates with an electronic medical records system, in some embodiments, and alters the fall risk assessment if the occupant has recently been administered a drug that increases his or her fall risk, such as, but not limited to, any anti-epileptic drugs or benzodiazepines.

The fall risk assessment comprises a numeric scale, in some embodiments, that is generated from scores associated with a plurality of fall risk factors, and the computer device uses the image data to generate a score for at least one of the fall risk factors. The computer device is further adapted, in at least some embodiments, to compare the score generated by the computer device to a corresponding score entered by the caregiver as part of the risk assessment. If the score generated by the computer device differs from the score entered by the caregiver, the computer device issues an alert.

In some embodiments, at least one of the fall risk factors is an IV/Heparin lock factor, and the computer device scores the IV/Heparin lock factor with a first value if an IV/Heparin lock is being used with the occupant, and the computer device scores the IV/Heparin lock factor with a second value if no IV/Heparin lock is being used with the occupant.

In some embodiments, at least one of the fall risk factors is a gait of the occupant, and the computer devices scores the gait factor with a first value if the occupant has a weak gait, and the computer device scores the gait factor with a second value if the occupant has a normal gait. The computer device determines if the occupant has a weak gait, in at least one embodiment, by analyzing the image data to determine at least two of the following factors: if the occupant walks with his or her head up, if the occupant walks with his or her arms swinging freely, if the occupant shuffles his or her feet, if the occupant clutches an object while walking, and if the occupant walks at a normal speed.

In some embodiments, if any of the one or more conditions have not been met, the computer device communicates an alert to a caregiver of the occupant.

In at least one embodiment, one of the conditions is met if multiple siderails of the person support apparatus are raised. The database includes attribute data regarding the color and/or shape of the siderails, and the computer device utilizes the attribute data when determining if multiple siderails of the person support apparatus are raised.

One of the conditions is met if a fall risk indicator is present within a vicinity of the person support apparatus, in at least one embodiment. The fall risk indicator includes at least one of: (1) a sign, and (2) a bracelet worn by the occupant. The database includes attribute data regarding the sign and/or bracelet, and the computer device utilizes the attribute data when determining if the fall risk indicator is present.

One condition is met, in some embodiments, if one or more of the following seven objects are positioned within reach of the occupant while the occupant is positioned on the person support apparatus: (1) an entertainment control, (2) a nurse call pendant, (3) a drink, (4) a telephone, (5), eyeglasses, (6) a bedpan, and (7) a urine bottle. The database includes attribute data regarding one or more of the seven objects. The attribute data includes color data and/or shape data regarding the object(s), and the computer device utilizes the attribute data when determining if the at least one of the seven objects is within reach of the occupant.

One condition is met if no obstacles are present along a pathway between the person support apparatus and a restroom, in at least one embodiment. The database includes data identifying a location of the restroom.

In some embodiments, the system includes a second camera adapted to capture second images of at least a portion of a room in which the person support apparatus is located. The second camera outputs second image data representative of the second images, and the computer device also analyzes the second image data to determine if the condition is met.

One of the conditions is met, in some embodiments, if the height of a support surface of the person support apparatus is at its lowest height, and/or if a brake of the person support apparatus is activated. In some embodiments, the analysis of whether the brake is activated or not is carried out by consulting attribute data of the person support apparatus that is stored in the database. The attribute data identifies the location of a visual indicator on the person support apparatus that is illuminated when the brake is activated. The computer device determines if the brake is activated by analyzing the image data to determine a state of the visual indicator.

In many embodiments, the system also includes a depth sensor in communication with the computer device. In one version of the depth sensor, it is configured to emit infrared light toward the person support apparatus and detect reflections of the infrared light.

In at least one embodiment, the computer device identifies a location of the occupant's head in the image data and automatically blurs that location in the image data. The computer device stores in memory the image data containing the blurred location.

The camera is part of a camera system, in some embodiments, that includes a plurality of cameras, at least one of which is adapted to capture images of the occupant while walking and output walking image data representative of the images of the occupant captured while walking. The camera system is in communication with the computer device and the computer device assesses a gait of the occupant based on the walking image data.

According to another embodiment, a monitoring system is provided that includes a camera, a database, and a computer device. The camera captures images of at least a portion of a person support apparatus and outputs image data representative of the images. The database contains patient care protocol data that defines one or more tasks to be performed by a caregiver assigned to an occupant of the person support apparatus. The computer device communicates with the camera and database and analyzes the image data in order to detect a presence of the caregiver in a vicinity of the person support apparatus and to determine if the one or more tasks have been performed.

In some embodiments, a user interface is also included that is in communication with the database. The user interface allows an authorized user to enter information into the database defining the task.

In some embodiments, the computer device issues an alert if any of the tasks have not been performed prior to the caregiver exiting a room in which the person support apparatus is located.

The monitoring system includes a second camera, in some embodiments, that is adapted to capture second images of at least a portion of a room in which the person support apparatus is located. The second camera outputs second image data representative of the second images. The computer device analyzes the second image data to determine if the one or more tasks have been performed.

The one or more tasks include, in at least one embodiment, performing a fall risk assessment of the occupant and entering data from the fall risk assessment into a computer.

In some embodiments, the one or more tasks include any one or more of the following: turning the occupant; changing a dressing on a wound of the occupant; performing therapy on the occupant; visiting the occupant; taking a vital sign measurement of the occupant; administering medication to the occupant; starting or stopping an IV of the occupant; starting or stopping a compression device used to treat the occupant; adjusting an angle of a head section of the person support apparatus; and starting or stopping a ventilator used on the occupant.

The computer device is further adapted, in at least one embodiment, to communicate information—if the computer device determines that at least one of the tasks has been performed—to an electronic medical record indicating that the at least one of the tasks has indeed been performed. In some embodiments, the computer device transmits a reminder message of the task to the caregiver. The reminder message is transmitted if the one or more tasks remain uncompleted after expiration of a time period, or after the occurrence of an event (e.g. the caregiver leaving the room without completing the task, or the detection by the computer device of the presence of the caregiver within the vicinity of the person support apparatus). The reminder message is transmitted to the person support apparatus for display on a display of the person support apparatus.

In some embodiments, the one or more tasks include activating an exit detection system associated with the person support apparatus. The activation may be based upon a fall risk assessment associated with the occupant of the person support apparatus. That is, the computer device automatically activates the exit detection system after the caregiver leaves the vicinity of the person support apparatus if the fall risk assessment indicates that the occupant is a fall risk. Additionally, and/or alternatively, the computer device automatically activates the exit detection system after the caregiver leaves the vicinity of the person support apparatus if the fall risk assessment is not present in the database.

According to another embodiment, a person support apparatus is provided that includes a camera, a database, and a computer device. The camera captures images of at least a portion of a person support apparatus and outputs image data representative of the images. The database contains an exit detection algorithm for detecting, based on the image data, when an occupant of the person support apparatus may be about to exit the person support apparatus. The algorithm includes at least one occupant movement threshold used in determining whether to issue an exit detection alert. The computer device communicates with the camera and the database, and the computer device is adapted to analyze the image data to determine if the occupant is engaged in an activity. The computer device adjusts the threshold if the computer device determines that the occupant is engaged in the activity.

The activity includes eating and/or sleeping in some embodiments. When the activity is sleeping, the computer device analyzes the image data, in at least one embodiment, to determine if the occupant's eyes are open when determining if the occupant is sleeping. When the activity is eating, the computer device analyzes the image data, in at least one embodiment, to determine if one or both of the occupant's hands are repetitively moving toward the occupant's mouth when determining if the occupant is eating.

The computer device increases the threshold when the occupant is engaged in the activity, thereby requiring greater movement before the exit detection alert is issued.

In some embodiments, the computer device also determines whether the person support apparatus is a chair or a bed. In making this determination, the computer device may utilize attribute data regarding a shape of a chair and/or a shape of a bed. Such attribute data is stored in the database. The database also includes, in some embodiments, multiple exit detection algorithms. A first one of the multiple exit detection algorithms is used when the person support apparatus is a chair, and a second one of the multiple exit detection algorithms is used when the person support apparatus is a bed. The computer device selects the first or second exit detection algorithm based upon whether the person support apparatus is a chair or bed.

The computer device and database are housed in a common housing, in at least one embodiment. In other embodiments, the computer device is located in a room in which the person support apparatus is positioned, and the database is maintained on a server of a local area network that is in communication with the computer device.

If the computer device is located remotely from the person support apparatus, it is configured in at least one embodiment to transmit an exit detection message to the person support apparatus when issuing an exit detection alert. In response, the person support apparatus may communicate the alert to a nurse call system and/or generate audio and/or visual indications of the alert.

In some embodiments, the computer device communicates with a clock and the computer device is adapted to change the threshold based upon a time of day.

The database includes, in at least one embodiment, attribute data regarding a shape of an overbed table, and the computer device utilizes the attribute data to determine a position of the overbed table relative to the person support apparatus. The computer device changes the threshold based upon the position of the overbed table relative to the person support apparatus.

According to still another embodiment, a monitoring system is provided that includes a camera and a computer device in communication with the camera. The camera captures images of at least a portion of a person support apparatus and at least a portion of an occupant thereof, and the camera outputs image data representative of the images. The computer device analyzes the image data to determine if the following conditions are met: (1) the occupant may be about to exit the person support apparatus, and (2) the occupant is standing. The computer device issues a first alert if the first condition is met and issues a second alert if the second condition is met. The first alert is different from the second alert.

In some embodiments, the computer device is further adapted to determine if the occupant is walking and to issue a third alert if the occupant is walking. The third alert is different from both the first and second alerts.

In some embodiments, the computer device transmits a first alert message to the person support apparatus when issuing the first alert and transmits a second alert message to the person support apparatus when issuing the second alert. Alternatively, or additionally, the computer device transmits a first alert message to a nurse call system when issuing the first alert and transmits a second alert message to the nurse call system when issuing the second alert.

In at least one embodiment, the computer device analyzes the image data to detect a presence of a caregiver and to transmit an alert silence message after detecting the presence of the caregiver. The alert silence message may be transmitted to the person support apparatus whereby the person support apparatus reduces a volume of an alert sound in response thereto.

According to still another embodiment, a monitoring system is provided that includes a camera system and a computer device. The camera system includes a plurality of cameras and is adapted to capture images of first and second person support apparatuses. The camera system outputs image data representative of the images. The computer device communicates with the camera system and analyzes the image data to determine if the first or the second person support apparatus is occupied by a person. The computer device issues an alert if the person of the occupied person support apparatus is about to exit the occupied support apparatus.

The monitoring system consults a database in which a fall risk assessment of the person is storable, in at least one embodiment, and the computer device is adapted to not issue the alert if the fall risk assessment indicates that the person is not a fall risk. Additionally, or alternatively, the computer device is adapted to issue the alert if the fall risk assessment is not present in the database. Still further, the computer device updates the fall risk assessment based upon an analysis of the image data, in at least one embodiment.

In some embodiments, the computer device is in communication with a database containing patient identification data, and the computer device determines if the person is a patient of a healthcare facility or not based upon the patient identification data. The computer device issues the alert only if the person is a patient of the healthcare facility.

The first person support apparatus is a bed and the second person support apparatus is a chair, in some embodiments.

Before the different embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE EMBODIMENTS

A. Overview

Figure 1:
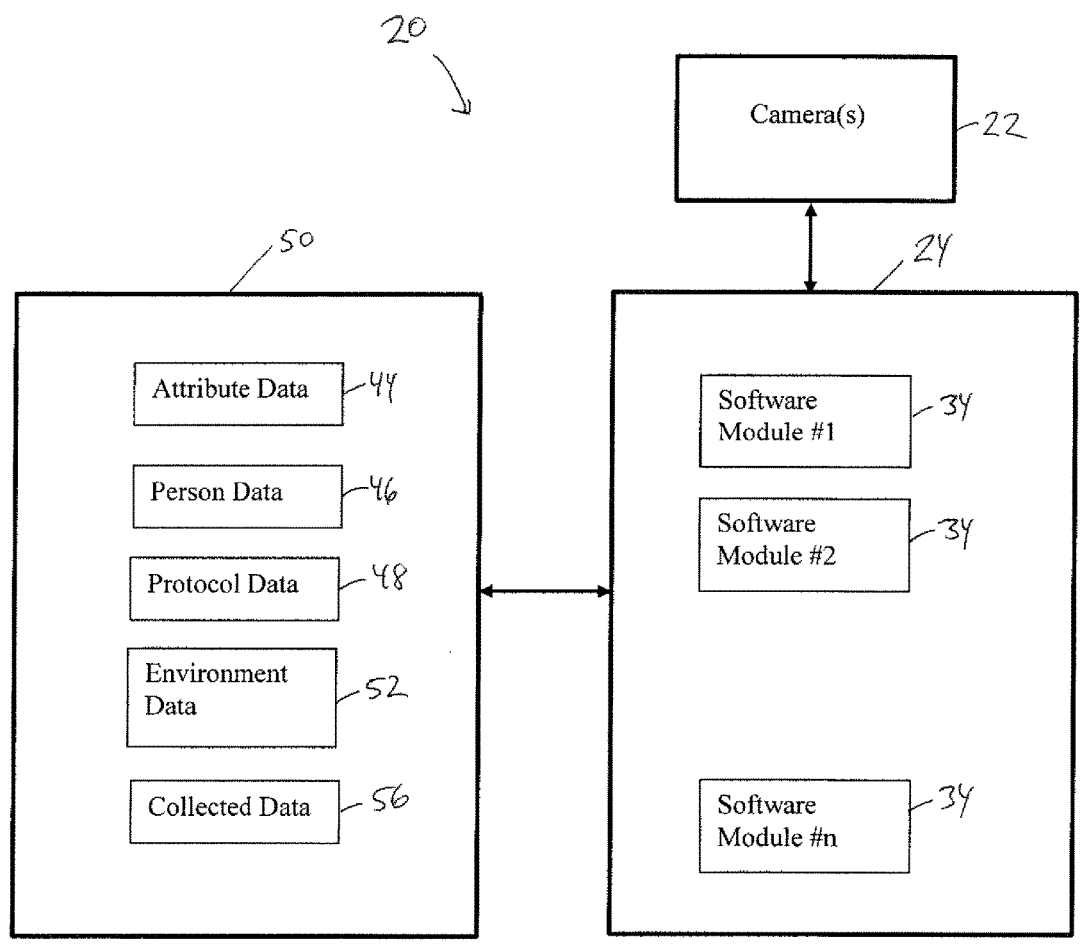
FIG. 1 is a block diagram of a video monitoring system according to a first embodiment.

A video monitoring system 20 according to a first embodiment is shown in FIG. 1. Monitoring system 20 includes one or more conventional video cameras 22 and/or other types of vision sensing or motion sensing equipment. Video monitoring system 20 is adapted to sense one or more conditions in a room or other environment, and/or to sense one or more actions undertaken by one or more persons in the room or other environment. In some embodiments, the data gathered by the video monitoring system is processed by appropriate hardware and/or software to determine whether an alert or other type of notification should be forwarded to appropriate personnel. In other embodiments, the data gathered by video monitoring system 20 is analyzed and electronically forwarded to one or more structures that are in communication with video monitoring system 20, as will be discussed in greater detail below. Video monitoring system 20 is especially suited for use in a patient care environment, such as a hospital, nursing home, or other facility where patients are housed, although it will be understood by those skilled in the art that it finds application in other environments as well.

Video monitoring system 20 of FIG. 1 includes one or more cameras 22, a computer device 24 that is in communication with the one or more cameras, and a database 50. Although the system of FIG. 1 illustrates camera 22, computer device 24, and database 50 as physically separate devices, it will be understood by those skilled in the art that in some embodiments, these structures are physically combined into a single unit. In still other embodiments, two out of three of these components (cameras 22, computer device 24, and database 50) are combined together into a single unit, while the other remains physically separate. In still other embodiments, computer device 24 is distributed among different locations such that, for example, a portion of the processing carried out by computer device 24 occurs on one or more processors contained within the same housing as one or more cameras 22 and/or database 50, while another portion of the processing carried out by computer device 24 occurs on one or more processors located elsewhere. As yet another example, computer device 24 may include one or more personal computers, laptops, appliances, network servers and/or services that are in communication with each other via one or more local area networks, wide area networks, and/or other types of networks, including the Internet. Still other variations in the relative locations of these three components are possible.

Computer device 24 is adapted to be loaded with one or more software modules 34 that carry out one or more monitoring features, as will be discussed in greater detail herein. Depending upon the different software modules 34 that are loaded on computer device 24, the monitoring features that video monitoring system 20 includes, as well as the functions it is capable of carrying out, will vary. In at least one embodiment, the software modules 34 that are loaded on computer device 24 are customized to individual customers, therefore resulting in video monitoring systems 20 that have different abilities. In some embodiments, the software modules 34 are capable of being added by a customer to monitoring system 20 after a customer purchases system 20. In other embodiments, the software modules 34 are selected by the customer at or prior to the time of purchase and remain static thereafter. In still other embodiments, video monitoring system 20 is sold to customers with a selected set of software modules 34 and features that are preselected by the manufacturer of video monitoring system 20, rather than the customer.

Seven different categories of monitoring features that video monitoring system 20 is capable of carrying out are described in greater detail below in section D. These seven different categories are the following: (1) Protocol Compliance/Documentation; (2) Patient Activity Monitoring; (3) Equipment Monitoring; (4) Asset Tracking; (5) Patient Visitation Metrics; (6) Video and Non-Video Data Integration; and (7) Gesture-Based Controls. Each of these categories includes multiple monitoring features that video monitoring system 20 is capable of carrying out, as described below. Computer device 24 is capable of simultaneously carrying out all of the monitoring features in each of these seven categories. However, as noted above, computer device 24 can be loaded with fewer than all of the software modules that are necessary to carry out all of the monitoring features in all seven of these categories. Thus, video monitoring system 20 is configurable to perform anywhere from only a single one of the below-described monitoring features all the way up to all of the monitoring features described below. It will also be understood by those skilled in the art that video monitoring system 20 can be modified further to include additional or alternative monitoring features that fall within one or more of these seven categories, as well as additional or alternative monitoring features that fall in categories outside of these seven.

The hardware that is included in video monitoring system 20 shown in FIG. 1 is described in more detail in section B below. More specifically, subsections 1-3 of section B includes a description of the core components of video monitoring system 20, which include cameras 22, computer device 24, and database 50. Subsection 4 describes additional sensors that are includable in system 20, depending upon the specific software modules 34 that are incorporated into computer device 24. In other words, it is not necessary to include any of the additional sensors described in subsection 4 in order to carry out many of the features of video monitoring system 20. However, by including one or more of the additional sensors described therein, a greater number of software modules 34 can be incorporated into computer device 24, and a greater number of functions can be performed by system 20. Subsection 5 describes in more detail the basic types of existing information technology (IT) infrastructure that are commonly found in typical healthcare facilities. Depending upon the specific implementation of system 20 (i.e. which software modules and hardware it includes, as well as the functions it is configured to perform), as well as the specific IT infrastructure of a given healthcare facility, video monitoring system 20 interacts with one or more components of this IT infrastructure in carrying out its functions.

Section C describes in more detail several of the general functions that are performed by video monitoring system 20. These general functions include person identification (subsection 1), object recognition (subsection 2), facial blurring (subsection 3), record keeping (subsection 4), and notification/alarming (subsection 5).

Section D below describes in more detail the seven monitoring features mentioned above, any one or more of which may be incorporated into video monitoring system 20, depending upon it specific configuration. Many of these seven monitoring features include multiple sub-features or functions that can be implemented in system 20, either alone or in combination with each other, depending upon the specific set of software modules that computer device 24 includes. For example, a variety of different protocol monitoring functions are described in subsection 1, such as fall prevention protocols, infection control protocols, pressure ulcer management protocols, and still other protocols. As another example, in subsection 2, a variety of different patient activity monitoring functions are described, such as monitoring a patient's exit from a patient support apparatus (e.g. bed, chair, etc.); monitoring whether a patient is eating or not; monitoring whether a patient is sleeping or not; and monitoring movement of the patient about his or her environment (e.g. bed, bathroom, hallway, etc.). Still other monitoring features are described in subsections 3-7.

B. System Hardware

Figure 2:
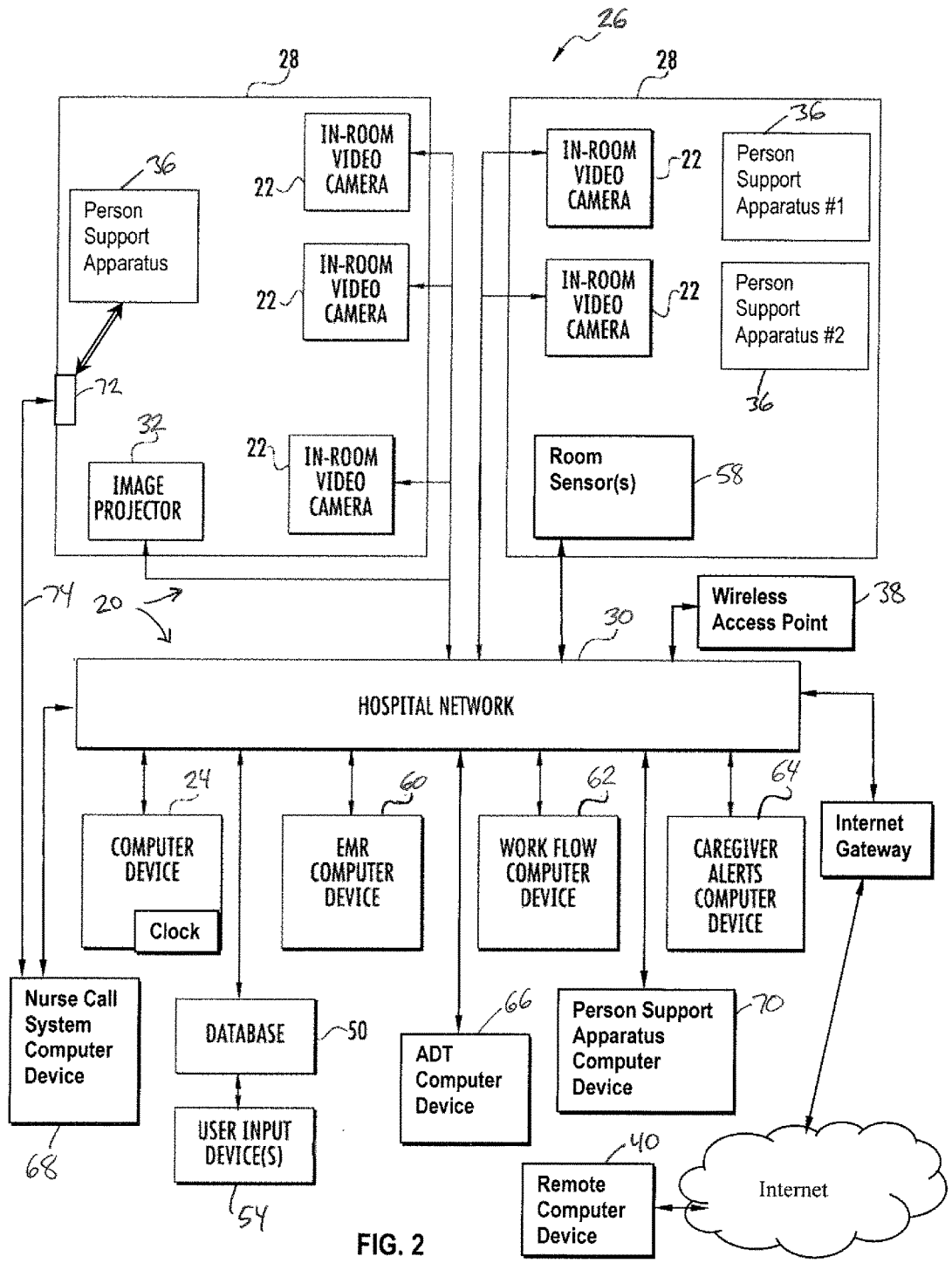
FIG. 2 is a block diagram of the video monitoring system of FIG. 1 shown in a first illustrative environment.
Figure 3:
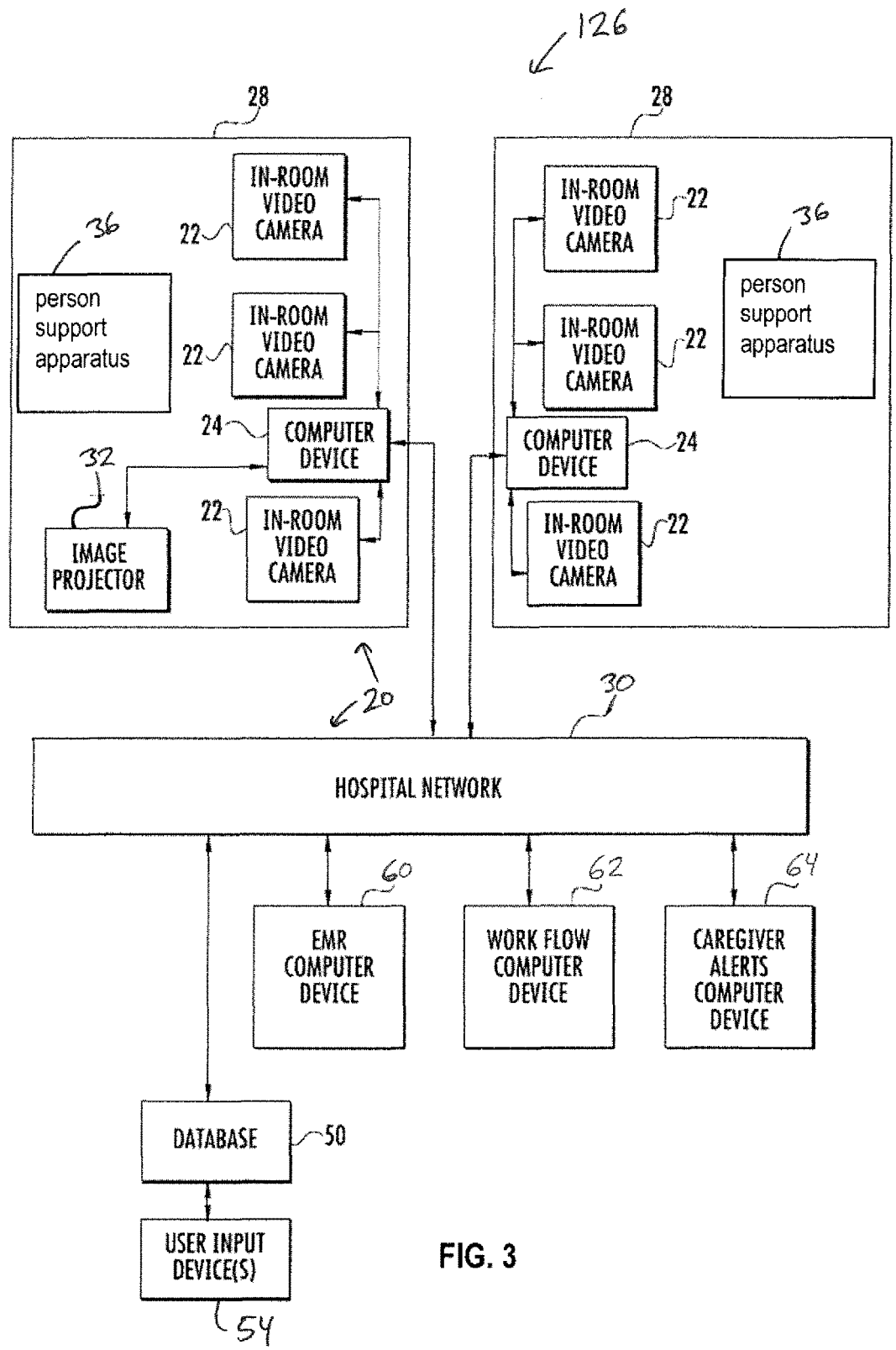
FIG. 3 is a block diagram of the video monitoring system of FIG. 1 shown in a second illustrative environment.
Figure 4:
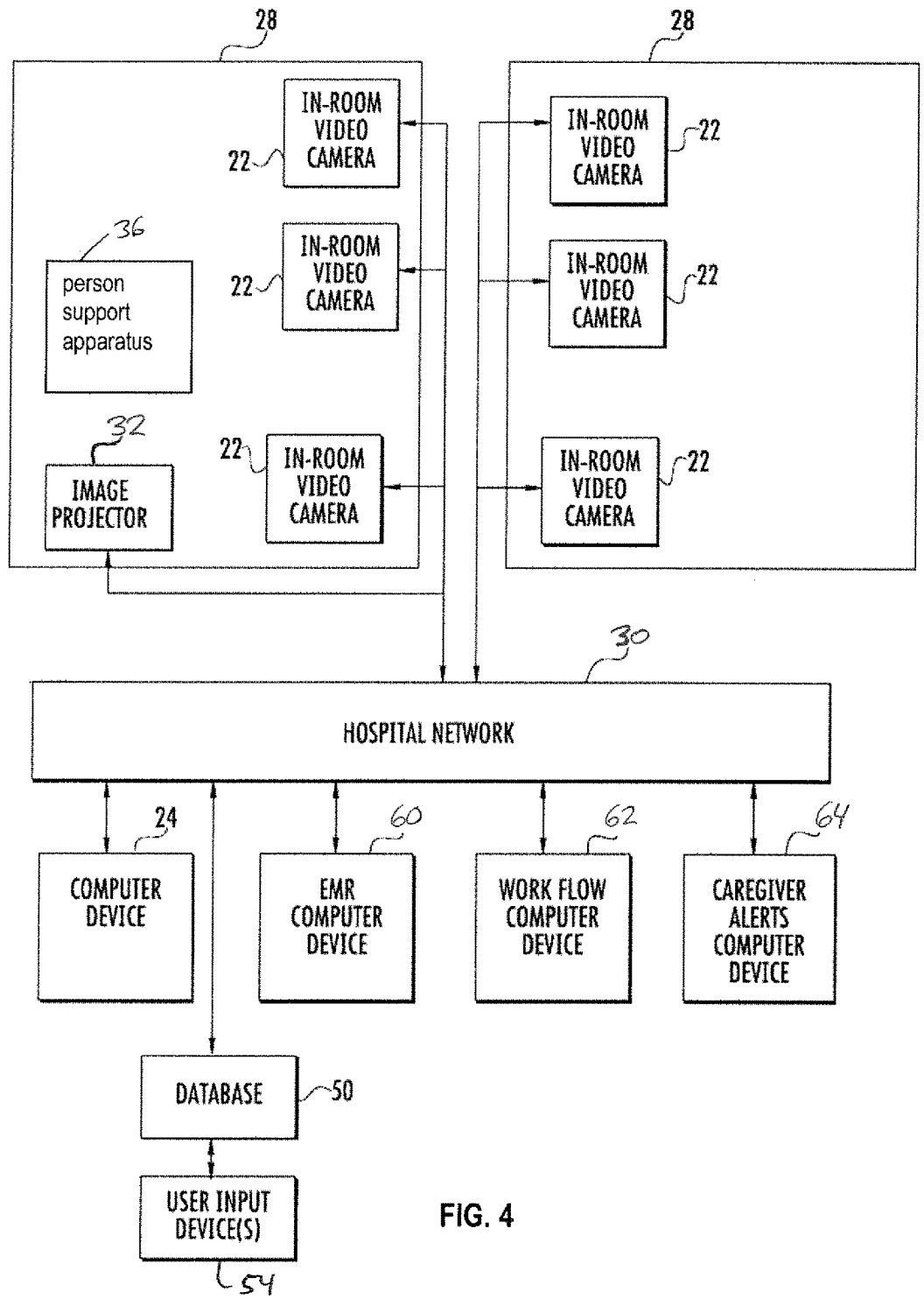
FIG. 4 is a block diagram of the video monitoring system of FIG. 1 shown in a third illustrative environment.

Video monitoring system 20 includes one or more cameras 22, a computer device 24 that is in communication with the one or more cameras, and a database 50 (FIG. 1). Additional devices may be added to these components that, as will be described in greater detail below, may vary from installation to installation. Further, the number of these additional devices, the manner in which they communicate with each other and with the existing IT infrastructure of a healthcare system, as well as their location within a healthcare facility will vary from one facility to another. FIGS. 2, 3, and 4 illustrate several different environments in which video monitoring system 20 may be specifically implemented, as well as several different configurations of monitoring system 20. It will be understood that the configurations of FIGS. 2-4 are merely illustrative and non-exhaustive examples of the wide variety of different configurations in which the video monitoring systems of the present invention can be implemented.

More specifically, FIGS. 2, 3, and 4 illustrate first, second, and third environments 26, 126, and 226, respectively. Environments 126 and 226 are different from environment 26 primarily in that environments 126 and 226 include fewer devices than are present in FIG. 2, and the communication layout of the components of video monitoring system 20 in these three environments is different. It will be understood that a wide variety of additional changes beyond the variations shown in FIGS. 2-4 are possible. As but a few small examples, it will be understood that, although FIGS. 2-4 all show video monitoring system 20 as implemented in an environment having two patient rooms 28, system 20 can be applied to environments having only a single room 28, or to systems having more than two rooms 28. Further, although environments 126 and 226 illustrate three cameras 22 in each room 28, different numbers of computer devices on a healthcare network 30, as well as one room 28 with a projector 32 and another room 28 without a projector, it will be understood that these aspects are merely intended to illustrate some of the variations in which system 20 can be implemented in a given environment, and are not intended to suggest that these and other aspects are not modifiable.

1. Cameras 22

In one embodiment, any one or more of the video cameras 22 of system 20 are motion and image sensing devices sold under the brand name Kinect™, or variations thereof, by Microsoft Corporation of Redmond, Wash., USA. The Kinect™ motion sensing camera device includes an RGB (red, green, blue) camera, a depth sensor, and a multi-array microphone. The Kinect™ device comes in at least two different versions, one of which is adapted to provide inputs into Microsoft's Xbox 360 and/or Xbox One video game consoles, and one of which is adapted to interface with the Microsoft Windows 7 operating system. Either variation is usable in the video monitoring systems disclosed herein. The Kinect™ device provides full-body 3D motion, facial recognition, and voice recognition capabilities. The depth sensor may include an infrared laser projector combined with a complementary metal oxide semiconductor (CMOS) sensor, which captures reflected signals from the laser projector and combines these signals with the RGB sensor signals. The Kinect™ motion sensing device automatically detects the position of one or more persons and outputs data indicating the locations of multiple body portions, such as various joints of the person, multiple times a second. Such information is then processed to determine any one or more of the conditions discussed herein.

In other embodiments, any one or more of the video cameras 22 are a WAVI Xtion™ motion sensing system, or variations thereof, marketed by Asustek Computer, Inc., which has a principal place of business in Taipei, Taiwan. The WAVI Xtion™ motion sensing system uses one or more depth sensors to sense the position and movement of people without requiring the people to hold any objects.

In still other embodiments, other types of video cameras 22 are used, or a combination of one or more of the Kinect™ cameras 22 is used with one or more of the WAVI Xtion™ cameras 22. Still other combinations of cameras 22 may be used. Modifications may also be made to the camera 22, whether it includes a Kinect™ camera or a WAVI Xtion™ camera, or some other camera, in order to carry out the functions described herein, as would be known to one of ordinary skill in the art. It will further be understood that depth sensing devices may be used in system 20 that are physically separate from the image sensing portion of video cameras 22. The terms "video camera" or "camera," as used herein, will therefore encompass devices that only detect images, as well as devices that detect both images and depths. The images detected may refer to both ambient light images or thermal images, or still other types of images.

Whatever type or types of video cameras 22 that are used, such cameras 22 may include additional sensors beyond the image sensors and/or depth sensors, such as microphones, or other sensors. In some embodiments, more than one camera 22 is used within a room, or more than one camera 22 is used for monitoring a given patient. The use of multiple cameras for a given room or patient decreases the likelihood of the camera's view being obstructed, and may increase the different types of information that may be gathered by the cameras 22. When multiple cameras 22 are used within a given room or for a given patient, the cameras 22 may all be of the same type, or they may consist of different types of cameras (e.g. some cameras may include both image sensors and depth detectors while others may only have image sensors).

The one or more cameras 22 that are positioned within a given room, or other location, are in electrical communication with computer device 24 via a communications medium, such as, but not limited to, a hospital network 30, which may be a local area network (network), a wide area network (WAN), or any other type of network, including a network that is coupled to the Internet (FIG. 2). In at least one embodiment, network 30 is an Ethernet-based network. The video cameras 22 are positioned in a patient care facility, such as a hospital, nursing home, or the like, and record images of various activity. Such images are converted to electrical signals which are forwarded to computer device 24 for processing in various manners, as will be described in more detail below. In the environments 26, 126, and 226, shown in FIGS. 2-4, there are two or three video cameras 22 positioned within each single room 28. The number of video cameras 22 within a room, or other area, may be varied, and may depend upon what information is gathered from the video images. The physical location of the video cameras 22 within a room or other area may also vary in accordance with the layout of the room—such as, but not limited to, the physical location of a person support apparatus 36 (e.g. bed, cot, stretcher, chair, recliner, etc.) within the room, the location of the restroom, and the location of furniture or objects in the room—such that the cameras 22 are suitably positioned to be able to capture the desired images. As was noted previously, the video cameras 22 include, in addition to an image sensor, a depth sensor (which may utilize infrared technology), or other sensors. The image sensor is a digital image sensor in order to facilitate the digital processing of the recorded signals, in at least one embodiment.

In the environment shown in FIG. 2, the cameras 22 within each room 28 communicate their electronic images to computer device 24 over network 30. If cameras 22 include a depth sensor and/or microphones, the depth sensor signals and/or microphone signals are also forwarded to computer device 24 over network 30. The architecture of FIG. 2 may be modified in a variety of different manners.

One such variation is shown in FIG. 3, which illustrates a computer device 24 positioned in each room that is dedicated to processing the images and/or depth sensor readings generated by the cameras 22 positioned within that room. One of the in-room computer devices 24 in FIG. 3 is also programmed to control the image projector 32 within that room. Although the other room shown in FIG. 3 does not include an image projector 32, it will be understood that system 20 can be modified to include another image projector 32 positioned in that second room, if desired.

After processing all or a portion of the data received from the cameras 22, the in-room computer devices 24 of FIG. 3 transmit messages regarding such processing onto the hospital network 30. Such messages are forwarded directly to one or more other computer devices that are in communication with network 30. The computer devices that are the recipients of these message may vary from installation to installation, depending upon what existing IT equipment a particular healthcare facility has installed in their facility. Common types of such existing IT equipment are described in greater detail below in subsection 6. Video monitoring system 20 is configured to interact and communicate with all of these types of existing equipment, and/or any subsets of them. Indeed, in some embodiments, video monitoring system 20 operates without needing to interact with any of the existing IT equipment discussed below in subsection 5.

Cameras 22 communicate with network 30, in at least one embodiment, by way of hardwires connecting each camera 22 to network 30. Such hardwires are, in at least one embodiment, Ethernet cables that are plugged into existing Ethernet ports within rooms 28. In an alternative embodiment, cameras 22 communicate wirelessly with network 30 by transmitting messages to one or more wireless access point 38 of network 30. Such wireless communication takes place via WiFi (e.g. IEEE 802.11b, g, n, ac, ad, etc.), in at least one embodiment. Other types of communication between cameras 22 and computer device 24 may also be used.

In some embodiments (not shown), each video camera 22 includes its own computer device 24 or its own portion of computer device 24, either separately attached thereto, or integrated into the camera 22 itself. In such embodiments, each computer device 24 is dedicated to processing, or pre-processing, the electronic images, depth sensor readings, and/or voice signals gathered by the associated video camera 22. The results of such processing, or pre-processing, are then forwarded directly to network 30, or to one or more intermediate computers (not shown) before being sent to network 30. Computer devices 24 provide the software intelligence for processing the images, depth sensor data, and/or voice data recorded by cameras 22, and the precise physical location of this intelligence can vary in a wide variety of different manners, from embodiments in which all the intelligence is centrally located to other embodiments wherein multiple computing structures are included and the intelligence is physically distributed throughout the care giving facility.

As was noted above, the precise number and location of cameras 22 within a given room or other area may vary, depending upon the data that is intended to be captured by the cameras 22. In some embodiments, cameras 22 are mounted to the walls, the ceiling, objects within a room, such as the hospital bed or other furniture, or in still other locations. Each camera 22 may be either mounted in a fixed orientation, or it may be coupled to a mounting structure that allows the orientation of the camera to be automatically adjusted by computer device 24 such that the camera may record images of different areas of the room by adjusting its orientation. Still further, each camera 22 includes zoom features that allow computer device 24, or another intelligent device, to control the zooming in and zooming out of the cameras 22 such that both close-up images and wider field of view images may be recorded, as desired.

More specifically, and as will be discussed in greater detail below, computer device 24 controls the zooming in and out of cameras 22 based upon the particular software modules 34 that it is executing. Some software modules 34 seek, if available, images that are focused more narrowly on specific items (e.g. persons, objects, or specific portions of persons or objects) within the camera's field of view. Whenever such items are detected, computer device 24 sends a message to one or more of cameras 22 to adjust the orientation of the camera 22, if necessary, and zoom in on the identified item. Images gathered by camera 22 while the camera has zoomed in on the identified item are then analyzed by computer device 24. If the desired information is not available from these captured images, computer device 24 instructs the associated camera 22 to zoom in further—if possible (and depending upon the specific software module 34)—to capture additional images of the item for processing and analysis by computer device 24.

In some embodiments, if a particular camera 22 is not able to capture specific information that is desired by a particular software module 34 after zooming in on the item of interest, computer device 24 instructs another camera 22 that is positioned in the same room 28 to change its orientation (if necessary) so as to have a field of view that encompasses, or is likely to encompass, the information of interest. Images from that second camera and then processed by computer device 24 to see if the specific information of interest is available. If not, computer device 24 instructs the camera 22 to zoom in on the item of interest so that close-up images of the item of interest can be processed by computer device 24 in its pursuit of the information of interest. These principles may be better understood by way of several examples described below, which are not intended to be an exhaustive list.

As one example, in some embodiments, computer device 24 is adapted to identify one or more persons by facial recognition. In some of these embodiments, computer device 24 first identifies that certain pixels in the captured image correspond to a person. After this generic identification of the person is performed, computer device 24 instructs one or more of the cameras 22 to zoom in on the facial area of the person. From this zoomed in view, computer device 24 analyzes the facial image pixels to determine if the person's face matches any of the facial data corresponding to known individuals that is stored in database 50. Once this facial data is captured, computer device 24 instructs the one or more cameras to zoom back out and return to a wider field of view.

If system 20 includes two cameras 22 in a particular room 28 and they are both able to capture images of the individual, it may turn out that the face of the individual is not pointed toward one of the cameras 22 at a particular moment, or the individual's face may be obstructed from view by one or more objects positioned in the line of sight between the camera 22 and the individual's face. In such cases, computer device 24 instructs the camera 22 whose view of the person's face is not obstructed to zoom in on the person's face and capture images of it. Computer device 24 then instructs the camera to zoom back out and return to its previous state. If one or more images of the person's face were successfully captured that included sufficient information to identify the individual, computer device 24 tags the images it captures of that individual with the individual's ID. If the one or more images of the person's face were insufficient to identify the individual—because, for example, the person's face was turned away from the camera, or for some other reason—computer device 24 re-attempts identification of the individual at a later moment in time using the same process just described.

In other examples, either instead of or in lieu of zooming in on individuals' faces for facial recognition, system 20 is configured to control cameras 22 to zoom in on identification tags that are attached to equipment and/or personnel. Such zooming allows system 20 to read information that is visually present on the tag. Such tags may be used for tracking the location and/or usage of assets within a healthcare facility, or they may be used as a means of identifying individuals (either in addition to, or in lieu of, facial recognition). As yet other examples, system 20 is configured to control the zoom on cameras 22 in order to read the level of fluids in an IV bag; to read words and/or other indicia on medication, equipment, and/or signs; and/or to perform multiple other tasks, depending upon which software modules 34 are being executed by computer device 24 and the specific functions that are carried out by those software modules 34.

Although cameras 22 are primarily described herein as being adapted to capture visible light images, it is to be understood that, in at least some embodiments of system 20, one or more of cameras 22 are infrared image sensing devices. When equipped with one or more of such infrared image sensing devices, system 20 is able to capture images of all or a portion of rooms 28 even when the room is dark. The capturing of such infrared images utilizes existing ambient infrared light within room 28, in some embodiments, and in other embodiments, utilizes one or more sources of infrared light that are provided as part of system 20. In addition to capturing images in dark or low-light conditions, utilizing one or more infrared cameras 22 also allows system 20 to detect thermal images. Some software modules 34 are adapted to utilize such thermal images, if available, for carrying out their function. For example, at least one software module 34 that tracks the movement of a patient in a hospital bed is adapted to utilize thermal images to detect the patient's movement while covered with a sheet and/or other bedding. Another software module 34 to capture patient movement in low light conditions that is indicative of the patient's impending, or actual, departure from his or her bed. Still other software modules 34 utilize the infrared image data in other manners and for other purposes.

2. Computer Device 24

In the embodiment illustrated in FIGS. 2 and 4, computer device 24 is a conventional server that communicates with both cameras 22 and projectors 32 over network 30. In other embodiments, such as the embodiment shown in FIG. 3, computer device 24 includes one or more personal computers (PCs) that are positioned in the rooms 28 of the healthcare facility. In still other embodiments, computer device 24 includes one or more dedicated electronic structures configured to carry out the logic and algorithms described herein. In still other embodiments, computer devices 24 are any combination of these or other known devices capable of carrying out the logic and algorithms described herein. Such dedicated electronic structures may include any combination of one or more processors, systems on chip (SoC), field programmable gate arrays (FPGA), microcontrollers, discrete logic circuitry, software and/or firmware. Regardless of whether computer device 24 is a single physical device, or is multiple physical devices working together (which may be located in different physical locations), computer device 24 includes the hardware, software and/or firmware necessary to carry out the algorithms described herein.

Each computer device 24 includes software installed thereon that is adapted to process the image data and/or sensor signals (e.g. depth and/or sound data) recorded by cameras 22. In at least one embodiment, such software includes one or more of the general functions described below in sections C.1-5 (e.g. person identification, object recognition, facial blurring, record keeping, and/or notification/alarming), as well as one or more software modules 34 that carry out one or more specific tasks. Both the software for the generalized functions and for the specific software modules 34 utilize, in at least one embodiment, many conventional software components that are available for recognizing video images and processing the information contained therein. Such commercially available software is combined with customized software and/or modifications in order to carry out the various functions described herein, as would be known to one of skill in the art.

For example, in one embodiment, the software used by computer device 24 to analyze the image and depth data from cameras 22 is processed using the commercially available software suite referred to as OpenCV (Open Source Computer Vision Library), which is an open source computer vision library supported by Willow Garage of Menlo Park, Calif. The OpenCV library has been released under the Berkeley Software Distribution (BSD) open source license. The OpenCV library has more than 2500 computer vision algorithms and is available for use with various commercially available operating systems, including Microsoft Windows, Linux/Mac, and iOS. The OpenCV algorithms include a comprehensive set of both classic and state-of-the-art computer vision and machine learning algorithms. These algorithms are designed to be used to detect and recognize faces, identify objects, classify human actions in videos, track camera movements, track moving objects, extract 3D models of objects, produce 3D point clouds from stereo cameras, stitch images together to produce high resolution images of entire scenes, find similar images from an image database, follow eye movements, recognize scenery and establish markers to overlay scenery with augmented reality, and other tasks.

The OpenCV library has to date included three major releases: versions 1.0, 2.0, and 3.0, and any one of these major versions (as well as any of the multiple intermediate versions), is suitable for carrying out the features and functions described in more detail herein. In at least one embodiment of video monitoring system 20, customized software is added to interact with and utilize various of the software algorithms of the OpenCV library in order to carry out the features described herein. Other commercially available software may also be used, either in addition to or in lieu of the OpenCV library.

In one embodiment, computer device 24 is sold to customers pre-loaded with a particular set of software modules 34 that cannot be changed. In other embodiments, the particular software modules 34 that are executed by computer device 24 can change, and can be adapted to suit the particular needs of a specific healthcare facility. In some such embodiments, system 20 is configured to enable the user of system 20 to add additional software modules 34 after purchase of system 20. In one such embodiment, one or more software modules 34 are available to be added to system 20 via an Internet connection of network 30 to one or more remote computer devices 40 (FIG. 2). The remote computer devices 40 comprise one or more servers that store, and make available to authorized individuals and/or entities (e.g. purchasers or lessees of system 20) one or more software modules 34. In other words, remote computer devices 40 act as a digital distribution platform. Remote computer devices 40 may host one or more websites and/or contain other functionality that enables additional software modules 34 to be transferred over the Internet to computer device 24 utilizing the healthcare facility's network 30 and its Internet connection and/or Internet gateway 42. Remote computer devices 40 are, in many embodiments, owned and/or under the control of the manufacturer and/or retailer of system 20 so that access to remote computer devices 40 can be limited to authorized purchases or system 20.

In at least one embodiment, a set of software modules 34 that are available for purchase and/or lease are stored on remote computer device 40 in a format similar to an app store, such as Google Play and/or Apple's iOS App store. Authorized users of system 20 are able to access the software modules 34 stored on remote computer device 40, review information documenting the functionality and requirements of the software modules 34, and then download one or more of the software modules 34 to computer device 24. The downloading of software modules 34 may be free or fee-based.

In still other embodiments, computer device 24 is integrated into one or more patient support apparatuses 36 and software modules 34 are downloadable to computer device 24 in any of the manners that the software applications 78, 92, 94, and/or 98 are disclosed to be downloadable in commonly assigned PCT patent application number PCT/US2014/024672 (WO 2014/150970) filed Mar. 12, 2014 by applicant Stryker Corporation and entitled PATIENT SUPPORT APPARATUS WITH REMOTE COMMUNICATION, the complete disclosure of which is hereby incorporated herein by reference. In still other embodiments, computer device 24 is positioned outside of the person support apparatuses 36 (such an any of the locations shown in FIGS. 2-4 or elsewhere) and the systems disclosed in the aforementioned PCT/US2014/024672 patent application are modified to transmit software, such as software modules 34, to the location of computer device 24, rather than to person support apparatuses 36.

When more than one computer device 24 is present in a particular system 20, or when computer device 24 is a single physical device adapted to run multiple instances of the modules that it executes, system 20 can be configured such that different features, tasks, and/or activities are monitored in different rooms 28 of the healthcare facility. In other words, system 20 can be modified such that a first set of software modules 34 are executed by computer device 24 (or a first one of computer devices 24) for a first set of rooms 28, and a second and different set of software modules 34 are executed by computer device 24 (or a second one of computer devices 24) for a second and different set of rooms. Thus, as but one illustrative example, system 20 may be configured to control one or more devices based upon its recognition of specific gestures of authorized individuals in a specific set of rooms. In rooms outside of that specific set, system 20 may be configured such that, if one or more of the authorized individuals makes a similar gesture in any of the rooms outside of that specific set, system 20 does not control any of those devices.

In some embodiments, computer device 24 includes one or more displays, speakers, and/or lights for transmitting information to caregivers and/or for alerting caregivers of relevant conditions. At least one of the displays, speakers, and/or lights is positioned within each room 28 so that information and/or alerts can be conveyed to caregivers, regardless of the physical location of computer device 24. That is, in some embodiments, computer device 24 is positioned remotely from the room 28 (e.g. FIGS. 1 and 4) but a display, speaker, and/or light that is controlled by computer device 24 is positioned within each room 28.

3. Database 50

In addition to the components described above, video monitoring system 20 also includes one or more databases 50 (FIGS. 1-4). Each database 50 is constructed to be accessible by computer device 24 such that computer device 24 is able to use the contents of database 50 in carrying out the algorithms of the software executed by computer device 24. In one embodiment, such as shown in FIGS. 2-4, database 50 is placed in communication with computer network 30 such that computer device 24 can access the contents of database 50 over network 30. In other embodiments, database 50 is located elsewhere. One or more user input devices 54 are also included in system 20 in order to allow authorized personnel to add, update, search, edit, and/or delete information contained with database 50. Such user input devices include keyboards, cameras, scanners, touch screens, bar code readers, or other types of devices.

Database 50 contains information that is useful for the algorithms carried out by system 20 and the software modules 34 executed by computer device 24. As shown in FIG. 1, the information contained within database 50 can be broadly classified into at least five types of data: attribute data 44, person data 46, protocol data 48, environment data 52, and collected data 56. These five different types of data are described in more detail below in sections a-e.

a. Object Attribute Data 44

Attribute data 44 includes data regarding the various objects that video monitoring system 20 is adapted to detect. The attribute data includes the color, size, and/or shape of the objects that system 20 is adapted to detect. For some objects, additional data beyond its color and shape is also included, as will be discussed in greater detail below.

The specific objects that system 20 is adapted to detect will vary, depending upon what set of software modules 34 computer device 24 is executing. In general, database 50 includes attribute data for any one or more of the following objects: beds; chairs; mattresses; overbed tables; control pendants; telephones; cups; IV/Heparin locks; floor mats; fall risk signs; and/or other types of signage; medical equipment (e.g. ventilators, pumps, therapy devices, etc.); identification badges (whether for persons or objects or both); personal protective equipment (PPE) for protection against infection (e.g. masks, gloves, facial shields, gowns, etc.); patient personal property (e.g. cell phones, tablet computers, books, magazines, purses, etc.); uniforms or other identifiable clothing worn by specific types of individuals; eating utensils (silverware, plates, trays, etc.); handwashing stations; computer-on-wheels (COWs); bedding (sheets, pillows, blankets); cleaning equipment (mops, sponges, etc.); medications and medication containers; sequential compression devices; pressure reducing heel boots; commodes, bedpans, and/or urine bottles; equipment power and data cables; wall outlets (e.g. A/C power outlets, data outlets, etc.); and other equipment and/or other types of objects that are expected to be found within the rooms of a healthcare facility in which system 20 is implemented.

For some of these objects, database 50 also contains attributes for one or more of the components of the objects. For example, in many embodiments, database 50 includes, in addition to attribute data sufficient to enable computer device 24 to recognize a bed within room 28, attribute data sufficient to enable computer device to separately identify the siderails of the bed, the head or Fowler section of the bed, the mattress, the footboard, the control panels on the bed, the litter of the bed, the power cable of the bed, and/or other components of the bed. Different software modules 34 rely upon the identification and/or monitoring of different ones of these components. Components of any one or more of the other objects identified above are also includable in database 50.

For some of the objects, the attribute data 44 is sufficiently specific to enable computer device 24 to not only identify the general type of object, but also to distinguish between more specific types of objects, including—in at least some cases—the manufacturer and/or model of a particular object or piece of equipment. For example, in some embodiments, database 50 includes attribute data for patient support apparatuses 36 (e.g. beds, chairs, recliners, etc.) that is specific to particular manufacturers of such equipment and particular models made by that manufacturer. In this way, for example, computer device 24 can utilize database 50 to differentiate between, for example, an S3 brand hospital bed manufactured by Stryker Corporation of Kalamazoo, Mich. and an InTouch brand hospital bed that is also manufactured by Stryker Corporation. Brand and/or model-specific attribute data for other devices besides beds is also storable in database 50.

For other objects, the attribute data 44 in database 50 is more generic and includes a wider range of possible sizes, colors, and/or shapes. Objects with such generic attribute data 44 include, for example, personal possessions of the patients (e.g. cell phones, computer tablets, purses, books, magazines, etc.) and/or other items that come in differing shapes, colors, and/or sizes.

For some objects—such as, but not limited to those that come in different shapes, sizes, and/or colors—database 50 includes other attribute data 44 besides, or in addition to, color, size, and/or shape data. For example, for some types of objects, database 50 includes attribute data 44 that associates specific types of behaviors with those types of objects. This behavior-associated attribute data enables computer device 24 to identify these objects when computer device 24 is not able to do so based solely upon size, color, and/or shape data regarding the object. For example, in one embodiment, database 50 contains behavior-associated attribute data that indicates that image/depth data captured by cameras 22 of an individual holding an object in front of the individuals' face and making occasional crosswise swinging motions with his or her fingers, hand, or wrist is indicative of the object being a book or magazine. As another example, database 50 contains behavior-associated attribute data that indicates that image/depth data captured by cameras 22 of an individual holding an object in front of the individual's face and making occasional pressing motions on the object with his or her fingers or thumb is indicative of the object being a cell phone or computer tablet. Database 50 can, of course, contain additional behavior-associated attribute data beyond these two examples.

Such behavior-associated attribute data may also be included in database 50 for any objects, regardless of whether or not the object comes in different sizes, shapes, and/or colors. When such behavior-associated attribute data is included, computer device 24 utilizes this data to assist in identifying objects when identification is not possible (e.g. due to a visual obstruction, etc.), or when such identification yields a questionable probability of a successful match based upon incomplete correlations between the captured image/depth data from cameras 22 and the color, size, and/or shape attribute data 44 stored in database 50. Thus, as but one example, database 50 contains—in some embodiments—behavior-associated attribute data for silverware and/or cups that indicate that objects detected by cameras 22 to be moving back and forth from a location near a person to the person's mouth are likely to be eating utensils. Other types of behavior-associated attribute data are also includable in database 50.

In addition to color, shape, size, and behavior-associated data, a number of additional types of attribute data 44 are included in database 50, in at least some embodiments. Such additional data includes, but is not limited to, time-associated attribute data, personnel-associated attribute data, position-based attribute data, movement-associated data, and thermal characteristic data. Time-associated attribute data includes data indicating that the presence of certain objects is associated with one or more specific times of day, days of week, and/or calendar days. Such time-associated attribute data therefore provides an indication that the likelihood that an as-yet-unidentified object detected within the image/depth data captured by camera(s) 22 corresponds to one or more identified objects varies according to what time of day, day of week, and/or day of the year it is. Thus, as but one example, time-associated attribute data is included in at least one embodiment of database 50 that indicates that food and/or eating utensils are more likely during meal times.

Personnel-associated attribute data includes data indicating that certain objects are associated with certain personnel. Such data therefore provides an indication that the likelihood that an as-yet-unidentified object detected within the image/depth data captured by camera(s) 22 corresponds to one or more identified objects varies according to what personnel, or what classes of personnel, are using the object, are near the object, and/or carrying the object. As but one example of this type of personnel-associated data, database 50 includes, in at least one embodiment, data indicating that objects brought into a patient's room by cafeteria personnel are highly likely to be food or eating utensils. Manners in which personnel can be identified individually or by types are discussed in greater detail below in subsection b and section C.1.

Position-associated attribute data includes data indicating that certain objects are associated with certain absolute positions in the room, or relative positions to one or more other objects in the room. Such data therefore provides an indication that the likelihood that an as-yet-unidentified object detected within the image/depth data captured by camera(s) 22 corresponds to one or more identified objects varies according to the position of the detected object, either relative to the room 28 or relative to one or more objects within the room 28. Thus, as but one example of this type of position-associated attribute data, database 50 includes, in at least one embodiment, data indicating that an object that is positioned on top of a person support apparatus 36 and/or that is immediately underneath a patient is likely to be a mattress. As another example, objects positioned on the wall approximately 1-3 three feet from the ground are more likely to be electrical and/or data outlets. Still other position-associated attribute data may be included in database 50.

Movement-associated attribute data includes data indicating that certain objects are associated with certain types of movement and lack of movement. Such data therefore provides an indication that the likelihood that an as-yet-unidentified object detected within the image/depth data captured by camera(s) 22 corresponds to one or more identified objects varies according to whether or not the object moves and/or, if it does move, the type of its movement (e.g. direction of movement, frequency, range, path, etc.). Thus, as but one example of this type of movement-associated data, database 50 includes, in at least one embodiment, data indicating that an object that swings near a bed between the height of about 4-6 feet (or other range) is more likely to be an IV bag than an object positioned elsewhere or moving in a different manner. As another example, database 50 includes data, in at least one embodiment, indicating that objects on walls that do not move are more likely to be outlets, consoles, or the like, while objects that occasionally move on the wall in the presence of individuals are more likely to be temporarily affixed signs.

Thermal attribute data is stored in database 50 when system 20 is configured with one or more thermal cameras 22. Thermal attribute data includes data identifying the thermal characteristics of one or more objects. Such thermal attribute provides an indication that the likelihood of an as-yet-unidentified object corresponds to a known object will vary according to the thermal attribute data stored in database 50 and the thermal image data captured by one or more thermal cameras. Thus, for example, thermal image data indicating the presence of heat sources underneath blankets and/or bedding when a patient is positioned on the bed is likely to correspond to the legs, torso, and/or other body parts of the patient that are covered by the bedding. Thermal data may also be used to identify medical devices that are used for controlling the temperature of a patient, such as, but not limited to, thermal control devices of the type disclosed in commonly assigned U.S. patent application Ser. No. 14/282,383 filed May 20, 2014 by inventors Christopher John Hopper et al. and entitled THERMAL CONTROL SYSTEM, the complete disclosure of which is hereby incorporated herein by reference.

Regardless of the types of attribute data 44 that are contained within database 50, computer device 24 utilizes the attribute data 44 to determine if objects it detects in the visual images and depth readings of cameras 22 correspond to the object data stored in database 50. In many instances, the data gathered from cameras 22 (including depth readings) will not completely match the data stored in database 50. For example, in many cases, the depth and image data from the cameras 22 will only be available for those surfaces of the objects that are facing towards the camera. Computer device 24 may therefore not have complete information about the size, shape, and/or color of the objects detected by cameras 22. Nevertheless, computer device 24 is typically able to identify these objects by measuring the correlation between the detected data and the data in database 50. If the correlation exceeds a threshold, computer device 24 determines that the detected object matches the object identified in database 50, and assigns that identity to the detected object.

Some of the attribute data 44 is pre-loaded into database 50 by the manufacturer of system 20 based upon general objects expected to be found in all healthcare facilities (e.g. beds, electrical wall outlets, etc.). Other attribute data 44 is added to database 50 during, or after, installation of system 20 based upon the specific types of equipment that are used in that particular medical facility. For example, specific healthcare facilities will often use facility-specific items, such as, but not limited to, specific uniforms, specific ID badges or asset tags, specific bedding, specific signage, and other types of specific objects. Attribute data for those specific objects is entered into database 50 using one or more user input devices 54 (FIGS. 2-4).

The loading of attributed data 44 into database 50 can be accomplished in a variety of different manners. One such manner includes inputting photographs of objects taken from sufficient viewpoints to enable a complete set of size, shape, and color definitions for the object. Such photographs can include dimensional information, or the dimensional information can be added separately (or omitted, in some cases). Another manner of loading the attribute data 44 includes transferring the data from a pre-existing library of object data to database 50. Others manners includes manually measuring dimensions, shapes, and colors of objects and inputting this manually gathered information in database 50 using user input devices 54.

In some embodiments, some or all of attribute data 44 is generated dynamically by one or more persons manually identifying objects that are detected within the fields of view of cameras 22. That is, the person "teaches" system 20 what the objects are that are within the fields of view of cameras 22. This is done by placing objects to be identified in the field of view of one or more cameras 22 and then displaying the image and depth data to the person. The person then identifies to computer device 24 what image data and depth data corresponds to a particular object. This information is entered either through user input devices 54, or one or more user input devices coupled directly to computer device 24 (not shown). This process is repeated for any additional objects that a user wishes to have identified by system 20 that do not include attribute data in database 50. Still other manners of populating database 50 are also possible.

b. Person Data 46

In addition to attribute data 44 regarding objects that are to be identified by system 20, database 50 also stores data that is used by computer device 24 to analyze data from cameras 22 to identify persons who are in the field of view of cameras 22. Such person identification includes both individual identification of people (i.e. the specific names of people) as well as identification of types of people (e.g. nurses, patients, visitors, doctors, technicians, cleaning personnel, etc.). In general, there are three different manners by which system 20 identifies people who are present in the fields of view of cameras 22: (1) facial recognition, (2) visually reading badges or tags worn by the individuals; (3) and/or communicating with an RF ID badge reader positioned in the rooms 28 that detects RF ID badges worn by personnel of the healthcare facility (and/or visitors and patients). Different types of data are stored in database 50 for these different types of person identification.

For facial recognition, database 50 includes a library of facial data for all of the individuals that system 20 is intended to be able to identify. This library includes photographic and/or other physical characteristic information of all of the current caregivers and/or other staff of the patient care facility so that system 20 can compare this information to the image and depth data detected by cameras 22 to identify if a person is a hospital employee and/or who the employee is. Database 50 also contains, in at least some embodiments, photographic data and/or other physical data of the current patients within the patient care facility so that patients can be recognized by system 20.

Database 50 also includes data identifying the badges, tags, wristbands, or other types of indicia that are worn by personnel, patients, and/or visitors to the healthcare facility. These identifying objects may be color coded in certain facilities according to the type of individual, or may have other visually identifiable characteristics that correspond to the type of individual (e.g. doctor, nurse, visitor, patient, etc.). Whatever these visually identifiable characteristics may be, database 50 contains data identifying these characteristics so that computer device 24 can utilize the data to determine the type of individual who is detected wearing one of these objects. In some cases, the objects worn by individuals include the individual's names printed thereon, or other visually detectable information that uniquely identifies the individual. In the former case, computer device 24 includes optical character recognition software that enables it to read the individual's names. In the latter case, database 50 is loaded with information that correlates the visually identifiable information to the specific individual. In either case, database 50 may include, or have access to, the names of all personnel of the healthcare facility and/or patients so that computer device 24 can verify its identification of individuals by checking its identification with these stored names.

Database 50 also includes, in some embodiments where individuals wear RF ID badges, data that correlates the RF ID codes to the individuals' names. In such embodiments, system 20 includes, or is in communication with, one or more RF ID card readers that are positioned in the room 28 being monitored by a particular camera 22, or set of cameras 22. In such embodiments, the RF ID card reader either forwards the RF ID code that it detects on the individual's card to computer device 24, or it translates the code to an individual's name and forward's the individual's name to computer device. In the former case, database 50 includes a table that matches the RF ID codes to individuals. In the latter case, computer device 24 receives the individual's name and does not need to perform additional identification steps.

In still other embodiments, computer device 24 is adapted to utilize additional information that is stored in database 50 when determining the identity of individuals detected by cameras 22. Such additional information includes information identifying uniforms, or types of uniforms, that are worn by specific types of individuals (e.g. nurse, technicians, doctors, etc.). Such additional information may also include information identifying types of gowns that are normally worn by patients of the healthcare facility. Still further, database 50 includes, in at least some embodiments, person identification data that relates to the tasks performed by the individual (e.g. a caregiver who brings in a therapy dog to a patient's room), objects carried or used by the individual (e.g. a doctor who carries a stethoscope); and/or locations where the individual moves in the room (e.g. visitor who sits in a chair next to the patient's bed).

Database 50 also includes, in at least some embodiments, any combination of the aforementioned data used for identifying individuals. Thus, for example, if system 20 is configured to identify individuals by facial recognition, but the individual's face is not pointed toward cameras 22 at a suitable angle for such recognition, computer device 24 additionally analyzes the images and depth data from camera 22 to look for any identifying indicia carried by the individual (e.g. ID badges), analyzes any identification information that it receives from an RF ID card reader (if present), or sends out a message requesting such information from such an RF ID card reader, and/or looks for any task-related, object-related, and/or location-related data that is stored in database 50 that is useful for identifying the individual.

c. Protocol Data 48

Database 50 also includes, in at least some embodiments, protocol data 48 that relates to one or more protocols that are followed by the particular healthcare facility or institution in which system 20 is installed. The specific steps of these protocols may vary from healthcare facility to healthcare facility, as well as the specific protocols themselves. In order to tailor system 20 to the particular protocols that are desired to be followed by a particular healthcare facility, computer device 24 is programmed to allow administrator access to a protocol definition screen or page on one or more displays associated with either computer device 24 or database 50, or both. Such screens allow one or more persons, such as hospital administrators, to enter protocol data 48 into computer device 24 (which forwards the data to database 50) or directly into database 50 regarding the protocols for that particular healthcare facility. The entered data is then used by computer device 24 when analyzing the image and depth data from cameras 22 to determine whether the protocols are being correctly followed and/or for automatically documenting one or more steps of the protocol. This latter feature helps reduce time spent by the healthcare personnel entering data into an EMR, or other system, documenting tasks that they have performed, as will be discussed in greater detail below.

In general, system 20 is configured to perform either or both of two different tasks with respect to the protocols of a healthcare facility. The first one is to determine whether the protocol is being followed properly. The second one is to document and record the individual tasks or steps of the protocol so that the healthcare workers do not need to manually document this information. In the former case, system 20 may also be configured to issue an alert or alarm if a protocol is not being followed properly, and/or to issue reminders to appropriate personnel to take one or more specific steps in order to help ensure that compliance with the protocols is achieved.

Some of the common protocols that system 20 is configured to monitor—whether for compliance purposes or for documentation purposes—include fall prevent protocols; pressure ulcer management/prevention protocols; infection control protocols; therapy protocols (physical, respiratory, etc.); wound/dressing care protocols; ventilator protocols; patient assessment protocols; medication protocols; rounding protocols; sequential compression device protocols; and IV protocols. It will be understood that this list is not exhaustive, and that database 50 can be populated with additional data regarding still other protocols. Further, it will be understood that the protocol data contained within database 50 will vary depending upon which software modules 34 system 20 is equipped with. Indeed, in some embodiments, system 20 may be utilized for purposes other than protocol compliance and/or documentation, in which case database 50 may not include any protocol data.

The specific steps and/or tasks associated with the aforementioned protocols are defined and discussed in greater detail in section D.1 below and therefore need not be repeated here. In general, however, protocol data 48 of database 50 includes sufficient information about the steps and/or tasks of each protocol to be able to identify whether the step took place or not. Thus, as but one example, if a particular healthcare facility has a respiratory therapy protocol that calls for treating a patient with a particular respiratory therapy device, database 50 includes sufficient information to identify the respiratory therapy device. Database 50 also includes sufficient information regarding the amount of time that the device is to be used, and/or the desired frequency of its use. Still further, database 50 includes sufficient data regarding the manner in which the respiratory device is to be used so that computer device 24 can determine from the data from cameras 22 whether or not the device was used and/or used properly. In other words, in at least some embodiments, computer device 24 does not simply detect the presence of the respiratory therapy device and determine that the therapy has been successfully performed, but instead monitors the data from cameras 22 to determine actual usage of the device and/or whether such usage is correctly done.

Thus, for each protocol that is monitored by system 20, database 50 includes protocol data 48 regarding any objects that need to be identified by the protocol, data regarding any steps and/or tasks that are to be performed by part of the protocol, data regarding the frequency and/or timing of any steps of the protocol, data regarding individuals that may be associated with the steps or tasks, and/or any other data that is necessary for computer device 24 to recognize the execution or non-execution of the steps or tasks of the protocol.

d. Environment Data 52

Database 50 also includes environmental data 52. Environmental data 52 includes data that is specific to individual rooms within the facility, such as the layout of the room; the location of pathways, restrooms, closets, electrical outlets, data outlets, and/or other structural items in the room; the dimensions of the room, the location of room doors, suitable or designated locations within the rooms for placing signs, and other useful information. Such environmental data also includes the location, height, and angular orientation of each camera 22 within the room. Such camera information is stored utilizing a three dimensional coordinate frame of reference that is the same as, or that can be correlated to, a coordinate frame of reference in which the locations of the restroom, closets, electrical and data outlets, and other features of the room are defined. In other words, database 50 includes sufficient information about the location of each camera 22 in the room so that computer device 24 can convert depth readings recorded by cameras 22 into known positions within the room.

For example, if a camera 22 detects a siderail of a bed ten feet in front of the camera at a height that is three feet lower than the height of the camera, computer device 24 utilizes the environmental information stored in database 50—such as the location and orientation of the camera 22 within the room—to convert that depth reading into an X, Y, and Z reading of the position of the siderail within the room, where the X, Y, and Z labels refer to the coordinate axes of a three-dimensional room frame of reference.

Computer device 24 utilizes environmental data 52 regarding the position of cameras 22 so that depth and image readings from the multiple cameras can be correlated to each other. Thus, for example, if a first camera detects a first side of an object at a first distance from the first camera, and a second camera detects another side of the object at a second distance from the second camera, the location information of each camera 22 within the room is utilized by computer device 24 to confirm that the first and second cameras 22 are looking at the same object, but from different vantage points. The color, shape, and size information that each camera 22 gathers about the object from its vantage point is then combined by computer device 24, thereby providing computer device 24 with more information for identifying the object and/or for monitoring any activities that relate to the object.

The environmental data 52 stored in database 50 also includes, in at least some embodiments, the specific room that each camera 22 is located in within the healthcare facility. In healthcare facilities having rooms that are shared by multiple patients, database 50 includes information identifying the different bed bays, or other locations, that are designated for each patient. This room and/or bed bay information is used by system 20 when sending messages, including alerts and/or reminders, regarding the activities and/or events that are monitored by system 20. This room and/or bed bay information is also used when receiving information from other existing systems in the healthcare facility. For example, many healthcare facilities utilize an Admission, Discharge, and Tracking (ADT) computer system for keeping track of its patients. Such systems include information that correlates a patient identification with a specific room number and/or bed bay within a multi-person room. In some embodiments, system 20 is adapted to determine the identification of a patient by querying the ADT system for the identification of the patient corresponding to a specific room and/or bay within the room.

In some embodiments, cameras 22 include internal sensors that output signals indicating the zoom level and/or current orientation of the camera. In such embodiments, database 50 includes information that calibrates these zoom level signals and/or orientation signals so that computer device 24 can translate these signals into specific locations or areas of the room 28. In other words, database 50 includes sufficient data about the angular and/or zoom level signals from cameras 22 to enable computer device 24 to match the camera's current field of view to an area or the room defined in the three dimensional coordinate frame of reference of the room. Computer device 24 uses this information to correctly determine the location of objects in the room, even when the zoom level and/or orientation of the camera(s) 22 changes.

Although database 50 has been primarily described herein as being a single, unitary structure, it is to be understood that database 50 can be distributed amongst multiple physical locations and/or integrated into multiple physical objects. For example, in some embodiments, a first portion of database 50 resides in one or more of cameras 22, a second portion resides in computer device 24, a third portion resides in a first server coupled to computer network 30, and a fourth portion resides in a second server coupled to network 30. In still other embodiments, a portion of database 50 resides in one or more of the healthcare facility's existing IT computer devices, which are discussed in greater detail below, and which may include the following: an electronic medical records (EMR) system having at least one EMR computer device 60 (FIGS. 2-4), a work flow management computer device 62, a caregiver alerts computer device 64, an admissions, discharge, and transfer (ADT) computer device 66, (FIG. 2), a nurse call system 68 (FIG. 2), and a patient support apparatus computer device 70. Other distributed layouts of database 50 are also possible. It will therefore be understood that references to database 50 are intended to broadly refer to any collection of electronic memory utilized by computer device 24 and/or cameras 22 in carrying out the functions described herein.

e. Collected Data 56

In addition to storing attribute data 44, person data 46, protocol data 48, and/or environment data 52, database 50 is also configured to store collected data 56 that is collected from cameras 22 and/or any other sensors that are part of system 20. Collected data 56 also includes data that is generated by computer device 24 from the analysis and processing of the image/depth data from cameras 22, as well as the data that is generated by computer device 24 from the analysis and processing of other sensor data.

In order to reduce the capacity of database 50 necessary to store all collected data 56, computer device 24 is configured in at least one embodiment to tag and excerpt relevant data from cameras 22 and compile this tagged and excerpted data into records that are retained for long term storage. The remaining data from cameras 22 that has not been tagged, excerpted, or otherwise designated by computer device 24 as being worthy of storing in a record is discarded. In some embodiments, all collected data 56 is stored for a threshold amount of time (e.g. a day, a week, the entire duration of a patient's stay, etc.) and only after that threshold amount of time has passed does computer device 24 cull from the collected data 56 the selected parts of that data that are to be retained. In general, computer device 24 is configured to identify and save (either permanently or for long-term durations) the collected data 56 that relates to events or activities that are related to any of the activities, protocols, or other things that are being monitored by system 20.

Thus, for example, in one embodiment, computer device 24 is configured with a software module 34 that monitors patient movement in order to prevent and/or mitigate the development of bed sores. That is, the software module 34 monitors the patient to ensure that he or she is moving sufficiently to ensure that the development of bed sores is unlikely and to issue notifications to caregivers if the patient moves insufficiently for more than threshold amount of time. When computer device 24 is configured with this software module, computer device 24 flags all of the image and depth data from cameras 22 that captures patient movement that exceeds one or more threshold levels (e.g. that shifts the patient's weight sufficiently to allow blood flow, or to restrict blood flow, on those areas of the patient's body that are in contact with the mattress, or other support surface). The flagged movement data is time stamped and categorized by computer device 24 as patient movement. In some embodiments, the patient movement is categorized into more precise categories, such as: movement from the patient's back to right or left side, sitting up, sitting down, lifting right or left leg, moving right or left leg, turning head, lifting head, etc.). The image and depth data that is captured between such movement events is not flagged by computer device 24 (or is flagged for future discarding), and is eventually deleted from memory (unless it contains data that is deemed relevant by another software module).

In addition to time and date stamping the data records that are to be retained by system 20, computer device 24 is also configured to stamp the records with additional information, such as the identity of the patient, the room (and/or bay) that the data was generated from, the identity of any caregivers whose images were captured by cameras 22 and are stored in the records, the identity of any objects that are relevant to the recorded task or event and whose images were captured by cameras 22 and stored in the records, and/or other information that is of value to the recorded task or event.

As will be discussed in greater detail below, the data that is marked by computer device 24 for long-term retention may also be sent, either wholly or partially, to one or more other systems for recording as well. Thus, for example, collected data 56 that is generated by system 20 and marked for long-term retention may also be forwarded for entry in an EMR system, or may be sent to a work flow computer system, or to still other types of systems. In some embodiments, computer device 24 deletes the collected data 56 after it has been forwarded to the other system, while in other embodiments, computer device 24 retains the data in database 50 so that a duplicate copy of the data remains.

4. Other Sensors 58

In addition to video cameras 22, computer device 24, and database 50, system 20 is configured in some embodiments to include other sensors 58 (FIG. 2) that are positioned in rooms 28 and that provide additional data that is useful for carrying out the functions described herein. In one embodiment, as discussed above, such additional sensors include a conventional radio frequency identification (RFID) tag reader that is positioned in rooms 28 and that is adapted to read RF ID tags worn by healthcare facility personnel, visitors, and/or patients. When included, the RF ID tag reader forwards identity information (actual identity or information that allows the actual identity to be determined) to computer device 24 of any individuals who are positioned in room 28.

The other sensors 58 also include, in at least some embodiments, one or more temperature sensors for sensing the temperature of room 28, one or more microphones for measuring sounds within the room (ambient noise, patient words or noises, etc.), one or more light sensors for measuring ambient light in room 28, one or more thermal sensors for detecting thermal images, and/or one or more vital sign sensors that detect one or more vital signs of the patient(s) assigned to the room, one or more pressure or force sensors positioned on or within the bed(s), or in other locations, that detect the interface pressures experienced by the patient between the patient and the mattress, or still other types of sensors.

Computer device 24 is programmed to utilize the additional sensor data from sensors 58 in various ways, depending upon which software modules 34 are being executed by computer device 24. Computer device 24 is also configured to store the sensor data it receives from sensors 58 in database 50 as part of the collected data 56 and/or to forward this data to another computer system, such as an EMR system.

In at least one embodiment, sensors 58 include a pressure sensing mat of the types disclosed in commonly-assigned U.S. Pat. No. 8,161,826 issued to Taylor and/or of the types disclosed in commonly-assigned PCT patent application 2012/122002 filed Mar. 2, 2012 by applicant Stryker Corporation and entitled SENSING SYSTEM FOR PATIENT SUPPORTS, the complete disclosures of both of which are incorporated herein by reference. In some embodiments, the readings from these pressure sensing mats are forwarded to computer device 24 and computer device 24 illuminates the patient's body with different colors from a projector 32 according to which regions are experiencing higher pressure, as discussed in more detail with respect to FIG. 12.

In other embodiments, sensors 58 include one or more load cells that are built into one or more patient support apparatuses 36 and that are adapted to detect one or more vital signs of the patient. In at least one of those embodiments, patient support apparatus 36 is constructed in the manner disclosed in commonly-assigned U.S. Pat. No. 7,699,784 issued to Wan Fong et al. and entitled SYSTEM FOR DETECTING AND MONITORING VITAL SIGNS, the complete disclosure of which is hereby incorporated herein by reference.

5. Projectors 32

In some embodiments, system 20 includes one or more light projectors 32 that are positioned within a room 28 or other area of the patient care facility. The projectors 32 are conventional projectors that are capable of projecting images onto a screen, or onto other non-screen surfaces. The images that are projected by projector 32 are controlled by computer device 24, or one or more computers that are in communication with computer device 24. The lighting and/or images that are projected from projectors 32 are used by system 20 to perform one or more of the following tasks: provide images showing healthcare personnel inventory levels of supplies; highlight locations of equipment or supplies within room 28; highlight for a patient which objects in the room 28 are stable to use as a support during ambulation; highlight those objects in the room 28 that are sterile or not sterile; display a real-time pressure map on the patient's body that indicates the interface pressures the patient is currently experiencing; display one or more virtual control panels; and/or to perform other tasks.

6. Interaction with Existing Equipment

As was noted above, video monitoring system 20 is adapted to be installed in healthcare facilities having existing IT equipment and/or systems and to interact and communicate with one or more of such systems. The specific number and types of such systems may vary from healthcare facility to healthcare facility. A typical healthcare facility, however, will include one or more of the following systems: an electronic medical records (EMR) having at least one EMR computer device 60 (FIGS. 2-4), a work flow management computer device 62, a caregiver alerts computer device 64, an admissions, discharge, and transfer (ADT) computer device 66, (FIG. 2), a nurse call system 68 (FIG. 2), a patient support apparatus computer device 70, or any other computer device in communication with network 30.

Any of the computer devices in communication with network 30, such as devices 60, 62, 64, 66, 68, and/or 70 may comprise one or more conventional servers, PCs, software applications, or other known computing devices. For example, in at least one embodiment of system 20, EMR computer device 60 is a conventional computer device or software application adapted to store and process patient electronic medical records. As noted above, in some embodiments of system 20, information gathered from one or more video cameras 22 and processed by computer device 24 is transferred to EMR device 60 such that the processed information is automatically entered into a particular patient's EMR. Such conventional EMR computer devices are available from multiple companies, including, but not limited to, McKesson Corporation of San Francisco, Calif.; Epic Systems Corporation of Verona, Wis.; and others. Computer device 24 is adapted to convert the information gathered from cameras 22 and/or sensors 58 to a protocol that is compatible with the EMR device 60, such as, but not limited to, an HL-7 format.

Work flow computer device 62 is a conventional computer device or software application adapted to manage the assignment of caregivers to particular patients, to oversee the performance of specific caregiver functions, and to manage resources within the hospital environment. Certain information gathered from one or more video cameras 22 and processed by computer device 24 is transferred to work flow computer device 62, thereby avoiding the need for manual entry of such information. Such information includes data identifying the completion, or partial completion, of one or more caregiver tasks. Such information also, or alternatively, includes data that indicates tasks, or partial tasks, that have yet to be competed. Still further, such information includes data regarding the patient occupancy rates of rooms 28, the cleaning status of rooms 28, and other information that is detectable by system 20.

Caregiver alerts computer device 64 is a conventional computer device or software application that is adapted to communicate alerts to caregivers. In some embodiments, computer device 64 is part of a conventional nurse call computer system, while in other embodiments it is completely integrated into such a nurse call computer system. In still other embodiments, it is a stand-alone system separate from the nurse call system. Regardless of its relationship to a nurse call system, caregiver alerts computer device 64 is adapted to forward alerts to caregivers when information about a patient warrants. Such alerts are forwarded wirelessly to portable communication devices carried by the caregivers (e.g. pagers, personal digital assistants, tablet computers, laptop computers, Blackberries, cell phones, etc.), and/or they are forwarded to nurses stations or audio stations within the vicinity of one or more designated caregivers. Such alerts may be based upon a variety of different information, depending upon the software modules that are executed by computer device 24. As some examples, computer device 24 is configurable to execute software modules that provide alerts when a patient is about to exit, or has exited, his or her bed, when a patient is experiencing pain or discomfort, when a patient has fallen, when a patient's bed settings have changed, or when any number of different events or status changes, many of which are discussed below in more detail. In at least one embodiment, caregiver alerts device 64 is part of a commercially available alerting system marketed by Vocera Communications of San Jose, Calif.

ADT computer device 66 is part of a conventional system that manages the admissions, discharges, and transfers of patients within the healthcare facility. ADT computer device 66 contains information regarding the identity of patients and their assigned locations within the healthcare facility. System 20 interacts with ADT computer device 66, in some embodiments, by receiving patient identity information for patients that are detected by cameras 22. In other embodiments, system 20 sends updated patient location information to ADT system when system 20 detects that a patient has been relocated to a different room. Other interactions are also possible. A variety of different vendors provide such ADT systems such as, but not limited to, Epic Systems Corporation of Verona, Wis.

Nurse call computer device 68 is part of a conventional nurse call system that is adapted to allow a patient positioned on a bed within room 28 to summon or communicate with one or more nurses located at other locations within the healthcare facility. Such nurse call systems typically include one or more nurse call outlets 72 that are positioned within rooms 28 and which are adapted to receive nurse call cables from patient support apparatuses 36. Often, the nurse call cable communicates data from the patient support apparatus 36 to the nurse call computer device 68 via a wired connection 74. The data may include a signal from an exit detection system on board the patient support apparatus 36 indicating that the patient has left the support apparatus, or it may include voice data that allows the patient to talk to a remotely positioned nurse. Multiple different vendors provide such nurse call systems such as, but not limited to, Rauland-Borg Corporation of Mount Prospect, Ill.

System 20 interacts with nurse call computer device 68 in different manners. In one embodiment, computer device 24 includes a software module for monitoring when a patient leaves patient support apparatus 36 and/or for detecting when a patient falls within room 28. In such embodiments, computer device 24 is configured to send an alert signal to nurse call computer device 68 when the patient exit and/or fall is detected. System 20 also communicates other alerts to nurse call system 68 in other embodiments.

Patient support apparatus computer device 70 is a commercially available computing device, such as a server, that communicates with patient support apparatuses 36 and receives data from the patient support apparatuses. In the embodiment shown in FIG. 2, patient support apparatuses 36 include a WiFi transceiver that communicates with one or more wireless access points 38 of network 30. This communication link enables patient support apparatuses 36 to communicate data to and from person support apparatus computer device 70. Such data includes a variety of different data regarding the status of the bed and/or the status of the patient, such as, but not limited to: the positions of the siderails of the patient's bed, the status of the bed's brakes, the height of the deck of the bed, whether the an exit detection system of the bed is armed, the weight detected by the bed's scale system, a center of gravity of the patient's current location on the bed, movement of the patient on the bed, and the outputs of any patient sensors that are incorporated into the bed (e.g. any vital sign sensors, position sensors, incontinence sensors, interface pressure sensors, etc.).

When system 20 is in communication with patient support apparatus computer device 70, it treats the data it receives therefrom in the same manner as the data received from the room sensors 58, as discussed above. That is, system 20 uses the data, as appropriate, to carry out the software modules 34 that computer device 24 is executing, and stores the data in records, as appropriate, as part of the collected data 56. In one embodiment, computer device 24 uses the scale data from a scale system of a patient support apparatus 36 as an aid for identifying objects that are placed on the bed. That is, database 50 includes, in some embodiments, weight attribute data that system 20 uses, in addition to the data from cameras 22, to determine the identification of objects that are positioned on patient support apparatus 36. In other embodiments, the uses of the data from patient support apparatus computer device 70 will vary with the functions carried out by the software modules. In general, such uses include monitoring movement of the patient on patient support apparatus 36 and/or monitoring the status of one or more components of the patient support apparatus 36 (e.g. brakes, height, Fowler angle, etc.)

In at least one embodiment, patient support apparatus computer device 70 is a server sold by Stryker Corporation of Kalamazoo, Mich., as part of its Connected Hospital suite of products. Such products include, in addition to patient support apparatus computer device 70, hospital beds that are adapted to communicate via WiFi with the server (i.e. patient support apparatus computer device 70). Patient support apparatus computer device 70 can, of course, take on different forms.

It will be understood by those skilled in the art that the computer devices 60-70 discussed herein are merely illustrative examples of the types of existing IT infrastructure that system 20 is adapted to communicate with. Different system vendors who provide such computer devices may provide systems that integrate one or more of the functions of these systems into computer devices and systems that perform a combination of these functions. Some vendors may also include additional software and/or computer devices that perform one or more of the functions of the EMR, work flow, caregiver alerts, ADT, and nurse call, patient support apparatus computer devices 60-70, and system 20 is configurable to operate with such consolidated systems and/or additional systems.

C. General Functions

System 20 is adapted to perform a number of general functions regardless of which set of software modules 34 are loaded on computer device 24. These general functions include identifying persons, monitoring their movement, identifying their behavior, recognizing faces, blurring faces in facial data stored in database 50 as part of collected data 56, and issuing notifications, alerts, and/or reminders. These general functions are described in more detail below in subsections 1-5.

1. Person Identification and Movement

Figure 5:
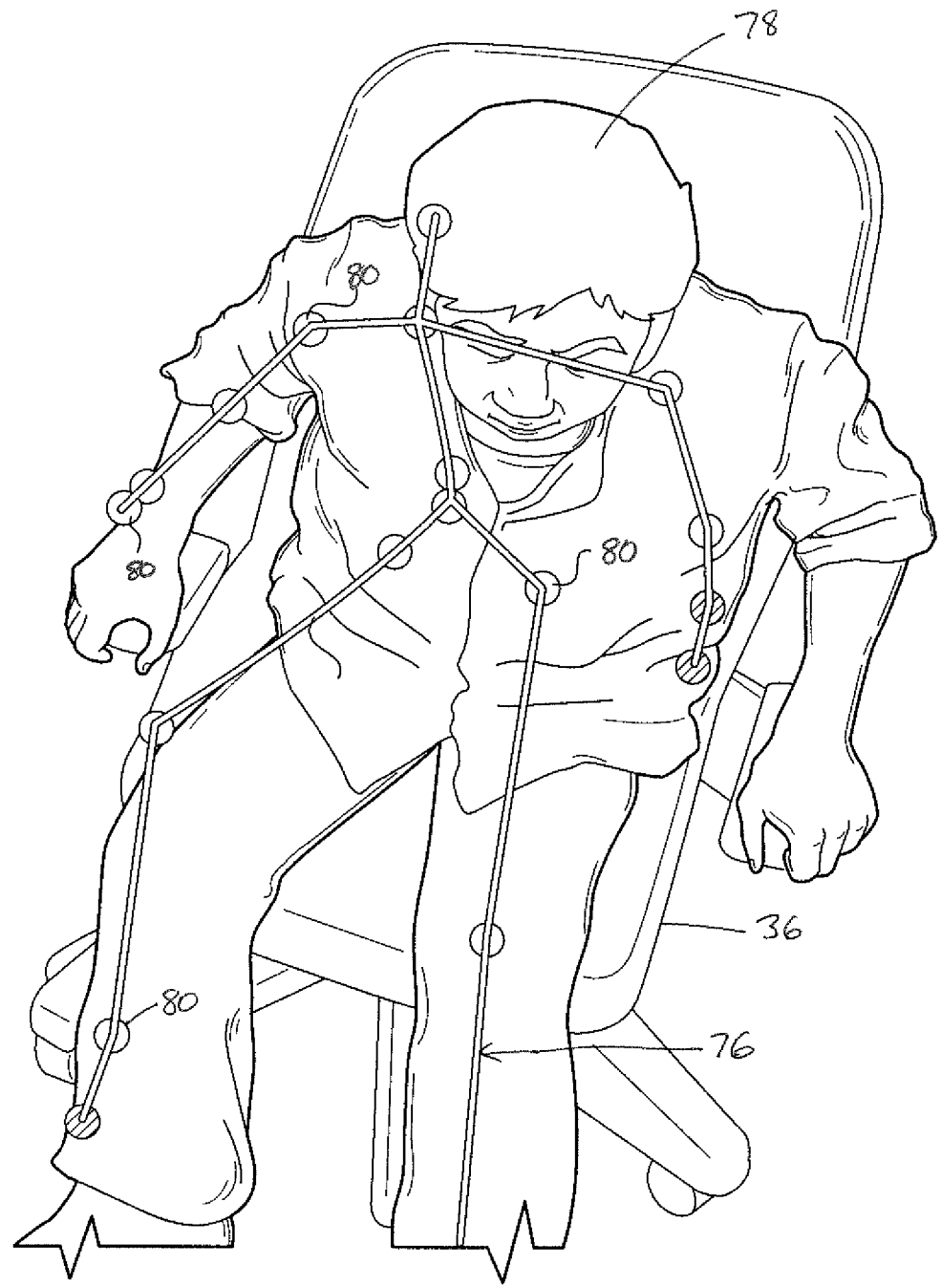
FIG. 5 is a perspective view of a patient seated in a chair shown with a computer-generated skeleton that corresponds to the patient's current position.

Video monitoring system 20 is configured to detect people who appear in the images detected by cameras 22. In at least one embodiment, system 20 detects such people and generates a rudimentary skeleton 76 that corresponds to the current location of each individual detected by cameras 22. FIG. 5 shows one example of such a skeleton 76 superimposed upon an image of an individual 78 detected by one or more cameras 22. In those embodiments where cameras 22 include a Microsoft Kinect device, the detection and generation of skeleton 76 is carried out automatically by software included with the commercially available Microsoft Kinect device. Regardless of the manner in which skeleton 76 is generated, it includes a plurality of points 80 whose three dimensional positions are computed by computer device 24, or any other suitable computational portion of system 20. In those embodiments where cameras 22 include Kinect devices that internally generate skeleton 76, computer device 24 is considered to include those portions of the internal circuitry of the Kinect device itself that perform this skeleton-generating computation. In the embodiment shown in FIG. 5, skeleton 76 includes points 80 that are intended to correspond to the individual's head, neck, shoulders, elbows, wrists, hands, trunk, hips, knees, ankles, and feet. In other embodiments, skeleton 76 includes greater or fewer points 80 corresponding to other portions of a patient's body.

For each point 80 of skeleton 76, system 20 computes the three dimensional position of that point multiple times a second. The knowledge of the position of these points is used to determine various information about the patient, either alone or in combination with the knowledge of other points in the room, as will be discussed in greater detail below. For example, the angle of the patient's trunk (which may be defined as the angle of the line segment connecting a trunk point to a neck point, or in other manners) is usable in an algorithm to determine whether a patient in a chair is leaning toward a side of the chair, and therefore may be at greater risk of a fall. The position of the hands relative to each other and/or relative to the chair also provides an indication of an intent by the patient to get up out of the chair. For example, placing both hands on the armrests and leaning forward is interpreted, in at least one embodiment, by computer device 24 to indicate that the patient is about to stand up. Computer device 24 also interprets images of a patient who places both hands on the same armrest as an indication of an intent by the patient to get up out of the chair. Many other algorithms are described in greater detail below that use the position of body points 80 relative to objects in the room and relative to each other to determine conditions of interest.

Figure 6:
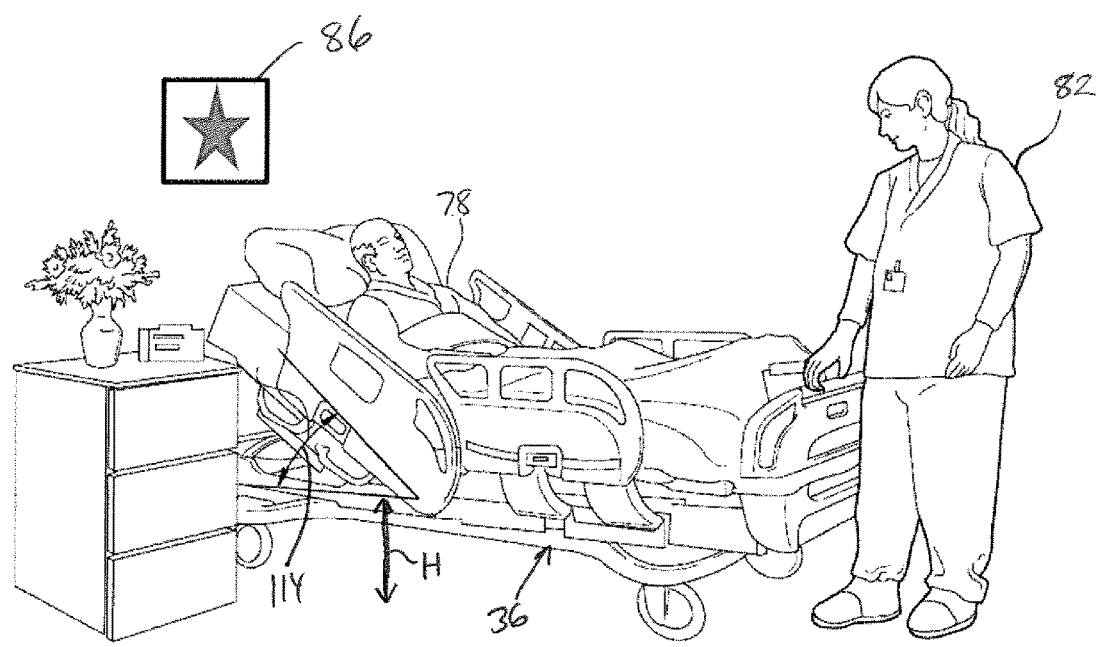
FIG. 6 is a perspective view of an illustrative patient care room, such as a hospital room, images of which are captured and analyzed by the video monitoring systems disclosed herein.

The images and depth readings recorded by cameras 22 are processed to detect when a caregiver enters a room. FIG. 6 shows an example of a caregiver 82. As discussed above, system 20 is configurable to identify this specific caregiver by means of facial recognition software, a badge identification process based upon a specific badge that caregiver 82 is wearing, an RF ID tag that is worn by caregiver 82, the attire of caregiver 82, and/or a combination of one or more of these means.

Figure 7:
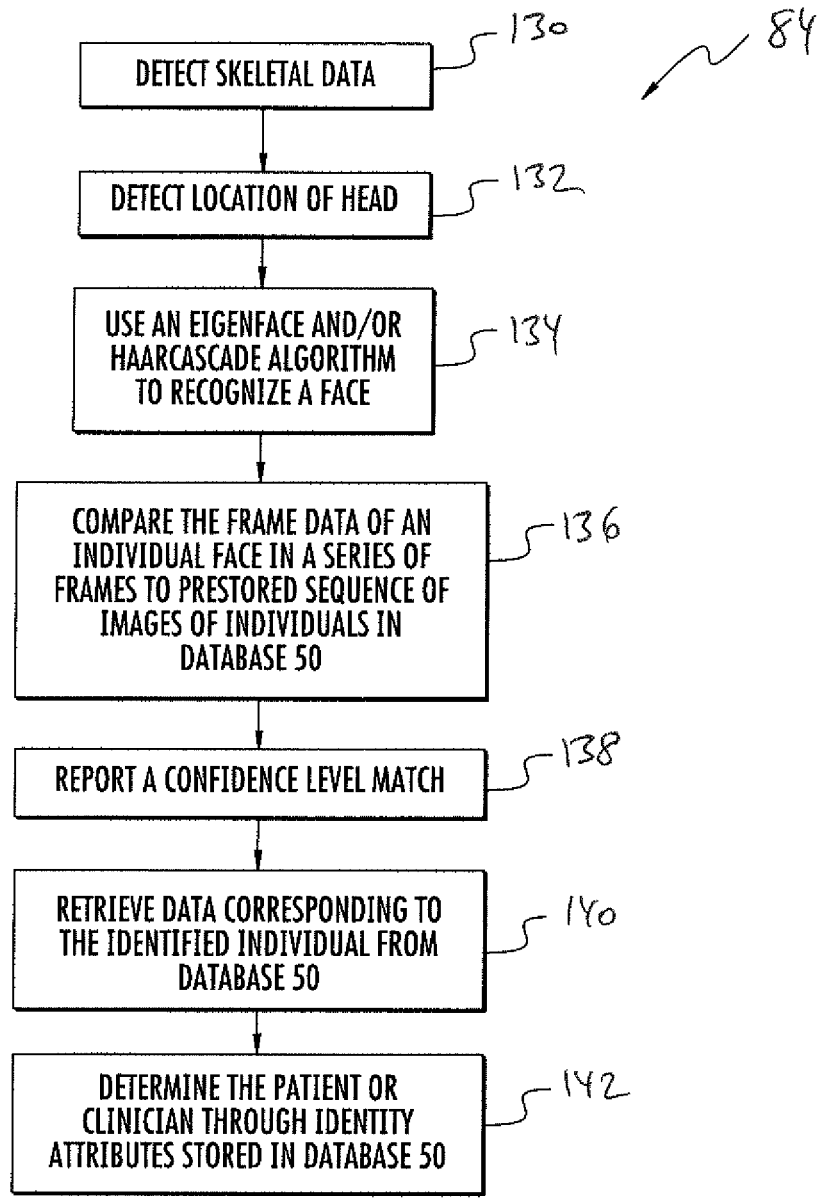
FIG. 7 is a diagram of one example of a face recognition algorithm usable by the video monitoring systems disclosed herein.

One set of steps followed by computer device 24, or any other computing device within system 20, to determine the identity of caregiver 82—or any other individual 78 within the field of view of cameras 22—is a facial detection algorithm 84, which is illustrated in block format in FIG. 7. At step 130 of facial algorithm 84, computer device 24 generates the skeletal data corresponding to caregiver 82 based upon the image and depth data detected by cameras 22. This includes the locations of the points 80 in three dimensional space. At step 132, the detection of the skeletal data is used to identify the location of the head of the caregiver 82. After identifying the head of the caregiver 82, one or more specific facial recognition algorithms are used at step 134 to determine the identity of the caregiver 82. In the algorithm 84 of FIG. 7, both an eigenface and haarcascade algorithm are identified as possible algorithms for identifying a person's face. Other algorithms may be used, either in lieu of, or in addition to, these algorithms.

The steps used by system 20 in recognizing a face at step 134 include the additional steps of selecting the best matching candidate from a database, such as database 50, of potential matches at step 136; reporting a confidence level for this match at step 138, retrieving data about the individual whose face is deemed a match (e.g. name, title, etc.) at step 140; and identifying the caregiver 82 on one or more screens that are in electrical communication with system 20 at step 142. After the caregiver has been identified, the actions undertaken by that caregiver are monitored by system 20, processed and analyzed by computer device 24, and recorded in a manner that correlates those actions to that particular caregiver. That is, computer device 24 recognizes the tasks performed by the caregiver, associates those tasks with that person, documents the completion or non-completion of the tasks, flags the data from cameras 22 (and/or sensors 58) that verifies the completion or non-completion those tasks, and—depending upon the specific software modules loaded on computer device 24—evaluates the actions of the caregiver for compliance or non-compliance with one or more protocols. Computer device 24 also sends the flagged data to database 50 for storage and later review—if desired—by authorized personnel having access to the data stored in database 50. Still further, in some embodiments, computer device 24 forwards the flagged data, pieces of the flagged data, or conclusions drawn by computer device 24 from the flagged data, to one or more other devices, such as EMR computer device 60.

Although this facial recognition process has been described with reference to a caregiver 82, it will be understood that this process is applicable to not just caregivers 82, but any individuals for whom facial data is available in database 50, including, but not limited to, technicians, patients, visitors, janitorial and/or cafeteria workers, clergy, volunteers, etc.

2. Object Recognition

As mentioned above, video monitoring system 20 is also configured to detect and identify objects that appear in the images and depth data gathered from cameras 22. Computer device 24 processes the images and depth data received from cameras 22 to detect the object within one or more image frames. Computer device 24 then seeks to match the three-dimensional pattern of the detected object to the attribute data 44 of a known object that is stored in database 50. If computer device 24 is unable to find a match, it is configured to rotate the object detected in the image frames to different orientations and search through database 50 until a match, if any, can be achieved for one of the rotated orientations. As noted previously in the discussion of database 50, computer device 24 is also configured to compare color data, size data, and other attribute data to the data stored in database 50 to determine if a match can be located. Further, as also noted, the detected data from cameras 22 and/or sensors 58 does not need to provide a 100 percent match to the data in database 50 before computer device 24 determines that a match exists. Instead, computer device 24 is configure to identify an object based upon a detected data that matches stored data by more than a threshold amount, and the threshold can vary in different embodiments.

3. Facial Blurring

Computer device 24 is adapted, in at least one embodiment, to automatically blur those pixels in the images captured by cameras 22 that correspond to an individual's face, such as a patient, in order to protect the individual's identity. In this manner, any images that are recorded and later played back will appear having a blurred-face patient, thereby protecting the patient's identify. Such blurring can even be used, if desired, in situations (described below) where system 20 identifies a patient by facial recognition. In such cases, system 20 uses the unblurred image data to determine the patient's identity through facial recognition, but only stores blurred facial images so that any later playback will show a patient with an anonymous, blurred face. The identification of the patient through facial recognition is then used by computer 24 for associating the data gathered by system 20 to that particular patient, and for determining which medical records certain information should be forwarded to, or for other internal purposes. In this manner, the patient's identify can still be determined, but all visual records of the patient will not carry any visual images that identify the patient to viewers of the visual images.

The blurring is carried out, in at least one embodiment, by utilizing skeleton 76 to detect the location of the patient's head. After the location of the person's head is determined, computer device 24 blurs either an area of a fixed size in the head region, or an area whose size dynamically changes based upon an estimate of how much of the camera 22's field of view is currently being occupied by the patient's head. The unblurred data is either discarded, or is segmented to a separate portion of database 50 having a higher degree of security and/or more restricted access than that associated with the blurred data.

4. Record Keeping

In carrying out any or all of the different functions described herein, system 20 is configured such that cameras 22 are always recording data (visual images and depth information) and analyzing that data. Any of the data that is relevant to any of the general functions carried out by system 20 and/or one or more of the software modules 34 is flagged, time-stamped, and categorized, as discussed previously with respect to database 50. The non-relevant raw data is buffered for some predetermined period of time and electronically discarded thereafter such that the memory resources of the buffer may be reused for recording new image and other data. The flagged data is stored as part of the collected data 56 and stored in database 50.

As was noted previously, in addition to time and date stamping the data records that are to be retained by system 20, computer device 24 is also configured to stamp the records with additional information. The stamping of the data records with this additional information enables relevant data to later be searched and retrieved more easily. The additional data that is stamped and/or appended to the data records includes any one or more of the following: the identity of the patient; the room (and/or bay) that the data was generated from; the identity of any caregivers whose images were captured by cameras 22 and are stored in the records; the identity of any objects that are relevant to the recorded task or event and whose images were captured by cameras 22 and stored in the records; the identity of the protocol that the recorded data is relevant to; the identity of the software module(s) that the recorded is relevant to; the identity of the task and/or event that the recorded data reflects; the identity of the sensors 58 that the data was generated from; and the identity, time, and content of any messages or alerts that were sent or generated by computer device 24 in response to the recorded data.

Among their other purposes, the records that are kept by system 20 provide data for analysis by healthcare practitioners, employees of the healthcare facility, and/or researchers for determining better protocols and performing other studies. For example, the collected data 56 may be made available to pre-approved individuals or entities to allow them to perform data analysis and/or to write their own software apps for either performing their own studies of the data. In some embodiments, system 20 is configured to allow third parties to write and upload their own custom-written software modules for execution by computer device 24. The collected data 56 allows healthcare institutions to study, for example, patient falls or bed sores. The recorded data for all such events within a healthcare facility, or multiple facilities, is aggregated and made available for authorized researchers so that any potential flaws in the corresponding protocols can be rectified, or other additional steps can be taken to reduce or prevent the occurrence of undesirable events or outcomes. Studies may also be performed analyzing the amount of time that is spent on protocols, or other tasks, thereby potentially leading to improved efficiencies for various protocols and/or tasks.

The recorded collected data 56 may also be useful as documentary evidence during litigation. In some instances, the collected data is shared with other healthcare facilities or sent to the patient's home so that the data travels with the patient.

In still other embodiments, computer device 24, or another computer device, analyzes trends in the collected data to determine if response times for certain events are trending upward or downward in a healthcare facility. Upward trends, if of sufficient magnitude, result in notification to appropriate personnel in the healthcare facility. Trends in factors affecting the Hospital Consumer Assessment of Healthcare Providers and Systems (HCAHPS) survey scores are also monitored in at least one embodiment, and notification to appropriate personnel of any significant upward or downward trend in this data is carried out.

5. Notification/Alarming

Whenever computer device 24 analyzes data from cameras 22 and identifies an event, situation, or condition that warrants notification, system 20 sends an appropriate message to a nurse's station, to a alerting device positioned within room 28 (e.g. patient support apparatus 36) and/or to the mobile communication devices carried by nurses. Communication to the nurses' station is accomplished, in one embodiment, by sending the message over network 30 to nurse call computer device 68, which forwards the information to the nurses' station. Communication to an alerting device positioned in room 28, such as patient support apparatus 36, is accomplished in one embodiment by sending a message to patient support apparatus computer device 70, which then forwards the information to a patient support apparatus 36, and the patient support apparatus 36 issues an alarm. Communication to the mobile communication devices carried by nurses is carried out by sending one or more messages to caregiver alerts computer device 64.

In other embodiments, system 20 is configured to send data to a private website for family member's computer access. Such a website allows cameras 22 to be used for remote visiting and/or monitoring. In other words, one or more of the images from the cameras 22 are forwarded to the website such that family members of the patient can see the patient from a remote location. Voice transmission capability from a microphone 58 is included so that voice communication between the patient and the remote family member can take place simultaneously with the transmission of live video.

D. Monitoring Features

Video monitoring system 20 is adapted to provide one or more monitoring functions that fall into one of the seven categories discussed below in subsections 1-7.

1. Protocol Compliance/Documentation

When computer device 24 is equipped with one or more software modules 34 adapted to recognize tasks associated with a particular healthcare facility's patient care protocols, computer device 24 recognizes the relevant tasks, documents the completion or non-completion of the tasks, and in some cases, provides alerting if the tasks are not completed properly or within a requirement time period. When so configured, system 20 helps ensure that the patient care protocols of the healthcare facility are properly followed. In such embodiments, system 20 automatically detects when a caregiver 82 enters the patient's room and monitors the activities performed by the caregiver to ensure that one or more desired activities are performed.

As one example, a hospital's patient care protocol often requires that a patient be turned while positioned on the bed at certain intervals so as to lessen the likelihood of bed sores and/or other medical ailments. System 20 can be equipped with a software module 34 designed for monitoring patient turning protocols that detects the absence or presence of such turning at the required intervals. Another software module 34 can be executed by computer device 24 that determines whether or not the head of the patient's bed (Fowler section) remains positioned at a desired angle. Such a software module 34 is used for lessening the likelihood of ventilator associated pneumonia, as will be discussed in greater detail below. As yet another example, computer device 24 can be loaded with a software module 34 that checks to see if the patient's bed, or other patient support apparatus 36, is at a low height. This is useful for reducing the likelihood of patient falls when getting into or out of the bed, and may be part of a healthcare facility's patient fall prevention protocol.

As will be discussed in greater detail below in subsections a-d, computer device 24 is adapted to execute one or more software modules 34 that monitor one or more patient care protocol steps that are associated with any of the following: patient fall prevention, infection control, pressure ulcer management, changing a wound dressing, conducting an assessment of a patient, providing physical or respiratory therapy to a patient, starting a ventilator, and/or applying cardiopulmonary resuscitation (CPR).

a. Fall-Prevention Protocols

Healthcare facilities often have protocols in place that attempt to reduce and/or avoid patient falls within their facility. These protocols may vary from facility to facility, but generally include performing one or more of the following tasks when caring for patients: ensuring that the height of the patient's bed is at its lowest height, or some other height less than a threshold; ensuring that the brakes on the bed are set; moving at least the head end siderails of the bed into a raised position that obstructs the patient from exiting from the head end; arming an exit detection system of the bed so that caregivers are notified when the patient exits the bed, or attempts to exit the bed; ensuring that a nurse call cable and/or power cable are plugged into a nurse call system outlet 72 (FIG. 2) or electrical power outlet, respectively; assessing how high of a fall risk a patient is by performing one or more fall risk assessments (e.g. the Morse fall assessment and/or the Hendrich II assessment); ensuring that obstacles are not in a path between the patient and the restroom, ensuring that an anti-skid mat is positioned adjacent the bed where the patient is likely to exit; providing the patient with anti-skid slippers; ensuring a patient is wearing a helmet, anti-slip socks or slippers; ensuring that items likely to be desired by the patient are within reach (e.g. food, cups, cell phone, telephone, bed pan, nurse call and/or bed control pendant, etc.); and/or providing a visual indication (e.g. sign, bracelet, or badge) near or on the patient indicating that he or she is a fall risk.

System 20 is configured to allow a healthcare administrator to custom tailor a specific fall prevention protocol and enter the requirements (e.g. tasks) into database 50. The customer tailored fall prevention protocol includes any one or more of the above-identified tasks associated with preventing falls. In addition, in at least some embodiments, system 20 is adapted to allow the hospital administrator to define additional tasks beyond those identified above.

System 20 is also configured to allow a healthcare administrator to decide when and whether system 20 will monitor the patient fall prevention protocol. For example, in one embodiment, a fall prevention protocol software module 34 is configured to automatically presume that every patient is a fall risk until instructed otherwise by a nurse or other authorized individual. In this embodiment, computer device 24 automatically monitors every patient to determine whether the facility's fall prevention protocol is being followed or not. If it is not, system 20 issues an alert to the caregiver(s) assigned to the patient who is not being cared for in accordance with the fall prevention protocol. If it is, system 20 issues no alerts, but documents the steps that are taken in order to comply with the fall prevention protocol. This monitoring continues until an authorized individual instructs system 20 that the patient is no longer a fall risk, at which point computer device 24 stops monitoring compliance with the fall prevention protocol for that particular patient.

In another embodiment, computer device 24 is equipped with a fall prevention protocol software module 34 that is configured to automatically consult the patient's electronic medical records to see if a fall risk assessment has been performed for that particular patient. This is accomplished by communication with EMR computer device 60. If the fall risk assessment has been done and the result of the assessment is that the patient is considered a fall risk, computer device 24 automatically implements monitoring of the patient's care for compliance with the health care facility's fall prevention protocol. Additionally, if there is no fall risk assessment in the EMR computer device for that particular patient, computer device 24 will also automatically start monitoring the patient's care for compliance with the health care facility's fall prevention protocol. Only if the EMR contains a fall risk assessment indicating that the particular patient is not a fall risk will computer device 24 terminate the monitoring of the patient's care for compliance with the fall prevention protocol. At least one software module 34 for monitoring compliance with the healthcare facility's fall prevention protocol is adapted to send a reminder to the patient's caregiver if the fall prevention assessment is not in the electronic medical records of that patient, thereby encouraging the caregiver to perform the assessment.

Although other fall risk assessments may be used, two common fall risk assessments are the Morse fall risk scale and the Hendrich II fall risk scale. Both of these scales assign numeric values to various risk factors. If the sum of the numeric risk values from all of the factors exceeds a threshold, the patient is considered a risk factor. The Hendrich II fall risk scale factor assigns numeric values to the following risk factors: (1) confusion, disorientation, and/or impulsivity; (2) symptomatic depression; (3) altered elimination; (4) dizziness/vertigo; (5) male gender; (6) any administered anti-epileptic medications; and (7) any administered benzodiazepines. The Morse fall risk scale assigns numeric values to the following risk factors of the patient:

(1) a history of falling; (2) presence of a secondary diagnosis (e.g. more than one diagnosis is listed on the patient's chart); (3) usage of an ambulatory aid (crutches, furniture, cane, walker, etc.); (4) presence of an IV/Heparin lock; (5) presence of a weak or impaired gait; and (6) a reduced mental status (patient forgets own abilities or limitations).

In at least one embodiment, system 20 includes a fall prevention protocol software module 34 that is adapted to automatically determine the numeric value that should be assigned to one or more of the aforementioned fall risk factors from either or both of the Hendrich II or Morse fall risk assessments. Computer device 24 forwards the determined numeric value to EMR computer device 60 for entry into the patient's electronic medical record. In at least one embodiment, computer device 24 is configured to automatically check to see if the patient's EMR already includes a numeric value for the fall risk that computer 24 is assessing. If it does, computer 24 compares the value in the EMR to the value it generated and provides notification to the assigned caregiver if there is a discrepancy (or, in some embodiments, only if the discrepancy exceeds a predetermined threshold). If it does not, computer device 24 enters the numeric value it determined into the patient's EMR. Further, if the numeric value determined by computer device 24, in sum with the other numeric values of the patient's fall risk, raises the overall fall risk of the patient above a threshold (configurable by the healthcare administrator and stored in database 50), computer device 24 automatically begins monitoring of the patient to determine whether the healthcare facility's fall prevention protocol is being followed or not (and issues an alert if it is not).

System 20 is configurable to automatically determine several of the fall risk factors from either or both of the Hendrich II or Morse fall risk assessments. These factors that include the following: (1) whether the patient has a secondary diagnosis; (2) whether the patient has an IV/Heparin lock; (3) whether the patient has a normal, weak, or impaired gait; (4) whether the patient is a male; (5); whether the patient has been administered any anti-epileptic medication; and (6) whether the patient has been administered any benzodiazepines. System 20 automatically determines the appropriate numerical value to assign to risk factors (1), (4), (5), and (6) by interrogating EMR computer device 60 for the patient's EMR, which includes data indicating the appropriate scoring that is to be assigned to these risk factors. Computer device 24 determines the appropriate numerical value for risk factor (2) (IV/Heparin lock) by analyzing the image and depth data from cameras 22 and determining whether or not the patient is currently being administered an IV/Heparin lock.

Computer device 24 determines the appropriate numerical value for risk factor (3) by analyzing the image and depth data from cameras 22 that are captured while the patient walks. That is, the images and data captured by cameras 22 are used by computer device 24 to perform gait assessments on patients. Such gait assessments identify any one or more of the following conditions: a patient's use of the arms of a chair to get up, whether a patient bounces when standing up or exiting his or her bed; whether the patient has a stooped posture, whether the patient's head tilts down, whether the patient uses short and/or shuffled steps, whether the patient grasps nearby furniture/items, etc. Computer device 24 is also configured to analyze the image data to assess a get-up-and-go test administered to the patient in which it is determined whether a patient is able to rise in a single movement, push up in one attempt, or whether multiple attempts are made before successfully rising.

The gait assessment performed by computer device 24 also utilizes comparisons of the locations of the patient's feet relative to the patient's trunk and/or other areas. For example, the horizontal coordinates of the patient's feet are determined by computer device 24 from data provided by cameras 22 (including depth data). The position of the patient's feet is compared to a downward vertical projection of the trunk. If the patient's feet are outside of this downward vertical projection, this provides an indication of an unstable gait. Further, if the vertical coordinates of the patient's feet are above ground for more than minimal amounts of time, this also provides an indication of an unstable gait. Computer device 24 is adapted to alert the patient's caregiver of these indications of an unstable gait and/or to automatically enter them into the patient's EMR.

In some cases, the evaluation of the patient's gait is carried out at the same time a caregiver is assessing the patient's gait. The analysis performed by system 20 provides a more objective assessment of the patient's gait than that which may be performed manually by a caregiver. By providing the caregiver with the results of computer device 24's analysis of the patient's gait, the caregiver can determine whether to designate the patient as a fall risk or not. In other embodiments, if there is a discrepancy between computer device 24's analysis of the patient's gait and the caregiver's analysis, computer device 24 is configured to automatically score the patient's gait with the numeric value that represent the higher fall risk. As noted, if that value causes the overall fall risk assessment to exceed a threshold, system 20 is configured, in some embodiments, to automatically commence monitoring of the patient's care to document and/or determine whether the healthcare facility's fall prevention protocol is being followed or not.

In determining whether a fall prevention protocol is being followed correctly and/or in documenting its compliance or non-compliance, system 20 is configured to detect one or more of the following conditions by communicating with the patient's bed (i.e. patient support apparatus 36): the height of the bed; whether the bed's brakes are on or not; whether and which ones of the bed's siderails are up; and whether the bed's exit detection system is armed or not. In determining whether the fall prevention protocol is being followed correctly and/or in documenting its compliance or non-compliance, system 20 is configured to detect one or more of the following conditions by analyzing the image and depth data from cameras 22: whether any obstacles are present between the patient and the restroom or doorway for exiting room 28; whether the bed's power cable and/or nurse call cable is plugged into the appropriate outlet; whether an anti-skid mat is present; whether the patient has anti-skid slippers and/or sock; whether certain items are within reach of the patient; and whether a sign, bracelet, or badge is present that indicates that the patient is considered a fall risk. Further, as will be discussed in greater detail below, in some embodiments, computer device 24 is adapted to also or alternatively determine any of the following by analyzing the image and depth data from cameras 22: the height of the bed; whether the bed's brakes are on or not; whether and which ones of the bed's siderails are up; and whether the bed's exit detection system is armed or not. Further explanation of how computer device 24 determines several of these conditions is provided below.

When system 20 is configured to monitor and analyze the paths between the patient's bed and the restroom (and/or doorway out of room 28), computer device 24 performs an image and depth analysis of the room in which the patient is positioned to identify if any obstacles are present that may lead to an increased fall risk. The pathway(s) monitored by computer device 24 are defined in database 50 and, as noted previously, can be input by a healthcare administrator using a keyboard, mouse, display, or other items, coupled to database 50. System 20 allows the healthcare administrator to select what specific areas need to be clear of objects/obstacles for a particular patient and/or a particular room.

The selected pathways are defined in three dimensional space on a defined floor plan of the room 28 and stored database 50. Computer device 24 analyzes the outputs from cameras 22 to see if any objects are in that defined area and issues an alert if any are located. In performing this analysis, computer device 24 may also have access to a baseline height of the floor (stored in database 50) and compare this baseline height to the height values it calculates from the depth readings it receives from cameras 22. If computer device 24 detects any significant variations between its height reading and the baseline floor value, it determines that an obstacle exists and issues an alert.

If it is part of the particular healthcare institution's fall prevention protocol, computer device 24 also checks to see if a floor mat is in the right location. This is performed by comparisons of the floor mat attribute data 44 stored in database 50 to the data from cameras 22. Computer device 24 analyzes the data from cameras 22 for objects that are located on the floor, have essentially zero height, and that have the color, shape, and/or size of the floor mat. If located, computer device 24 makes an entry that the floor mat is present and records this information as evidence of compliance with the protocol. If no floor mat is detected, or it is detected in the wrong location, computer device 24 issues an alert, and also makes an entry that the floor mat is either absent or in the wrong location.

When system 20 is configured to monitor for spills on the floor, computer device 24 gathers baseline images of the floor from the data from cameras 22. These images are gathered at periodic intervals and compared to each other. These subsequently captured images may be converted to grayscale images prior to comparison. If an area of the compared images shows a discoloration or color change at an area on the floor that has essentially zero height, and that does not have a size, shape, and/or color of a floor mat, computer device 24 identifies this as a spill and issues an alert. If a spill is detected based upon this comparison, the contours of the spill are detected and monitored.

When system 20 is configured to monitor whether or not the bed's power cable and/or nurse/call cable is plugged into the appropriate outlet, computer device 24 first identifies the bed (person support apparatus 36). Computer device 24 further consults database 50 to determine where on the bed the power cable and/or the nurse call cable connect to the bed. Computer device 24 then analyzes the data from cameras 22 to determine if one or both of these cables are connected to the bed at these locations. If they are, computer device 24 then analyzes the data from cameras 22 to determine if the other ends of the cables are coupled to outlets on one or more of the walls. In making this comparison, computer device 24, in some embodiments, consults data in database 50 that indicates the location of nurse call outlet 72 in that particular room 28, as well as data indicating the locations of the A/C power outlets in that particular room. If the detected cables end at these particular locations, as detected by cameras 22, computer device 24 notes that the cables are properly plugged in, documents this in a record stored as part of collected data 56, and does not issue an alert. If the detected cable ends terminate on the floor, or at some other location other than their corresponding outlet, computer device 24 issues an alert and documents this in the record as part of the collected data 56.

When system 20 is configured to monitor whether or not the patient has anti-skid slippers and/or socks, computer device 24 consults the attribute data 44 stored in database 50 corresponding to the anti-skid slippers and/or socks. Computer device 24 further analyzes the data from cameras 22 to determine the location of the patient's feet. Once the feet are identified, computer device 24 compares the data from cameras 22 gathered at the location of the patient's feet and compares this to the attribute data 44 corresponding to the slippers or socks. If a match is found, computer device 24 documents this in a record stored as part of collected data 56, and does not issue an alert. If no match is found, computer device 24 issues an alert and documents this in the record as part of the collected data 56.

When system 20 is configured to monitor whether or not visual indicators are present, such as a sign 86 (FIG. 6), that indicate that the patient is a fall risk, computer device 24 consults the attribute data 44 stored in database 50 corresponding to the visual indicator. Computer device 24 further analyzes the data from cameras 22 to determine whether the visual indicator is in its expected location (e.g. on the patient's wrist, on a specified portion of the wall, etc.). If it is, computer device 24 documents this in a record stored as part of collected data 56, and does not issue an alert. If it is not in the expected location, or not present at all, computer device 24 issues an alert and documents this in the record as part of the collected data 56.

When system 20 is configured to monitor whether or not certain items are within reach of the patient, computer device 24 analyzes the data from cameras 22 to detect the presence of any such items. As noted, such items include, but are not limited to, such things as a pillow, blanket, phone, OBT, drink, walker, book, or other objects that a patient is likely to have a desire for. When any such items are identified by computer device 24, computer device 24 computes the distance between those items and the torsos of the patient. If this distance exceeds a threshold distance (which can vary from embodiment to embodiment, or in some cases, it can be based on the person's height, as determined from EMR device 60), computer device 24 issues an alert so that a caregiver can move the objects closer to the patient, thereby reducing the likelihood that a patient may move out of the bed in order to retrieve such objects. If this distance does not exceed the threshold distance, computer device 24 documents this in a record stored as part of collected data 56, and does not issue an alert.

As noted, in some embodiments, computer device 24 is configured to determine any one or more of the following conditions based upon information received from patient support apparatus computer device 70: whether the bed is at its lowest height; whether the bed's brakes are on or not; whether and which ones of the bed's siderails are up; and/or whether the bed's exit detection system is armed or not. Additionally, or alternatively, computer device 24 is configured to determine any one or more of these conditions by analyzing the image and depth data from cameras 22. The manners in which computer device 24 determines one or more of these conditions is discussed in greater detail below. Regardless of the manners in which these conditions are determined, at least one software module 34 executed by computer device 24 is configured to transmit a reminder message to the caregiver if the caregiver exits the room 28 without moving the bed to meet these conditions (e.g. move the bed to its lowest height, turn on the brake, raise the siderails, and arm the detection system). As least one software module 34 is also adapted to automatically activate the brake of the patient support apparatus 36 if the caregiver exits the room of a patient without activating the brake.

In some systems 20, one or more cameras 22 are positioned to measure a height H (FIG. 6) of the patient's bed. System 20 identifies the particular type of bed the patient is resting on by detecting a number of attributes of the bed via cameras 22 and then comparing these attributes to attribute data 44 of specific types of beds stored in database 50. The list of attributes include dimensions for the detected bed, markings on the bed, structural features of the beds, identifiers positioned on the bed, or other information about the bed that can be used to distinguish the bed from other types of beds that may be present in the health care facility. If only one type of bed is used within the facility, then such comparisons may be omitted.

After a bed is detected by system 20, system 20 determines how high the bed is currently positioned (distance H in FIG. 6) above the ground. This number is then compared with the known minimum height for that particular bed. Such known heights are stored in database 50. Indeed, database 50 contains values of the minimum heights for each type of bed that may be present in the health care facility. System 20 issues an alert if it detects that height H is greater than the known lowest height for that particular bed. In issuing this alert, a tolerance may be included to account for any measurement errors by system 20 so that bed height alerts are not issued in response to inaccurate height measurements by system 20. Sending such alerts helps in preventing patient falls, and/or in minimizing any negative consequences from any falls that might occur.

In some embodiments, system 20 is configured to only send a low bed height alert if the bed isn't at its lowest height and a caregiver is not in the room. Thus, alerts will not be sent if a caregiver is present and adjustments to the bed height are made. If the caregiver exits the room with the bed not returned to its lowest height, however, system 20 issues an alert to remind a caregiver to return the bed to its lowest height. In other embodiments, system 20 is configured to not send any fall prevention alerts when the caregiver is in the room. If, however, the caregiver exits, or approaches exiting the room 28 with one or more tasks of the fall prevention protocol either undone or not done correctly, system 20 issues an alert to that caregiver. In some embodiments, computer device 24 is adapted to automatically send a message to the bed 36 via patient support apparatus computer device 70 to arm the exit detection system of the bed 36 if the caregiver leaves the room without arming the exit detection system of a patient who is at a fall risk, or who is presumed to be a fall risk (e.g. no fall assessment yet completed).

In those embodiments where system 20 is adapted to determine if the siderails of the patient support apparatus 36 are up or down based on an analysis of the data from cameras 22, computer device 24 utilizes attribute data 44 stored for the siderails, which includes the heights of the siderails relative to the support deck of the bed when the siderails are in their up and down positions. Computer device identifies each of the siderails from the image and depth data from cameras 22, calculates their height relative to the deck of bed 36, or some other reference, and determines whether each one is in their raised or lowered orientation. If the orientations of the siderails do not meet the parameters defined according to the fall prevention protocol (e.g., in some embodiment, both of the head end siderails, as well as at least one of the foot end siderails must be in their up position), computer device 24 issues an alert so that a caregiver can rectify the siderail positions. If the siderails are in their proper orientation, computer device 24 documents this in a record stored as part of collected data 56, and does not issue an alert.

In those embodiments where system 20 is adapted to determine if the brake is on, and/or whether the exit detection system of patient support apparatus 36 is armed or not, computer device 24 is configured, in at least some embodiments, to monitor corresponding lights on the beds that provide an indication of the brake being activated and the exit system being armed. That is, many models of patient support apparatuses 36, such as beds, include lights positioned at defined locations that are illuminated by the bed when the brake is on and when the exit detection system is armed. Attribute data 44 for these beds includes the location and color of these lights for each type of bed 36. Computer device 24 thus checks to see whether the bed's brakes are on and/or the exit detection system is armed, in at least some embodiments, by analyzing the data from cameras 22 to detect whether the corresponding light on the bed is illuminated or not. Some beds 36 also include a similar light that is illuminated when the bed is at its lowest height, and in some embodiments of system 20, computer device 24 is configured to detect whether the bed is at its lowest height or not by looking for the illumination of this light, either additionally or alternatively to measuring the height of the bed.

b. Infection Control Protocols

Healthcare facilities often have protocols in place that attempt to reduce and/or avoid the spread of infection from one person to another (patient-to-patient, caregiver-to-patient, or otherwise). These protocols may vary from facility to facility, but generally include performing one or more of the following tasks when caring for patients: ensuring caregivers wash their hands prior to contacting a patient; maintaining sterile fields and/or keeping track of sterile fields that become potentially contaminated; ensuring caregivers wear appropriate person protection equipment (PPE); detecting potential cross-infection or cross-contamination; and ensuring equipment and rooms are effectively and properly cleaned.

System 20 is configured to allow a healthcare administrator to custom tailor a specific infection control protocol and enter the requirements (e.g. tasks) into database 50. The customer tailored infection control protocol includes any one or more of the above-identified tasks associated with reducing the chances of spreading infections. In addition, in at least some embodiments, system 20 is adapted to allow the hospital administrator to define additional tasks beyond those identified above.

System 20 is also configured to allow a healthcare administrator to decide when and whether system 20 will monitor the infection control protocol. For example, in one embodiment, an infection control protocol software module 34 is configured to automatically presume that every patient is an infection risk until instructed otherwise by a nurse or other authorized individual. In this embodiment, computer device 24 automatically monitors every patient to determine whether the facility's infection control protocol is being followed or not. If it is not, system 20 issues an alert to the caregiver(s) assigned to the patient who is not being cared for in accordance with the infection control protocol. If it is, system 20 issues no alerts, but documents the steps that are taken in order to comply with the protocol. This monitoring continues until an authorized individual instructs system 20 that the patient is no longer an infection risk, whether due to spreading germs or due to receiving germs, at which point computer device 24 stops monitoring compliance with the infection control protocol for that particular patient.

In another embodiment, computer device 24 is equipped with an infection control protocol software module 34 that is configured to automatically consult the patient's electronic medical records to see if the patient has been diagnosed with a contagious malady. This is accomplished by communication with EMR computer device 60. If an infection diagnosis is present, computer device 24 automatically implements monitoring of the patient's care for compliance with the health care facility's infection control protocol.

When executing one example of a software module 34 that implements an infection control protocol, computer device 24 monitors one or more of the following conditions: (1) whether a caregiver has washed his or her hands prior to approaching or touching a patient; (2) whether one or more sterile fields within the room are maintained and/or contaminated; (3) whether personal protection equipment is being used—such as masks, gowns, gloves, and the like—by personnel who enter the room; (4) whether objects within the room are mobile or stationary, and whether an alert should be issued to the appropriate personnel for proper cleaning of the object prior to its leaving and/or entering the room; and (5) whether areas within the room have been properly and/or completely cleaned. Upon the detection of any one or more of these conditions, system 20 documents the condition of compliance and/or non-compliance and forwards appropriate information regarding the condition to appropriate personnel in a manner that will be described in more detail below.

Figure 8:
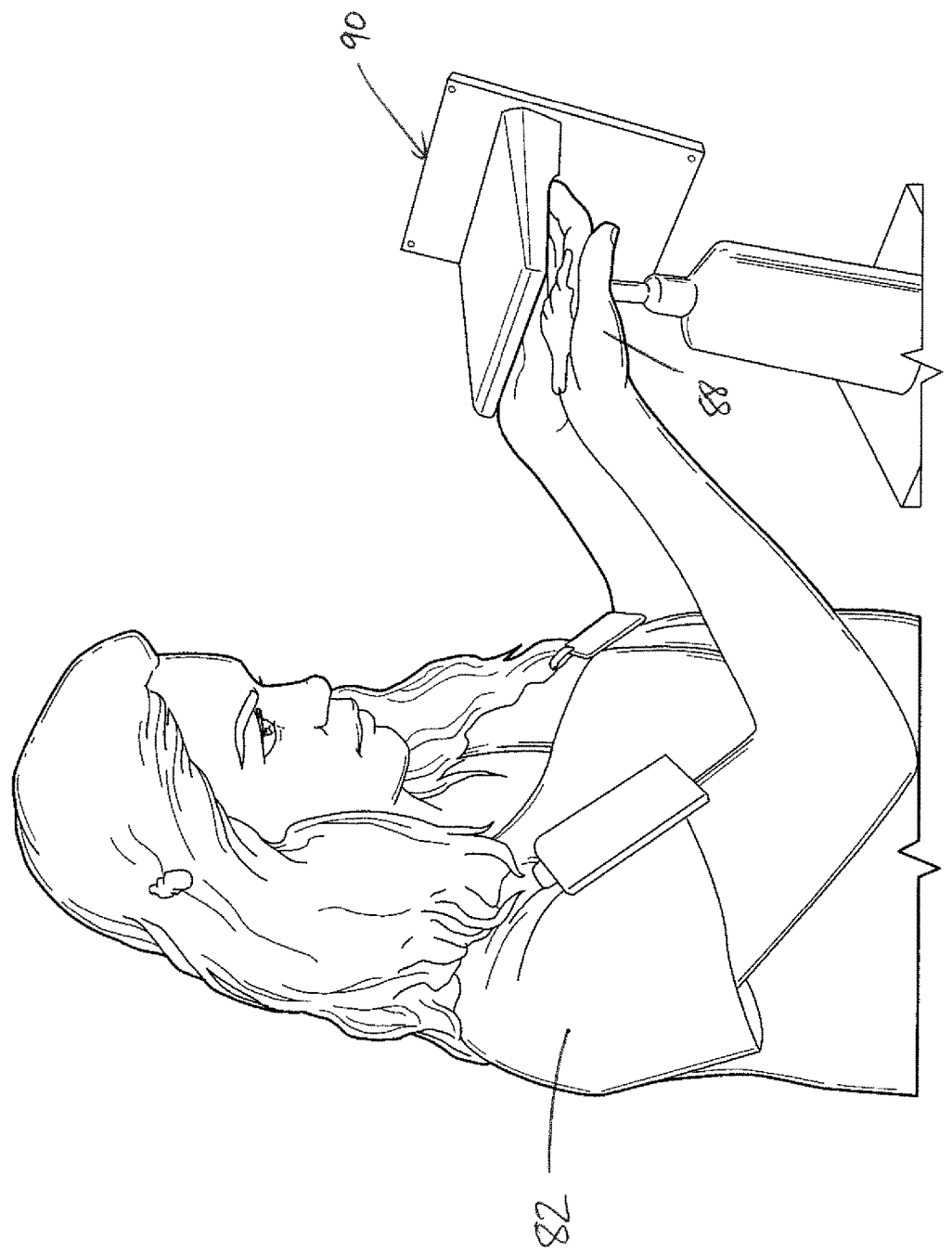
FIG. 8 is a perspective view of a caregiver in the process of sanitizing her hands, images of which are captured and analyzed by the video monitoring systems disclosed herein.

When system 20 is adapted to monitor if a caregiver washes his or her hands prior to approaching a patient, system 20 includes one or more video cameras aimed at a sink, or other hand washing or sanitization station. FIG. 8 provides an example of an image that may be recorded by a camera 22 capturing a caregiver 82 cleaning her hands 88 at a cleaning station 90. Images such as this, which include depth data, are processed by computer device 24 to determine if caregiver 82 has washed his or her hands prior to working with a patient. If system 20 detects that proper hand washing did not take place, the system sends a local alert to remind the caregiver. System 20 also documents the compliance or non-compliance with the hand washing procedures.

In one embodiment, system 20 determines if a caregiver 82 has washed his or her hands by first defining in 3D space an area within the room in which the sink, or other handwashing station 90, is located. This information is stored in database 50 and retrieved therefrom by computer device 24. With knowledge of where the hand washing station 90 is located within a particular room, and/or within a particular camera 22's field of view, computer device 24 identifies individuals who enter the room and determines if they are caregivers or not, such as by using facial recognition algorithm 84, or by other means. If the person is a caregiver, then a hand washing check is triggered. The locations of the caregiver's hands are monitored relative to the 3D space in which the cleaning station 90 is located. Multiple frames are recorded of the caregiver's hands 88 within this space and the time within this space is also recorded. If the amount of time within this space exceeds a preset time, then the hands are considered to have been cleaned. A "hands washed" indication may appear on a screen viewable by health care personnel. The satisfactory washing of the hands is stored, including the underlying data, for later retrieval by authorized personnel in a record of collected data 56. If the caregiver's hands are not washed prior to the caregiver touching an object in the room, an alert and/or reminder is issued by computer device 24.

Figure 9:
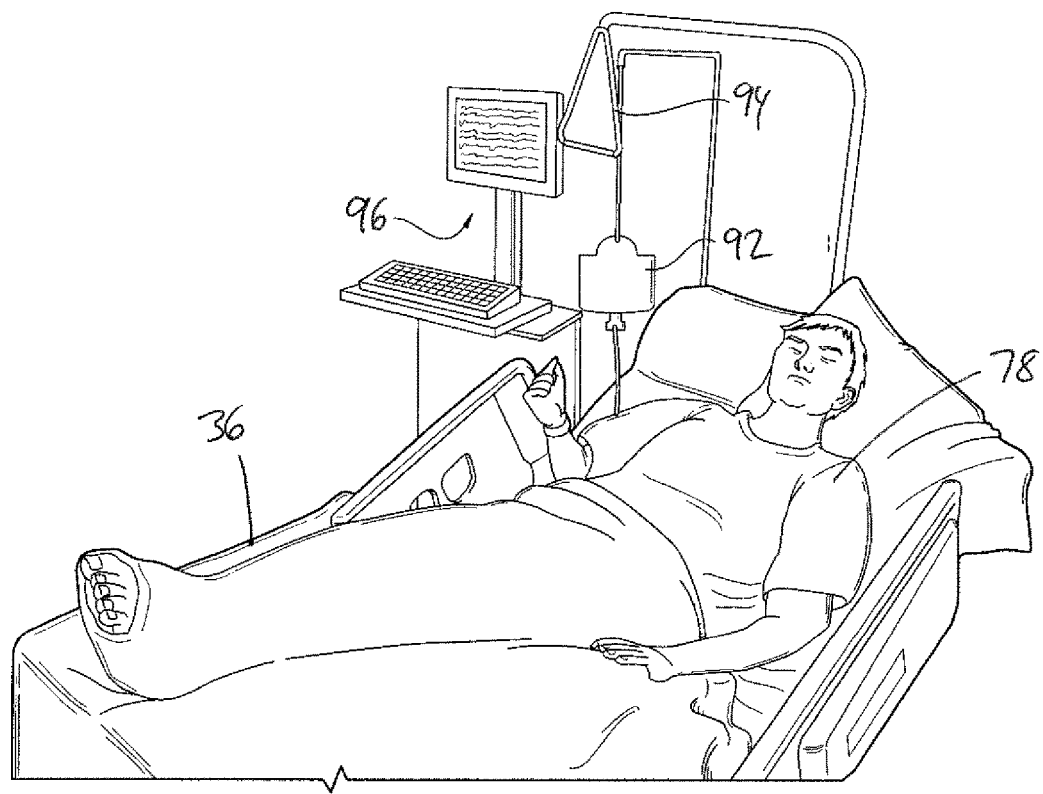
FIG. 9 is a perspective view of a patient in a bed, along with various associated medical equipment, images of which are captured and analyzed by the video monitoring systems disclosed herein.

Cameras 22 are also used to monitor potential contamination of hands after being washed. This includes, in at least one software module 34, recording which objects are touched by a caregiver 82 that are potentially contaminated. Alerts are issued in appropriate circumstances. The recording of what objects are touched in a room includes monitoring any and all objects that are positioned within a room. FIG. 9 illustrates an illustrative example of an image that may be taken by one or more cameras 22 that shows several objects whose contact with a caregiver's hands, or with other objects, is recorded. Such objects include an IV pump 92, an overhead trapeze bar 94, a personal computer 96, etc.

When configured with a corresponding infection control software module 34, system 20 processes images and data from cameras 22 to identify objects and/or packages that are sterile. System 20 further identifies when sterile objects are removed from packaging and monitors what touches the sterile objects once they are removed from the packaging. A local alert is issued to warn the caregiver 82 of potential contamination if it is detected by system 20.

System 20 is also adapted to execute an infection control software module 34 that identifies the location of a patient's dressing or open wound and monitors it such that only sterile objects approach this area. A local alert to warn the caregiver of potential contamination is issued. As with all local alerts discussed herein, the local alert may be visual, audio, or a combination of these. Such alerts may be issued from a display within the room, or from other suitable means.

System 20 is further adapted to execute an infection control software module that monitors the position of a Foley bag associated with a patient. If the Foley bag touches the ground, or comes into contact with any other items within the room, computer device 24 detects this through its analysis of the data from cameras 22 and forwards this information to the appropriate caregivers. Steps to remedy the possible transfer of infectious agents due to this contact with the Foley bag can then be taken. Indeed, at least one software module 34 is configured to, after notifying the caregiver of the Foley bag contact, monitor whether appropriate actions (such as cleaning the area of contact) are taken in response thereto and document those actions, or inactions, as part of the collected data 56.

When configured with a corresponding infection control software module 34, system 20 identifies types of patients with appropriate isolation precautions, such as contact, airborne, etc. In such cases, system 20 detects what kind of personal protection equipment (PPE) the caregiver uses. Local alerts are issued to remind the caregiver if the cameras 22 and computer device 24 detect that proper PPE is not being used. System 20 also tracks compliance with PPE usage. The touching of objects that are potentially contaminated is recorded by system 20.

The detection of glove usage may be accomplished by first determining the location of the caregiver's hands based upon the skeleton 76 data gathered from cameras 22. After this location is determined, raster images of the caregiver's hand regions are gathered via cameras 22. The red, green, and blue (rgb) color values of these raster images is then analyzed. If the color ranges are within a defined zone of colors corresponding to the colors that are expected for gloves, then the caregiver's hands are considered to be gloved. If the colors fall outside the zone, then they are considered ungloved, and an alert is issued.

The detection of a caregiver's gown usage is accomplished in a somewhat similar manner. From the skeletal data gathered by cameras 22, the location of the caregiver's shoulder points or hip joints is determined in three dimensions. A region around these points or joints is defined and a raster image of these regions is gathered. Determining whether a gown is being worn may be accomplished by at least one of two different steps, or a combination of the two. In a first step, the rgb colors of the raster images are compared to a defined range of colors that correspond to the expected colors of a gown (stored in database 50). If the detected colors fall within this range, the caregiver is considered to be wearing a gown. If the detected colors fall outside this range, the caregiver is considered to not be wearing a gown. In a second step, the rgb colors of a first region of the raster images are compared to the rgb colors of another region of the raster images. The two regions are located at spaced locations, such as one near the caregiver's trunk, and another beneath the caregiver's waistline. If the two regions of color are substantially the same, then the caregiver is considered to be wearing a gown.

When configured with a corresponding infection control software module 34, system 20 identifies what objects stay in the room ("stationary objects") versus those objects that leave the room ("mobile objects"), and further monitors potential infection of the "mobile" objects. A local alert is issued to remind a caregiver prior to a "mobile object" leaving the room that the mobile object may be contaminated. Such monitoring is done in conjunction with the monitoring of cleaning (discussed below) such that mobile objects that have been cleaned are permitted to leave the room without generating an alert. The identification of such objects, as with the identification of any of the objects discussed herein, may be accomplished by comparing the detected shape, size, and other attributes of the object with the attribute data 44 of known objects stored in database 50. Alternatively, or in addition, object identification may be accomplished by detecting identifiers positioned on the object, such as badges, bar codes, or other types of detectable indicia.

When configured with a corresponding infection control software module 34, system 20 tracks what areas of the room have been cleaned. Such tracking includes recording what areas of a floor or other surface have been brushed by a broom, mop, cloth, or other cleaning utensil. If areas are missed, a local alert is issued. Additionally, or alternatively, system 20 utilizes one or more projectors 32 to project a specific type of light onto the specific area of the surface that has not been cleaned. The light is displayed only on the area of the surface that has not been cleaned. The area illuminated by the light is altered in substantially real time to match the cleaning being performed. In this manner, any remaining areas that are covered with projected light after the individual finishes cleaning will be highlighted as having been missed, and appropriate corrective cleaning can take place (at which point the projection of light onto those area will terminate).

As another alternative, system 20 is configured in an opposite manner to shine a specific light upon all areas of a surface that have been cleaned. As the cleaner moves the cleaning utensil over the surface, system 20 alters the lighting projected by projector 32 such that the areas that have been cleaned have the specific light projected upon them. Thus, as the person cleans the surface, the areas covered by the specific projected light will keep getting larger and larger. If any spots are missed, the specific projected light will highlight these by the absence of light on those areas. The specific projected light therefore provides a visual cue to the cleaner of where he or she has yet to clean and where he or she has already cleaned.

Figure 10:
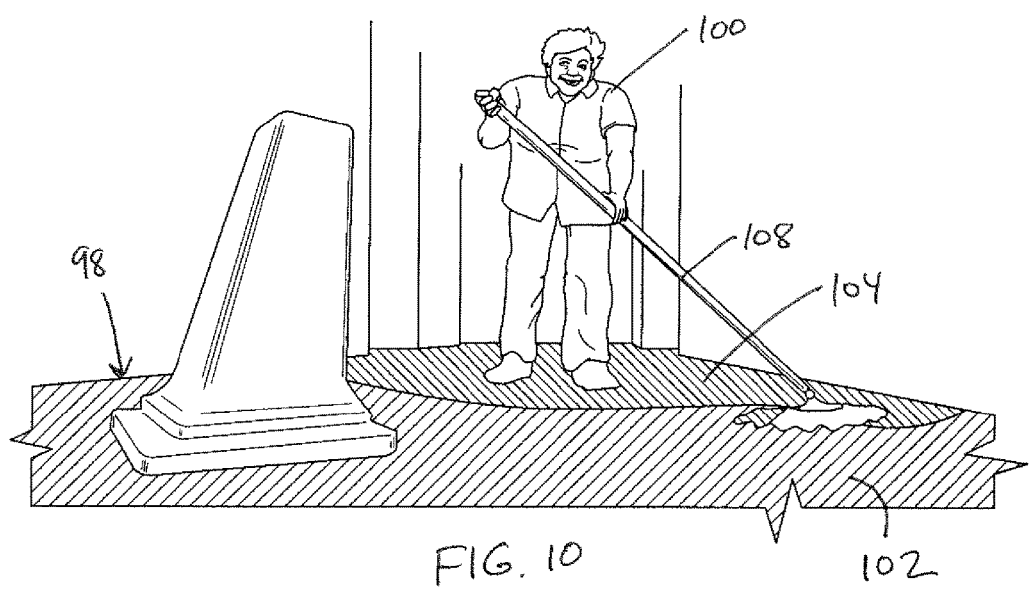
FIG. 10 is a perspective view of a worker cleaning a floor, images of which are captured and analyzed by the video monitoring systems disclosed herein.
Figure 11:
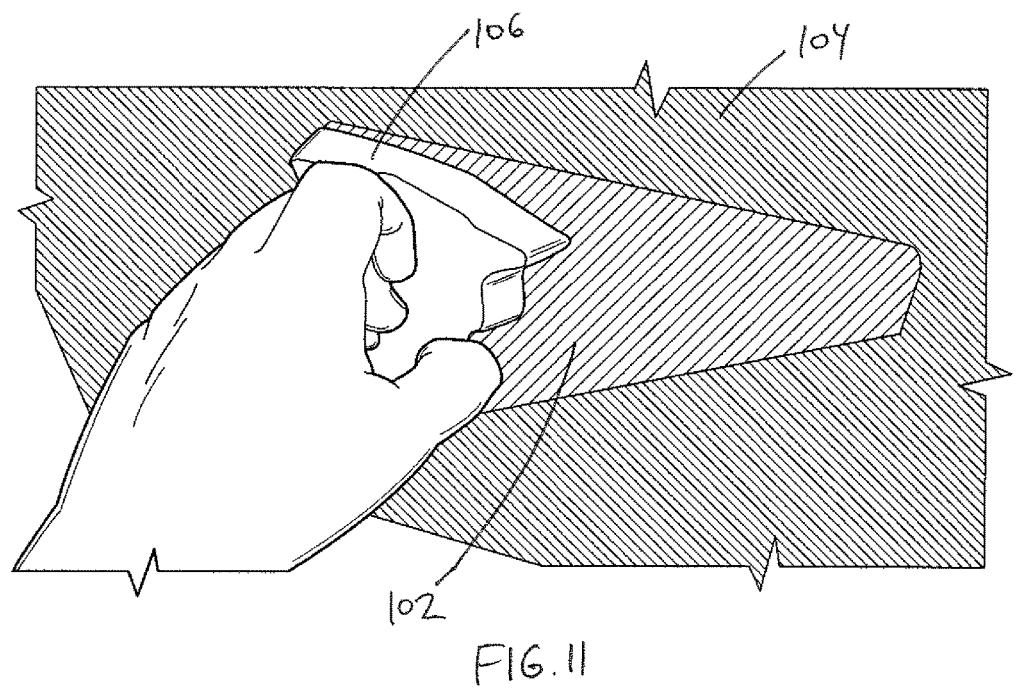
FIG. 11 is a perspective view of a sponge cleaning a surface, images of which are captured and analyzed by the video monitoring systems disclosed herein.

FIGS. 10 and 11 illustrate examples of using this light projection technique. In FIG. 10, the surface to be cleaned is a floor 98. Areas where a cleaner 100 has mopped the floor 98 (cleaned areas 102) have no specific light projected upon them, while areas still to be cleaned (unclean areas 104) have a special light projected upon them. The special light may be a specific color that is easily distinguishable from the background lighting such that the cleaner can distinguish it from the normal overhead lighting that illuminates the room, hallway, or other area. The determination of where to display this light on the surface being cleaned is based upon images taken from one or more cameras 22 and the analysis of those images to determine what areas have been cleaned. This processing and updating of the projected light takes place substantially in real time such that, as the cleaning personnel move their cleaning utensil over the surface, the projected light disappears in the area of the cleaning swath virtually immediately, or within seconds thereafter.

FIG. 11 illustrates a surface of an object being cleaned by a sponge 106. The cleaned areas 102 are not highlighted with specific light projected from projector 32. The uncleaned areas 104 are highlighted with the specific light from projector 32.

System 20 may also tracks what objects/areas have been touched and potentially contaminated since previous cleaning. A display associated with computer device 24 may show if any non-typical areas have been potentially contaminated.

Regardless of whether any light is projected during a cleaning process, system 20 monitors the cleaning process by first identifying individuals who enter a given area who are janitors, or otherwise assigned to perform cleaning tasks. This recognition is done by any of the means previously described, including but not limited to, facial recognition, badge recognition, uniform recognition, combinations of these, or by other methods. Once a cleaning person is identified, system 20 determines the location of a mop 108 (FIG. 10) or other utensil (e.g. sponge 106) held by the cleaning person. The end of the mop, or other cleaning utensil, that is used for cleaning is recognized by comparing the detected data from cameras 22 with stored attribute data 44 corresponding to the cleaning instrument. As the individual performs his or her cleaning, those areas of the floor, or other surface being cleaning, are recorded by cameras 22. If the complete surface area of the floor, or other object, are not cleaned prior to the individual leaving the room, an alert is issued.

In at least one embodiment, system 20 includes a cleaning software module 34—either standalone or as part of an infection control protocol—that is adapted to communicate with a cleaning system such as that disclosed in commonly-assigned U.S. provisional patent application Ser. No. 62/082,687 filed on Nov. 21, 2014 by inventors Micheal Joseph Hayes et al. and entitled SYSTEM AND METHOD OF MANAGING THE CLEANING OF A MEDICAL APPARATUS, the complete disclosure of which is hereby incorporated herein by reference. Such communication includes, in at least one embodiment, forwarding from computer device 24 information regarding which surfaces have been detected by system 20 as having been cleaned, and/or which surfaces remain to be cleaned. System 20 also performs automatic documentation of acceptable or unacceptable cleaning of the surfaces/objects and stores this information as part of the collected data 56 in database 50.

c. Pressure Ulcer Management

Healthcare facilities often have protocols in place that attempt to reduce and/or avoid pressure ulcers developing on patients within their facility. These protocols may vary from facility to facility, but generally include performing one or more of the following tasks when caring for patients: ensuring that a patient is turned at a specified frequency; measuring and/or monitoring patient interface pressures; measuring and/or monitoring patient movement; ensuring the patient's heel remains floating; detecting patient incontinence; and/or detecting foreign objects in the patient's bed.

System 20 is configured to allow a healthcare administrator to custom tailor a specific pressure ulcer management protocol and enter the requirements (e.g. tasks) into database 50. The customer tailored pressure ulcer management protocol includes any one or more of the above-identified tasks associated with preventing falls. In addition, in at least some embodiments, system 20 is adapted to allow the hospital administrator to define additional tasks beyond those identified above.

System 20 is also configured to allow a healthcare administrator to decide when and whether system 20 will monitor the patient pressure ulcer management protocol. For example, in one embodiment, a pressure ulcer management protocol software module 34 is configured to automatically presume that every patient is at risk for bed sores until instructed otherwise by a nurse or other authorized individual. In this embodiment, computer device 24 automatically monitors every patient to determine whether the facility's pressure ulcer management protocol is being followed or not. If it is not, system 20 issues an alert to the caregiver(s) assigned to the patient who is not being cared for in accordance with the pressure ulcer management protocol. If it is, system 20 issues no alerts, but documents the steps that are taken in order to comply with the pressure ulcer management protocol. This monitoring continues until an authorized individual instructs system 20 that the patient is no longer a bed sore risk, at which point computer device 24 stops monitoring compliance with the pressure ulcer management protocol for that particular patient.

In another embodiment, computer device 24 is equipped with a pressure ulcer management protocol software module 34 that is configured to automatically consult the patient's electronic medical records to see if a pressure sore risk assessment has been performed for that particular patient. This is accomplished by communication with EMR computer device 60. If the pressure sore risk assessment has been done and the result of the assessment is that the patient is considered a bed sore risk, computer device 24 automatically implements monitoring of the patient's care for compliance with the health care facility's pressure ulcer management protocol. Additionally, if there is no bed sore risk assessment in the EMR computer device for that particular patient, computer device 24 will also automatically start monitoring the patient's care for compliance with the health care facility's pressure ulcer management protocol. Only if the EMR contains a bed sore risk assessment indicating that the particular patient is not a bed sore risk will computer device 24 terminate the monitoring of the patient's care for compliance with the pressure ulcer management protocol. At least one software module 34 for monitoring compliance with the healthcare facility's pressure ulcer management protocol is adapted to send a reminder to the patient's caregiver if the pressure ulcer management assessment is not in the electronic medical records of that patient, thereby encouraging the caregiver to perform the assessment.

Although other bed sore risk assessments may be used, one common bed sore risk is the Braden Scale for predicting pressure ulcer risk. This scale assigns numeric values to various risk factors. If the sum of the numeric risk values from all of the factors exceeds a threshold, the patient is considered at risk for developing bed sores. More specifically, the Braden scale assigns numeric scores to the following risk factors: (1) patient sensory perception; (2) moisture in contact with the patient; (3) patient activity; (4) patient mobility; (5) patient nutrition; and (6) friction and/or shear experienced by the patient.

In at least one embodiment, system 20 includes a pressure sore management protocol software module 34 that is adapted to automatically determine the numeric value that should be assigned to one or more of the aforementioned risk factors from the Braden scale. Computer device 24 forwards the determined numeric value to EMR computer device 60 for entry into the patient's electronic medical record. In at least one embodiment, computer device 24 is configured to automatically check to see if the patient's EMR already includes a numeric value for the bed sore risk that computer device 24 is assessing. If it does, computer 24 compares the value in the EMR to the value it generated and provides notification to the assigned caregiver if there is a discrepancy. If it does not, computer device 24 enters the numeric value it determined into the patient's EMR. Further, if the numeric value determined by computer device 24, in sum with the other numeric values of the patient's bed sore risk, raises the overall bed sore risk of the patient above a threshold (configurable by the healthcare administrator and stored in database 50), computer device 24 automatically begins monitoring of the patient to determine whether the healthcare facility's pressure ulcer management protocol is being followed or not (and issues an alert if it is not).

Computer device 24 determines the appropriate numerical value for risk factor (2) by communicating with an incontinence sensor (one of in-room sensors 58), and/or by analyzing images of the patient taken by cameras 22 and detecting color changes in the incontinent regions of the patient, and/or by analyzing the outputs of a thermal camera that is able to detect an incontinence event by its thermal characteristics. When detecting incontinence by analyzing data from camera 22 and/or a thermal camera, computer device 24 also determines a size of the color-changed area, or thermal-changed area, to estimate a size of the incontinence event, and uses this information when determining a numeric value to assign to risk factor (2). Computer device 24 determines the appropriate numerical value for risk factor (3) by continually monitoring image and depth data from cameras 22 showing the amount of movement of the patient over time. Based on the level of movement detected, computer device 24 assigns a numeric scale for this risk factor. In some embodiments, computer device 24 is adapted to repetitively re-evaluate this risk factor so that changes in the activity level of the patient can be properly accounted for by either increasing or decreasing the bed sore risk assigned to that patient.

Computer device 24 determines the appropriate numerical value for risk factor (5) by monitoring the foods eaten by the patient and assigning a nutritional value to the eaten foods. In doing so, database 50 includes attribute data 44 for foods served by the healthcare facility that includes nutritional information. Computer device 24 determines which foods are eaten by identifying the foods through analysis of the data from cameras 22 and comparison to attribute data 44. Computer device 24 is also adapted, in at least one embodiment, to monitor the quantity of the foods that are eaten and to take that quantity into consideration when assigning a numeric value to risk factor (5) (nutrition).

In one embodiment, computer device 24 determines the appropriate numerical value for risk factor (6) by communicating with sensor sheet (considered one of sensors 58) positioned underneath the patient that detects the amount of pressure the patient is experiencing at substantially all portions of his or her body. This data is stored and, depending upon how much time a single area experiences pressures at or above a threshold, computer device 24 issues an alert to the patient's caregiver indicating that the patient should be moved to alleviate the high interface pressure areas.

Figure 12:
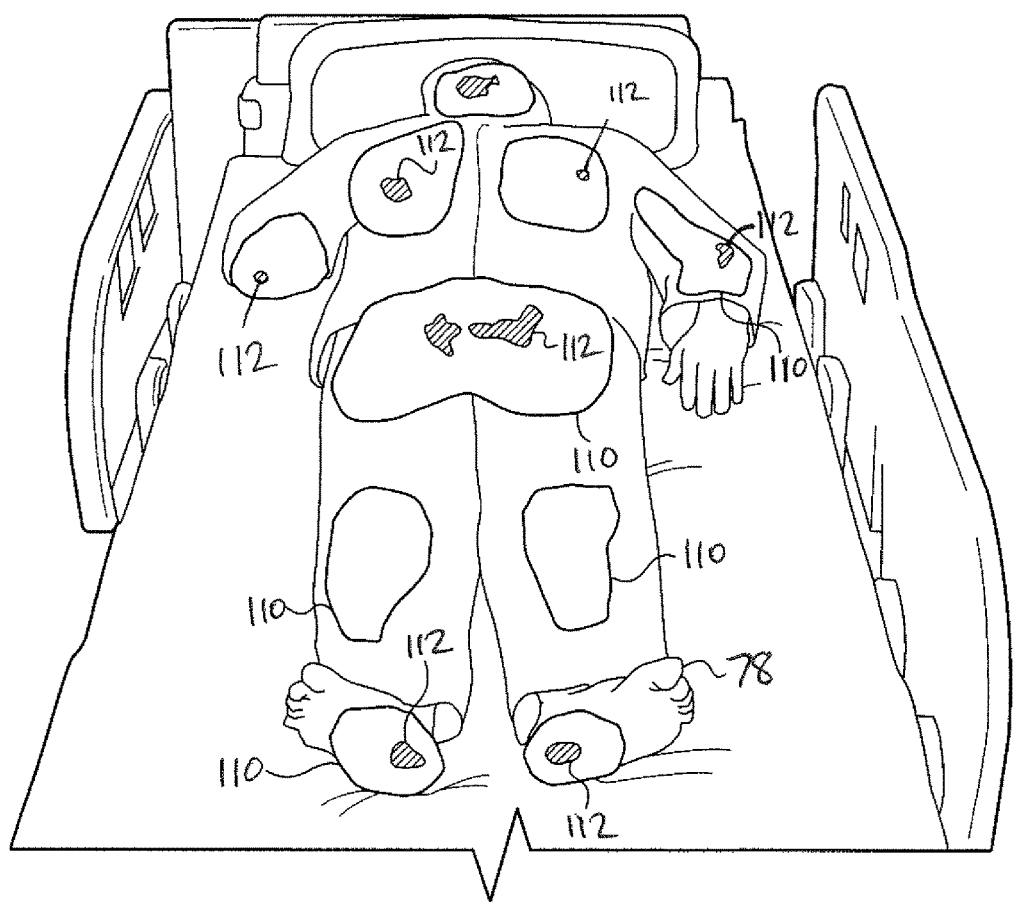
FIG. 12 is a perspective view of a patient wherein a color coded pressure map is projected onto the patient.

In some embodiments, system 20 uses the interface pressure information from the sensor sheet to project patterns of colored light onto the patient's body while he or she is in bed. An example of this is shown in FIG. 12. As can be seen therein, different areas of the patient's body are illuminated in different colors by one or more projectors 32. The color of the light corresponds to the amount of pressure currently being experienced by that portion of the patient's body. For example, first areas 110 in FIG. 12 are coded with a specific color and indicate mild amounts of pressure that the patient is currently experiencing. Second areas 112 are coded with a different color and indicate higher amounts of pressure that are currently being experienced by the patient. Additional color coding may further be used to provide greater granularity of the pressure amounts being experienced. Regardless of the specific number of colors used, a caregiver is provided with a colorized pressure map of the patient that is projected directly onto the patient's body. Those areas experiencing high pressure could then be moved by the caregiver to alleviate the pressure and/or change the location of the pressure, thereby reducing the likelihood of bed sores forming on the patient.

When configured with a corresponding pressure ulcer management software module 34, system 20 detects and documents patient turns, whether performed by a caregiver or by the patients themselves. When system 20 is used to monitor the turning of patients, system 20 identifies—through the processing of data from one or more cameras 22—that the patient is turned and adds a date/time stamp to the data. System 20 then sends the data to EMR computer device 60 and stores data indicative of the turn in database 50. System 20 also identifies what side a patient is on (left, right, back, front) and tracks how long the patient has been on a particular side. System 20 sends an alert to a caregiver if patient has been on a particular side longer than a predetermined time. Such an alert is forwarded to the caregiver by sending a signal to caregiver alert computer device 64, which is programmed to carry out the alerting process.

At least one pressure ulcer management software module 34 is also configured to issue an alert when a foreign object is detected in the patient's bed and the patient subsequently moves on top of the foreign object. Such an alarm is issued because the foreign objects may be hard (e.g. a remote control, a pendant for controlling the bed/entertainment functions, etc.), and when the patient rolls or lies on top of the hard object, the interface pressure between the patient and the hard object is substantially greater than the interface pressure between the patient and the mattress or cushion.

If the patient is diagnosed as a pressure sore risk, at least one pressure ulcer management software module 34 is configured to monitor the heels of the patient and to ensure that they remain floating (i.e. out of contact with the underlying mattress). In such situations, healthcare institutions often insert a cushion, or other device, under the patient's calves to raise the heels out of contact with the underlying surface. In such situations, computer device 24 executes a software module 34 that detects the distance between the heels and the underlying surface and issues an alert if the patient's heels move back into contact with the underlying surface. Alternatively, or additionally, computer device 24 issues an alert and/or a reminder if the caregiver exits the room without inserting the cushion, or other device, under the patient's calves that lift the heels out of contact with the underlying surface.

d. Other Protocols

System 20 is also configurable with one or more software modules 34 that recognize one or more other tasks associated with other protocols. When so configured, system 20 recognizes the completion or non-completion of the task, issues an alert when non-completion is detected, and documents the completion or non-completion in collected data 56. In some cases, documentation of the completion and/or non-completion of the task is also forwarded to EMR computer device 60. Examples of some of the tasks associated with these additional protocols include the following: performing therapy (physical, occupational, respiratory, etc.) on the patient; changing a patient's wound or dressing; performing CPR on a patient; starting a ventilator; performing an assessment on the patient (e.g. Hendrich II, Morse assessment, etc.); ensuring the head angle of the patient's bed is at or above a certain angle; monitoring the hourly (or other time period) rounding of the patient by caregivers; documenting medication administered to the patient; starting or stopping a patient's IV; and operating a sequential compression device on the patient. For each of these tasks, computer device 24 accesses data stored in database 50 that identifies the task, any objects and/or caregivers associated with the tasks, requirements of the task, and any other information needed by computer device 24 to recognize the completion or non-completion of the task.

As one example, when a patient is connected to a ventilator, it is a common healthcare protocol to ensure that the patient's torso remains upright, or angled upwardly beyond a minimum threshold angles. When configured with the appropriate software module 34, computer device 24 is adapted to detect a Fowler angle 114 (FIG. 6), which is the angle the head section of the bed makes with respect to either horizontal or the base of the bed. In some embodiments, system 20 is in communication with one or more additional computers via network 30, such as EMR computer device 60 that send it an indication if a particular patient is supposed to maintain his or her head of bed angle above a specific angle, such as thirty degrees. In other embodiments, computer device 24 processes the data from cameras 22 and detects from those images whether a ventilator is being used with the patient.

Once computer device 24 knows that a ventilator is in use with a patient, computer device 24 monitors the Fowler angle of the bed 36. In one embodiment, this is performed by communicating with patient support apparatus computer device 70, which receives the head angle from the bed 36. In other embodiments, computer device 24 processes the images from cameras 22 to determine the head angle of the bed. If a patient's HOB angle needs to be above, say, 30 degrees, system 20 sends an alert if the HOB angle is lower than this. As with all alerts discussed herein, the alert may include a message sent from computer device 24 to network 30 which is picked up by caregiver alerts computer device 64 for forwarding to the appropriate personnel, or it may be any other type of alert. Such alerts may be useful in helping to prevent ventilator associated pneumonia.

In addition to monitoring the angle of the head of the bed on which the patient is positioned, system 20 also monitors the angle of the patient's trunk, shoulder blades, and/or hips relative to the bed. These angles are desirably measured if there is a chance that the patient is slouching, or otherwise not positioned at an angle in which the patient's trunk is generally aligned with the head of the bed, and therefore the patient's trunk angle does not match the head of bed angle. In such cases, it may be desirable for an alert to be issued such that a caregiver may reposition the patient in a manner in which his or her trunk is elevated so that the chances for ventilator associated pneumonia are reduced.

In summary, system 20 is usable to help ensure that one or more patient care protocols used by a healthcare facility are followed, and/or that the steps associated with one or more of these patient care protocols are automatically documents. Depending upon the condition of the patient, different care protocols may be implemented in order to provide care that is optimally tailored to that patient. System 20 may be used in a variety of different manners for helping to ensure these protocols are properly followed. In some embodiments, system 20 recognizes behaviors of a caregiver and forwards information about that behavior to the appropriate hospital computer or server, such as EMR computer device 60, work flow computer device 62, caregiver alerting computer device 64, or some other computer device. System 20 may also look for fall risk signage amongst the visual images recorded by any of cameras 22 to determine if a patient is at risk for falling, as well as to monitor whether a patient's bed has been put into the proper configuration for that particular patient's medical condition. An alert may also be issued by system 20 if signage is not detected when such signage should be present for a particular patient or for a particular location.

2. Patient Activity Monitoring

In still other embodiments, video monitoring system 20 is used to monitor the patient within the room that may or may not be tied to any particular patient care protocol. In general, such monitoring is performed to keep the caregivers apprised of any information about the patient that is relevant to their treatment, recovery, safety, or other items. Examples of some of such activities include: the entrance of the patient in the room, movement of the patient to the restroom, or exiting of the patient from the room. Other activities that are detectable by system 20 include determining if the patient is eating, sleeping, exiting the bed, walking, having a seizure, falling, getting entrapped in side rails, sitting in a recliner, or experiencing pain. Still other information about the patient may be gathered and processed.

The following activities that are monitored by system 20, when equipped with one or more corresponding software modules 34, are described in conjunction with the identified drawings: exiting the bed (FIG. 13); eating (FIG. 14); walking or walking to the bathroom (no FIG.); having a seizure (no FIG.); falling (no FIG.); getting entrapped in side rails (FIG. 15); sleeping (FIG. 16); experiencing pain (FIG. 17); sitting in a recliner, etc. (no FIG.). Depending upon the particular activity detected, as well as the user-configurable settings associated with the particular software module 34, system 20 sends a message to a remote computer, to a display, or as an alert to a caregiver indicating the commencement or cessation of the activity, or other information about the activity. Further discussion of the detection of several activities is provided below.

a. Patient Support Apparatus Exiting

Figure 13:
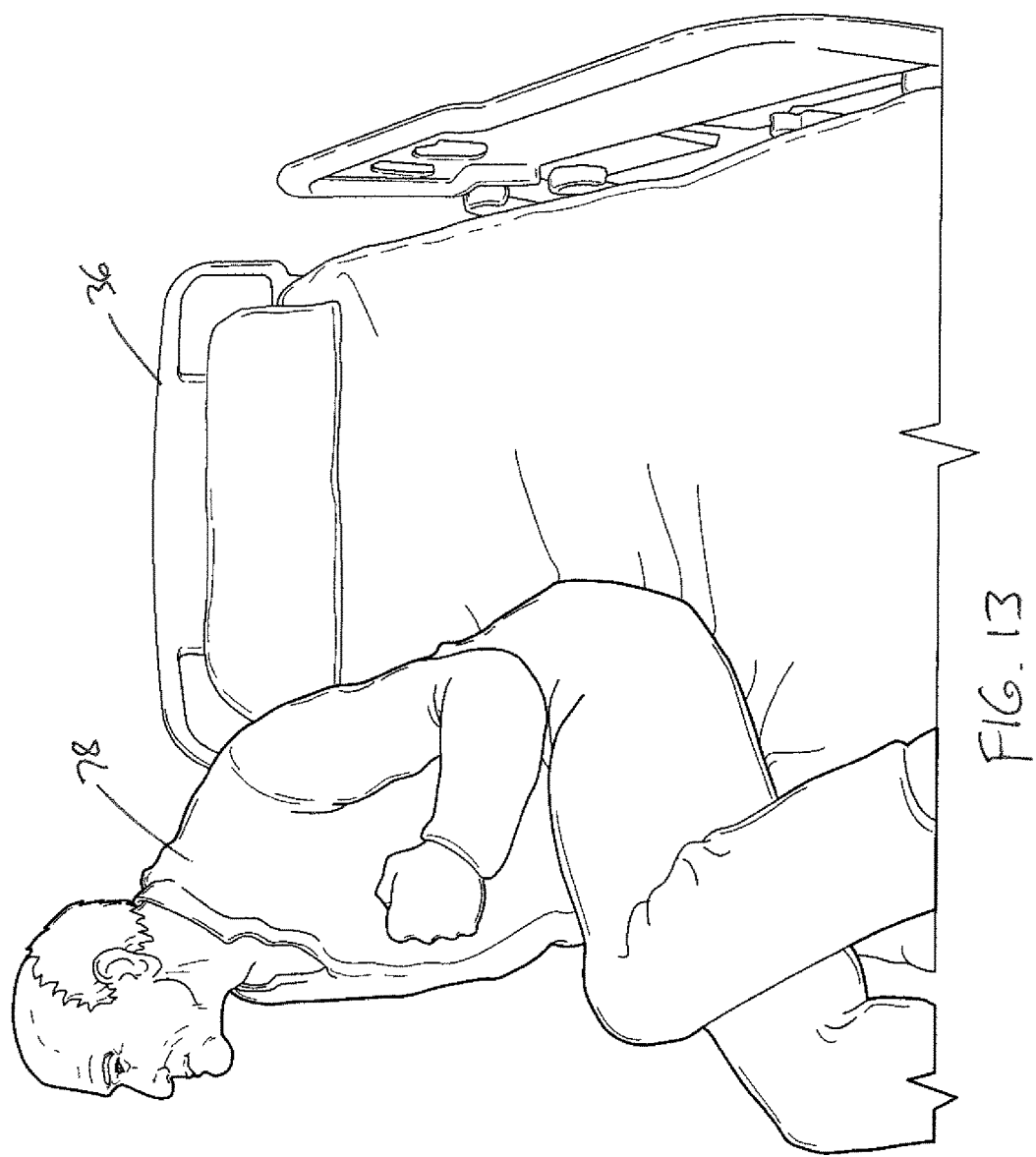
FIG. 13 is a perspective view of a patient about to exit a bed, images of which are captured and analyzed by the video monitoring systems disclosed herein.

In one embodiment, system 20 monitors images and depth readings from cameras 22 to predict behavior that leads to someone getting out of bed. In one embodiment, this also includes recognizing when a patient is awake, as opposed to sleep; recognizing the removal of sheets, or the movement external objects out of the way, such as, but not limited to, an over bed table (OBT), a phone, a nurse call device, etc.); and recognizing when a patient swings his or her legs, grabs a side rail, inches toward a bed edge (such as shown in FIG. 13), lifts his or her torso, finds his or her slippers or other footwear, moves toward a gap between siderails of the patient's bed, or takes other actions.

In one embodiment of system 20, computer device 24 executes a patient exit detection software module 34 that tracks a centroid of the patient 78, or some other reference point of the patient 78, and checks whether the movement of the reference point meets one or more thresholds that trigger a likelihood of the patient exiting. In at least one embodiment, the patient exit detection software module 34 operates in the same manner as any of the exit detection algorithms disclosed in commonly-assigned U.S. patent application Ser. No. 62/065,242 filed Oct. 17, 2014 by inventors Marko N. Kostic et al. and entitled PERSON SUPPORT APPARATUSES WITH MOTION MONITORING, the complete disclosure of which is hereby incorporated herein by reference. In such embodiments, cameras 22 and/or other sensors 58 provide the data that is utilized by the exit detection algorithms, which may be carried out by computer device 24 and/or a computer or controller positioned on-board patient support apparatus 36.

For some patient exit detection software modules, 34, computer device 24 detects when a patient places his or her hands over a side rail. The coordinates of the patient's feet and other body extremities are compared to each other and it is determined whether any of these fall outside the bed outline coordinates. The center of gravity of the patient may also or alternatively be estimated and a higher likelihood of a patent exiting the bed is concluded when the vertical component of the patient's center of gravity increases, or when the vertical component of the position of the patient's head increases. The detection of a patient leaning over a side rail also increases the estimate of the likelihood of a patient leaving the bed. Movement of the patient toward a side rail, or toward the side of the bed closest to the bathroom, also increases the estimate of the likelihood of the patient leaving the bed. The removal of sheets and the sitting up of a patient in bed may also increase this estimate. System 20 calculates a likelihood of a patient making an imminent departure from the bed, based on any of the aforementioned factors. If this estimate exceeds a predefined threshold, then an alert is transmitted to appropriate caregivers. A numeric value corresponding to this estimation of the likelihood of a patient exiting the bed may also be displayed on one or more screens that are viewable by a caregiver, including the screens of mobile devices, such as smart phones, laptops, tablet computers, etc.

The foregoing factors are also used by at least one exit detection software module 34 to estimate the likelihood of a patient exiting a chair. Those factors relating to siderails are replaced with comparable factors relating to the armrests of the chair. An assessment of the likelihood of the patient leaving the chair can also be displayed on one or more screens that are viewable by a caregiver, including the screens of mobile devices, such as smart phones, laptops, tablet computers, etc.

In addition to attempting to prevent a fall, some software modules 34 of system 20 also detect a fall after it occurs. Such detection occurs by way of determining the proximity of a patient's head to the floor, sudden movement of the patient's head, arm movement to catch themselves, or other actions or events. System 20 stores the image data corresponding to a fall as part of collected data 56 for later retrieval and viewing, such as during a post-fall huddle by caregivers, in order to view the events leading up to and after the fall. This provides information that may be useful for modifying the fall prevention protocols in order to prevent future falls, and/or to take other steps to help prevent future falls. In some embodiments, computer device 24 analyzes fall events to make future exit detection and/or fall prevention algorithms more robust.

If an exit event or condition detected by one or more video cameras 22 gives rise to a low risk status, system 20 gives out a warning, according to at least one software module 34. In the case of a high risk status, system 20 issues an alarm. Automatic voice signals may also be transmitted to speakers within the patient's room. Such signals include warning phrases, such as "do you need help?" or "a nurse has been called," or alarm phrases such as "get back in bed, Mr. Johnson" using the patient's name specifically or a beeping sound. Such signals desirably also provide context as to why an alarm is going off. For example, an alarm may state that "you are a fall risk, Mr. Johnson, because you are on medication and just had surgery. Please stay in bed."

Some patient activity software modules 34 executed by computer device 24 are also adapted to turn on the room lights, or a night light, when computer device 24 detects that a patient is about to, or has, exited from patient support apparatus 36. Such software modules 34 are in communication with an ambient light sensor (one of sensors 58), in at least some embodiments, and only perform this automatic illumination function if the room 28 is not already illuminated.

In at least one embodiment of system 20, computer device 24 executes a departure detection software module 34 that is configured to detect four separate events or conditions: (1) that a patient wants to exit from patient support apparatus 36; (2) that a patient is about to exit from the patient support apparatus 36; (3) that the patient has in fact exited and is standing up; and (4) that the patient has fallen. When determining the first condition, computer device 24 analyzes data from cameras 22 to detect the occurrence of one or more of the following factors: the head of the bed has been raised, an over bed table has been moved away from the bed, the sheets or blankets have been removed, the patient has adjusted his or her IV line, the patient has sit up, the patient has grabbed a siderail, and there are no visitors in the room. As any of these factors are detected, computer device 24 calculates an increased probability that the patient is desirous of exiting patient support apparatus 36. When a sufficient number of these factors (which may be differently weighted) are detected, system 20 is configured to send a pre-recorded audio message to the patient (which is played by the speakers on the patient support apparatus 36) that queries the patient about their intention (e.g. "Mr. Jones, do you need a nurse to assist you?").

When determining the second condition, computer device 24 analyzes data from cameras 22 to detect the occurrence of one or more of the following factors: the patient is moving toward a gap in the siderail coverage of the bed, the patient is sitting at the side of the bed, the patient is looking for footwear, the patient is putting footwear on, and/or the patient is leaning forward. As any of these factors are detected, computer device 24 calculates an increased probability that the patient is about to exit the bed (or other person support apparatus 36). When a sufficient number of these factors (which may be differently weighted) are detected, system 20 sends another pre-recorded audio message to the patient that requests the patient to please stay in bed until a caregiver can assist them (e.g. "Mr. Jones, please stay in bed. Do you need a nurse to assist you?").

When determining the third condition, computer device 24 analyzes the data from cameras 22 to detect that the patient is standing up and/or walking. When this condition is detected, computer device 24 sends an alert to the nurse and initiates an alarm. Computer device 24 also sends another pre-recorded audio message to the patient that warns the patient to stay in bed (e.g. "Mr. Jones, please stay in bed. A nurse has been called to assist you.").

When determining the fourth condition, computer device 24 analyzes the data from cameras 22 to detect that the patient has fallen. When a fall is detected, computer device 24 issues an escalated alert and calls all nurses within a specific region close to the fallen patient (e.g. all nurses on that floor, or in that wing). At least one departure detection software module 34 is also configured to provide audio data to the first nurse that enters the room 28 after the patient has fallen, based upon the data gathered from cameras 22 and analyzed by computer device 24. An example of such audio data is the following: "Patent has fallen 37 seconds ago; landed on their left hand and left knee; also hit the front left part of their head; two more nurses are on the way.")

b. Eating

In at least one embodiment of system 20, computer device 24 executes a patient activity software module 34 that determines if a patient is eating, as was previously mentioned. A variety of different algorithms may be used to detect such eating. As one example, an eating detection algorithm followed by computer device 24 first determines the location of the patient's head from the skeletal data. Thereafter, the location of the patient's lips and face are detected in a series of frames captured by cameras 22. For one or more of the frames, the distance between the upper and lower lips is calculated. Variations in this distance over a series of frames are used as an indication that the patient is currently eating. These variations may also, or alternatively, be compared to baseline data stored in database 50 of the distance between the lips of the individual when images of him or her were previously captured during a known eating event.

Figure 14:
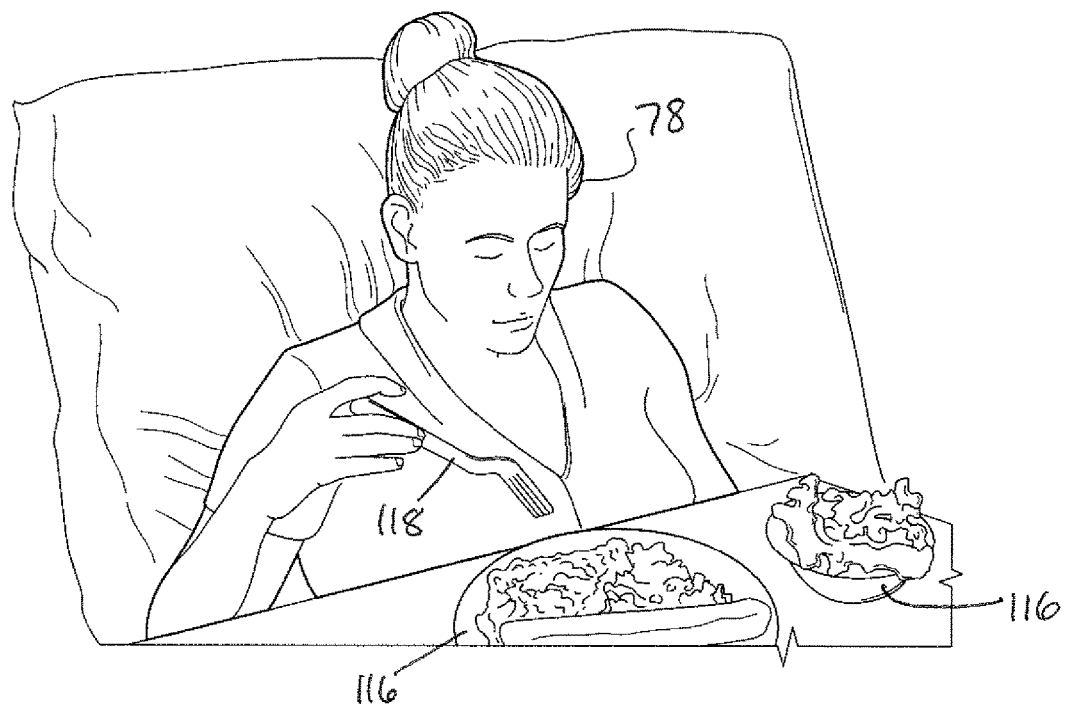
FIG. 14 is a perspective view of a patient eating, images of which are captured and analyzed by the video monitoring systems disclosed herein.

At least one patient activity software module 34 also takes into account, either in lieu of or in addition to the distance between the upper and lower lips, object detection information. Such object detection information includes the detection of a food tray, such as a food tray 116 positioned in the front of the patient and/or a fork 118, or other utensil, positioned in the patient's hand (FIG. 14). Other data that may be used also includes the movement of the patient's arms with respect to the patient's mouth and/or a food tray. Still other data may be used to detect if/when a patient eats.

c. Sleeping

In at least one embodiment of system 20, computer device 24 executes a patient activity software module 34 that determines if a patient is asleep. Such a patient activity software module 34 follows one or more different algorithms to detect a patient's sleeping. For one algorithm, computer device 24 first locates one or both eyes 120 (FIG. 16) on the face of the patient 78 and detects these positions for a series of frames captured by camera(s) 22. Once the positions of the eyes 120 are determined, computer device 24 determines the location of the retinas within the patient's eyes. If the retinas are not visible for a predetermined amount of time and patient movement is substantially absent, computer device 24 determines that the patient is asleep. This information is stored for later retrieval by caregivers, or an alert is issued if there is a desire for immediate notification of the patient falling asleep. The sleep detection algorithm can be modified in an opposite manner to detect if a patient is awake, if desired, and this information may also be stored for later retrieval or transmitted immediately for timely notification to selected personnel.

When computer device 24 is executing a patient activity software module 34 that detects if a patient is awake or asleep, at least one embodiment of the patient activity software module 34 is adapted to automatically change one or more thresholds that are used by other software modules 34 that are being executed by computer device 24. For example, in at least one embodiment, when computer device 24 detects that a patient is asleep, computer device 24 automatically adjusts one or more thresholds that are used by an exit detection algorithm that computer device 24 is also executing. In one such embodiment, the thresholds for triggering an exit detection alert are raised so that the system becomes less sensitive to patient movement while the patient is asleep. Once the patient wakes up, the thresholds are lowered so that the system's sensitivity returns to normal. Still further, in some embodiments, computer device 24 is adapted to adjust the thresholds of the exit detection algorithm based on the time of day. In such embodiments, computer device 24 may lower the thresholds during the night and raise them during the day in order to address the generally greater likelihood of patient falls during the night. Such adjustments are separate from the adjustments made due to the patient being asleep or awake.

Those patient activity software modules 34 that issue an alarm when the patient exits the patient support apparatus 36 are, in at least one embodiment, configured to adapt to other conditions besides the time of day and the sleep/awake state of the patient. For example, in one such embodiment, computer device 24 alters the thresholds used by such a software module such that the trigger for issuing an exit alert is raised when a caregiver, visitor, or other person is present in the room with the patient. System 20 presumes that the other person will be able to assist the patient when he or she exits the person support apparatus 36, and therefore does not issue an exit alert as soon, or as easily, as it would when no additional person is present in the room with the patient.

d. Pain

Figure 17:
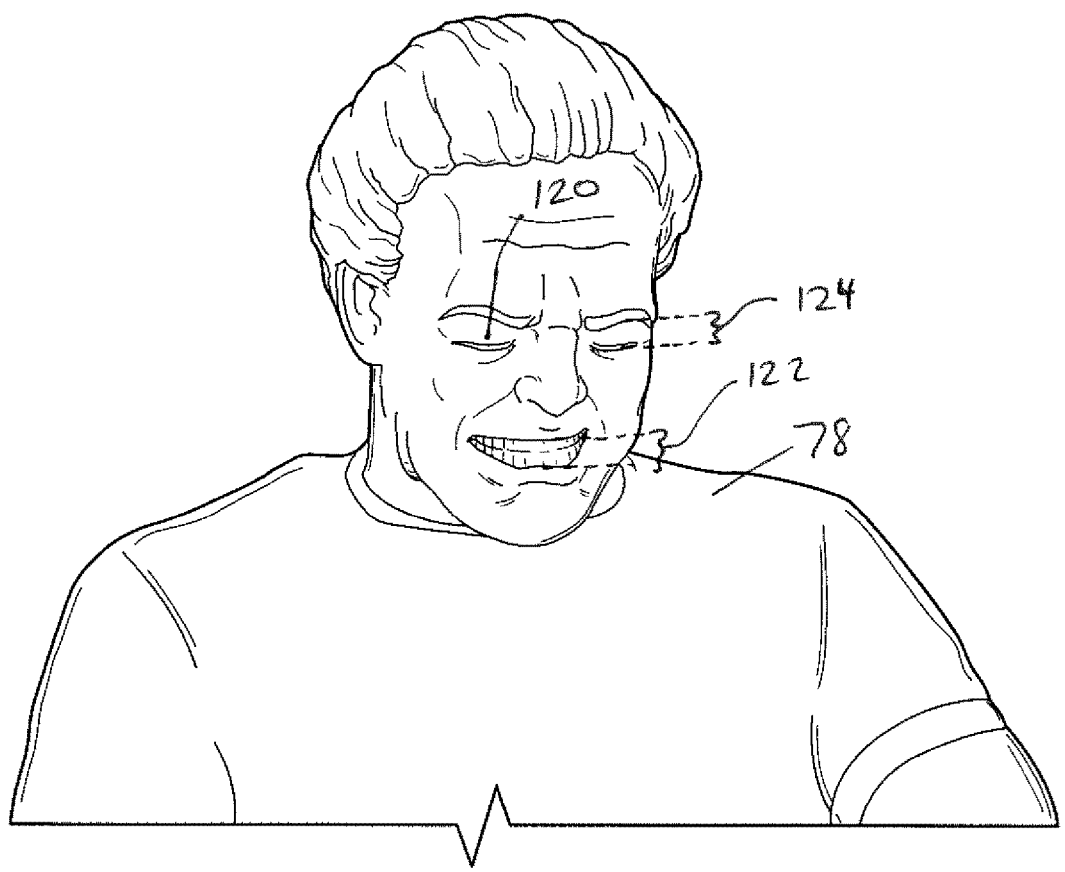
FIG. 17 is a perspective view of a patient experiencing pain, images of which are captured and analyzed by the video monitoring systems disclosed herein.

In at least one embodiment of system 20, computer device 24 executes a patient activity software module 34 that determines if a patient is experiencing pain. When executing such a software module 34, computer device 24 repetitively compares real time images of the patient with a baseline image may over defined time intervals. The baseline image is stored in database 50 are part of person data 46, and may be derived from previous images taken while the patient is in the room, or an admissions photograph, or other sources. The comparisons focus on specific features of the patient's face, such as a distance 122 between the patient's upper and lower lips, a distance 124 between the patient's retina and his or her eyebrows (to detect eyebrow furrowing), and/or sound data detected by cameras 22 that indicates moaning, groaning, or other aural indicia of pain (FIG. 17). If a threshold change in any one or more of these measured factors is met, a pain indication alert is generated by system 20.

e. Entrapment

Figure 15:
FIG. 15 is a perspective view of a patient entrapped against a side rail of a bed, images of which are captured and analyzed by the video monitoring systems disclosed herein.
Figure 16:
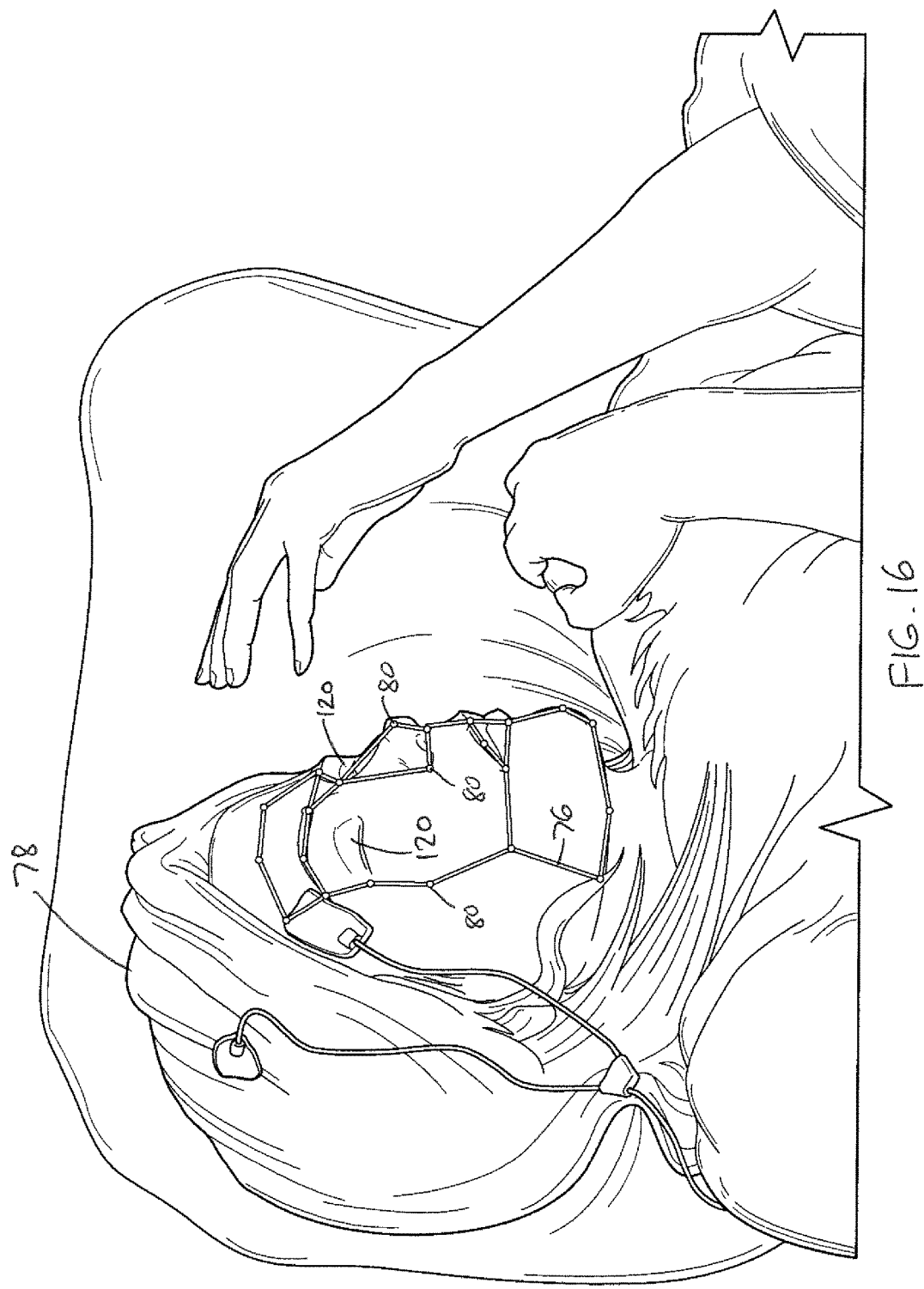
FIG. 16 is a perspective view of a patient asleep, images of which are captured and analyzed by the video monitoring systems disclosed herein.
Figure 18:
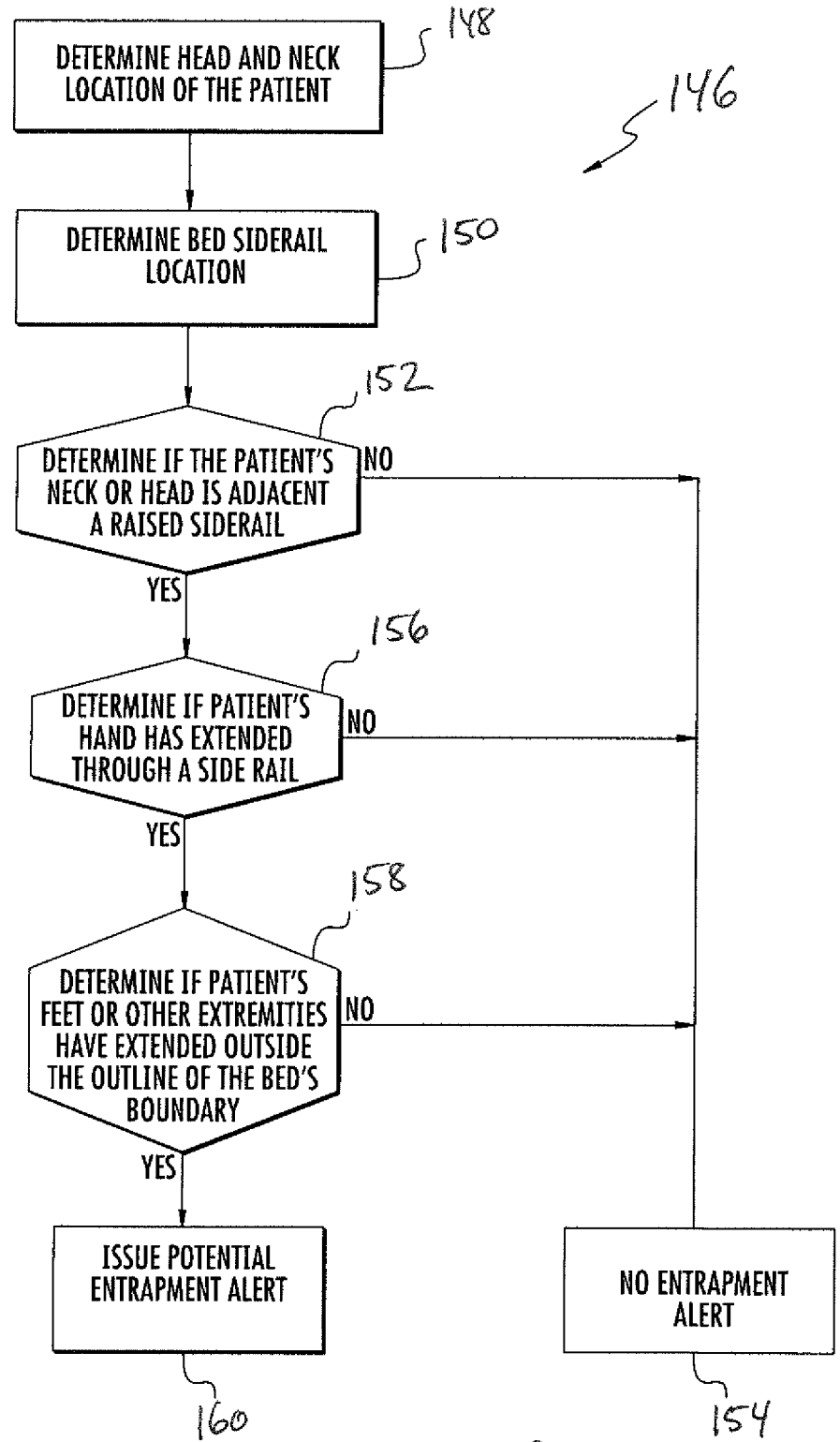
FIG. 18 is a diagram of one example of a patient entrapment algorithm usable by the video monitoring systems disclosed herein.

In at least one embodiment of system 20, computer device 24 executes a patient activity software module 34 that determines if a patient is entrapped in patient support apparatus 36. FIG. 15 illustrates an example of patient entrapment, and FIG. 18 illustrates one example of a patient entrapment detection algorithm 126 that is executed by computer device 24. Patient entrapment algorithm 146 determines if an alert should be issued indicating that a patient may have become entrapped between a siderail of the bed and the mattress or other surface of the bed.

Algorithm 146 (FIG. 18) starts at step 148, in which system 20—either via computer device 24 or another computing device—determines the head and neck locations of the patient from the skeletal data generated from cameras 22. At step 150, computer device 24 determines the location of the siderails and whether the siderails are in the up or down position. If they are in the down position, then no entrapment alert will be issued. If they are in the up position, then computer device 24 proceeds to step 152. At step 152, computer device 24 determines if the patient's head or neck is adjacent to one of the up siderails. If not, computer device 24 moves to step 154 and does not issue any potential entrapment alert. If so, then computer device 24 moves to step 156 where it determines if the patient's hand or fingers have extended through the siderail. If so, control proceeds to step 158. If not, control moves to step 154 and no alert is issued. At step 158, computer device 24 determines if any other extremity of the patient has moved beyond the boundaries of the bed. If so, then a potential entrapment alert is issued at step 160. If not, no alert is issued.

It will be understood by those skilled in the art that algorithm 146 may be modified in many ways for determining if an entrapment alert should or should not be issued. As one example, an alert may be issued if fewer than all of the conditions determined in steps 152, 156, and 158 are present. Alternatively, still other conditions may be factored into the algorithm, or substituted for the steps illustrated in FIG. 18.

3. Equipment Monitoring

In at least one embodiment of system 20, computer device 24 executes a patient support apparatus software module 34 that effectively converts "dumb" patient support apparatuses into "smart" patient support apparatuses. More specifically, such a patient support apparatus software module 34 detects a number of parameters regarding one or more patient support apparatuses 36 that could otherwise be detected by sensors on-board the patient support apparatus 36. Such software modules 34 therefore enable the healthcare facility to purchase less costly patient support apparatuses 36 that do not have sensors for detecting these parameters, yet still receive the benefits from such sensors by allowing system 20 to detect the desired parameters.

In one embodiment of such a patient support apparatus software module 34, computer device 24 analyzes the outputs of cameras 22 to determine any one or more of the following parameters associated with a patient support apparatus 36, such as, but not limited to, a bed: detecting when a patient exits the bed, detecting a height of the bed, detecting an angle of the Fowler section of the bed, detecting the position of each siderail (up, down, intermediate, etc.), detecting if a cord is plugged in (power cord, nurse call cord, data cord, etc.), detecting an obstruction to movement of any component of the bed, detecting when the bed is empty to permit automatic zeroing of a scale built into the bed, and counting movement of the components of the bed for maintenance purposes.

When configured with a patient support apparatus software module 34, system 20 communicates all or a portion of the data it generates to the patient support apparatus 36, such as via patient support apparatus computer device 70. When the patient support apparatus 36 receives this data, it makes it available for display locally on one or more lights, indicators, screens, or other displays on patient support apparatus 36. For example, when system 20 is currently executing an exit detection algorithm for a particular patient support apparatus 36, computer device 24 forwards this information to the patient support apparatus 36 so that a caregiver receives a visual confirmation that exit detection alerting is active for that bed, chair, or other patient support apparatus 36. As another example, computer device 24 sends the Fowler angle measured by system 20 to the patient support apparatus 36 so that it can be displayed and/or used by the patient support apparatus. System 20 further sends a signal to patient support apparatus 36 indicating when the patient has left the bed 36 so that the bed 36 can perform an auto-zeroing function of its built-in scale system. Any of the other parameters that are detected—e.g. an obstacle, the positions of the siderails, the height of the bed's deck, and a running total of the number of times various components on the bed have been moved, whether a cord is plugged in prior to the bed moving (and thus triggering a warning to the caregiver)—are sent by computer device 24 to the patient support apparatus 36, in at least one embodiment of system 20 in which computer device 24 executes a patient support apparatus software module.

4. Asset Tracking

In at least one embodiment of system 20, computer device 24 executes an asset tracking software module 34 that monitors the location of assets within a healthcare facility. Such a software module performs any one or more of the following functions: monitors the location of equipment throughout the healthcare facility; monitors which rooms are available (i.e. no patient and room/bed is clean); monitors the possessions of patients to help ensure that all possessions are retrieved prior to discharge; monitors what supplies and/or equipment are used with a patient so that proper billing can be applied; and monitors the inventory level of supplies so that notification can be provided to the appropriate personnel within the healthcare facility to order more supplies.

Such asset tracking functions are carried out in any of the object-detection manners discussed above. For example, in some embodiments, database 50 contains attribute data 44 and other data regarding one or more of the assets that are to be monitored and uses this data to detect and monitor these assets. This technique is used, in at least one embodiment, to track the location of equipment throughout the facility, monitor what supplies and/or equipment are used with a patient, and monitor the inventory level of supplies.

The determination of which rooms are available is carried out, in at least one asset tracking software module 34, by detecting not only the absence of a patient from a room for a particular time period, but the removal of most—if not all—of his or her possessions. The determination of what objects belong to a patient is carried out by monitoring the patient's entry into the room and the items that are brought into the room that accompany the patient. Special areas of the room, e.g. closets or drawers, may also be assigned for personal use by patients and system 20 is configured to monitor what objects are placed in these areas and detect when they are emptied.

The determination of whether a room has been cleaned or not is carried out in at least one asset tracking software module 34 by detecting the presence of designated cleaning personnel in the room after the departure of the patient. In some embodiments, system 20 not only monitors the presence of the designated cleaning personnel, but also monitors the steps taken by the cleaning personnel to clean the room. For example, in some embodiments, system 20 monitors whether or not the cleaning personnel follow one or more room-cleaning protocols that are defined by system 20, and which can be custom-tailored by authorized administrators of the healthcare facility. Only if these cleaning protocols are followed does system 20 determine that the room is clean, and thus available for new patients.

5. Patient Visitation Metrics

In at least one embodiment of system 20, computer device 24 executes a patient visitation metrics software module 34 that monitors a number of different metrics during the patient's visit and makes these metrics available to patient in the form of an end-of-stay report for the patient and/or the patient's family. Such a report includes any one or more of the following: the number of times that a nurse, doctors, or other staff member visited the patient during his/her stay; a graph, or other measurement, showing the patient's vital signs, pain levels, medications, and input/output (food/drink) during the patient's stay; the number of times the room was cleaned; the noise level of the room during the patient's stay; and a breakdown of the patient's stay into various categories and time frames, such as, but not limited to: testing, diagnosis, treatment, and recovery.

In some embodiments, computer device 24 generates this end-of-stay report directly by sending the report information to a printer. In other embodiments, computer device 24 forwards the report information to another system on the healthcare facility network 30, or to another system located at a remote location (e.g. one or more remote computer devices 40; FIG. 2) that uses the data to generate a report. In some situations, the report is generated based upon information received from other systems as well, such as the EMR computer device 60, an accounting/billing system, and/or still other systems.

6. Video and Non-Video Data Integration

In at least one embodiment of system 20, computer device 24 executes a sensor integration software module 34 that integrates sensor data, such as from one or more sensors 58, with the image and depth data gathered from cameras 22. Such a sensor integration software module 34 ties together the readings from the other sensors 58 with the activity and/or condition of the patient so that more useful information about the sensor readings and/or data from cameras 22 is obtained. In one embodiment, the sensor integration software module 34 ties together one or more of the following sensor outputs with the data from cameras 22: the patient's heart rate, blood pressure, respiratory rate, body temperature, and/or pulse oximetry readings; a center of gravity of the patient on patient support apparatus 36; a pressure map of the patient's interface pressures; an incontinence sensor; a glucose monitor; a sleep quality monitor; an electrocardiogram (ECG); an intracranial pressure reading; a microphone; and/or one or more thermal cameras.

When executing a sensor integration software module 34, computer device 24 records in the collected data 56 the readings from sensors 58 and ties together the sensor 58 readings with the events and data gathered from cameras 22. Thus, for example, when a patient exits a bed, rolls over, takes a medication, eats, sleeps, and/or engages in other activities, not only are these activities noted and recorded in the collected data 56 of database 50, but the readings made by the sensors 58 during those events is also recorded in collected data 56. The records are indexed, in at least one embodiment, based upon both the sensor 58 data and the camera 22 data. Thus, later searching of the camera 22 data for one or more events will also bring up the corresponding sensor 58 data, and later searching of the sensor 58 data will also bring up the corresponding events/activities that were detected from the camera 22 data.

The sensor integration software module 34 provides a number of advantages. First, in one embodiment, such a software module 34 filters alarms from multiple individual devices into a unified alarming system. Second, such a software module 34 provides a more complete picture of the room and the patient. Thus, for example, if the patient's heart rate, blood pressure, respiratory rate, or other vital signs increase significantly, but this is accompanied by the patient exiting the patient support apparatus 36, this may not be as clinically significant as if the heart rate, blood pressure, and/or respiratory rate were to rise in a comparable manner while the patient remained on patient support apparatus 36. The integration of the data from camera 22 with the data from the sensors therefore gives the caregivers a more complete picture of what is going on and can result in reductions in alarm fatigue by the healthcare staff and better patient care.

The integration of data from cameras 22 and data from sensors 58 by system 20 also enables the collected data 56 to be used for more robust and/or predictable algorithms to be generated for future use. Thus, for example, by combining a patient's vital sign readings with data from cameras 22, more accurate exit detection algorithm can be derived from analyses of the collected data 56. As another example, by utilizing readings from an incontinence sensor, the likelihood of an impending exit by the patient from patient support apparatus 36 can also be more accurately predicted when an incontinence event is detected.

7. Gesture Controls

System 20 is also adapted to be equipped with a gesture software module 34 that records and analyzes hand or arm gestures to signal a command for the caregiver and/or to control a device in the room. For example, raising a hand for more than five seconds may initiate a nurse call. Alternatively, a caregiver raising or lowering his or her arms will, in some embodiments, causes the patient support apparatus 36 to raise or lower its height, respectively. When such a gestures software module 34 is included with system 20, the control of the patient support apparatus 36 by gestures is accomplished by computer device 24, which first interprets the gesture and then sends the corresponding command to patient support apparatus computer device 70, which in turn forwards the command to the corresponding patient support apparatus 36.

At least one embodiment of a gesture software module 34 also utilizes a projected user interface image that is projected onto a nearby surface from projector 32. The user interface image may comprise projected images of buttons, or other user interface controls. Cameras 22 detect hand motions that substantially simulate button pressing of the control images of the user interface images, and computer device 24 controls the motions of the patient support apparatus 36 or other devices in response to these virtual or simulated button pressings. In other words, one or more projectors 32 project light images of a user interface onto a selected surface and when the patient moves his or her arms, fingers, or legs in a predefined manner relative to those images, such actions are interpreted as the patient desiring a certain outcome. Further details of such virtual control panels are disclosed in commonly assigned U.S. patent application Ser. No. 14/549,006 filed Nov. 20, 2014 by inventors Richard A. Derenne et al. and entitled PERSON SUPPORT APPARATUS WITH VIRTUAL CONTROL PANELS, the complete disclosure of which is hereby incorporated herein by reference.

System 20 is also adapted to be equipped with another gesture software module 34 that records and translate sign language so that communication between a person who understands sign language and a person who does not can be effectuated. In one such embodiment, computer device 24 detects and translates sign language gestures and converts them to an audio stream that is forwarded to the vicinity of the patient and/or caregiver (e.g. to patient support apparatus 36, or to one or more speakers positioned within the room 28). The gesture software module 34 can also be configured to convert voices that are spoken into a nearby speaker to sign language. When so configured, computer device 24 forwards images of a person making the corresponding signs to the person who understands sign language. Such translation of sign language into voice data, or vice versa, can be carried out using any commercially available software packages that are incorporated into the software module 34.

8. Other Conditions

System 20 may also be used to detect multiple other conditions besides any of those previously mentioned. As one example, system 20 may be used for providing code pink alerts in nurseries, or other areas of a patient care facility where newborns are present. In such cases, cameras 22 are positioned at areas outside of patient rooms. Specifically, cameras 22 are placed at areas where they are able to detect any movement of a baby outside of a pre-designated acceptable area for the baby. That is, cameras 22 are positioned so that they can detect any movement of a child that is not authorized without the permission of a caregiver, staff member, or other authorized employee, or any movement of a child outside of a predefined area that occurs in the presence of a non-parent or non-authorized employee. In such situations, system 20 is configured to identify individuals through face recognition or other means. System 20 may further be configured to identify infants. The coordinates of the infant are determined from the frames recorded by one or more cameras 22. The horizontal component or components of this position may are then compared with the predefined threshold areas. In one embodiment, if the child moves beyond these thresholds, an alert is issued, regardless of what other adults might be accompanying the child. In another embodiment, if the child moves beyond a threshold, an alert may is issued only if the child is not accompanied by either its parent or an authorized employee of the hospital. In still other embodiments, a mixture of both types of alerting is present for different thresholds within the hospital, or other type of patient care facility.

In at least one other embodiment, system 20 is partially or wholly integrated with the system disclosed in commonly assigned U.S. patent application 62/081,744 filed Nov. 19, 2014 by inventors Daniel V. Brosnan et al. and entitled MEDICAL APPARATUS WITH SELECTIVELY ENABLED FEATURES, the complete disclosure of which is hereby incorporated herein by reference. When so integrated, system 20 utilizes the image and depth data from cameras 22 to identify, tag, and log in the collected data 56 any of the events, activities, and/or data regarding one or more of the transactions described in the '744 patent application that occur at or in the vicinity of the patient support apparatus 36.

System 20 is also configurable in some embodiments to execute a quality auditing software module 34 that analyzes the quality of care provided to a patient according to a number of different metrics. In some embodiments, authorized personnel at the healthcare institution can custom tailor these metrics to the particular needs of that healthcare institution. In general, such metrics include how well any or all of the healthcare protocols were followed (as detected by system 20), how fast caregivers responded to inquiries or requests, how much time caregivers spent at the patient's bedside, and how many staff were utilized in the care of the patient (including the amount of time for each. Still further, the quality auditing software module 34 can be configured to monitor any number of the items that are part of the Hospital Consumer Assessment of Healthcare Providers and Systems (HCAHPS) survey that is often administered to selected patients at healthcare facilities. The HCAHPS survey was developed by the U.S. Centers for Medicare and Medicaid Services in conjunction with the Agency for Healthcare Research and Quality (AHRQ) and includes a number of questions that are asked of a randomly selected set of patients after their discharge from a hospital or other healthcare facility.

System 20 is also configurable in some embodiments to execute a sleep quality software module 34 that monitors and assesses the quality of a patient's sleep. Computer device 24 assesses the patient's sleep quality by monitoring the how long the patient sleeps for, the number of interruptions, the amount of movement of the patient during sleep, and an analysis of the patient's vital signs and/or other sensor data gathered from sensors 58 while the patient sleeps. In at least one embodiment, computer device 24 operates in conjunction with, or utilizes, any of the sleep quality measuring steps and/or algorithms disclosed in commonly assigned PCT patent application PCT/US2014/026030 filed Mar. 13, 2014 by applicant Stryker Corporation and entitled PATIENT SUPPORT APPARATUS WITH PATIENT INFORMATION SENSORS, the complete disclosure of which is hereby incorporated herein by reference.

System 20 is also configurable in some embodiments to execute a caregiver presence software module 34 that monitors the presence of a healthcare worker within the patient's room and changes one or more conditions automatically based upon the workers presence. Some of those conditions are automatically further changed when the worker exits the room. One such software module automatically silences, or reduces the volume of, one or more alerts that are being triggered by any of the patient support apparatuses 36, or by system 20 itself, when a caregiver enters the room. Another such software module automatically changes a user interface on patient support apparatus 36 in response to the caregiver's presence (e.g. by unlocking certain functions that are not accessible to the patient). Still further, in some embodiments, the software module 34 automatically changes what information is displayed on the patient support apparatus 36, or another display in the room, based upon the type of worker enters the room (e.g. technician, cleaning personnel, caregiver, administrator, volunteer, etc.).

It will be understood by those skilled in the art that system 20 may be varied from the embodiments described above and that system 20 may be configured to monitor any one or more of the conditions described above. More specifically, system 20 can be equipped with any combination of one or software modules 34 for carrying out any of the functions described herein. Indeed, in some embodiments, system 20 does not include any software modules 34 that are separable from the general functions carried out by system 20. Further, in some embodiments, the general functions carried out by system 20 are modified from those described herein.

Various alterations and changes can be made to the above-described embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A monitoring system for a patient support apparatus comprising:
   a person support apparatus having an aural alert;
   a camera adapted to capture images of the patient support apparatus and output image data representative of the images;
   a database containing patient care protocol data, the patient care protocol data defining a task to be performed by a caregiver assigned to a patient of the patient support apparatus; and
   a computer device in communication with the camera, the patient support apparatus, and the database, the computer device adapted to analyze the image data to detect a presence of the caregiver in a vicinity of the patient support apparatus and to determine if the task has been performed by the caregiver, and, if not, to send a reminder to the caregiver to perform the task, the computer device further adapted to send a message to the patient support apparatus instructing the patient support apparatus to reduce a volume of the aural alert when the computer device detects the presence of the caregiver in the vicinity of the patient support apparatus.

2. The monitoring system of claim 1 further including a user interface in communication with the database, the user interface adapted to allow an authorized user to enter information into the database defining the task.

3. The monitoring system of claim 1 wherein the patient care protocol data includes a plurality of tasks to be performed by the caregiver, and wherein the computer device analyzes the image data to determine if each of the plurality of tasks has been performed.

4. The monitoring system of claim 3 wherein the computer device is adapted to transmit an alert message to the patient support apparatus instructing the patient support apparatus to issue the aural alert if at least one of the tasks is not completed.

5. The monitoring system of claim 1 furthering including a depth sensor in communication with the computer device, the depth sensor adapted to emit infrared light toward the patient support apparatus and detect reflections of the infrared light.

6. The monitoring system of claim 1 wherein the computer device is further adapted to identify a location of the patient's head in the image data and automatically blur that location in the image data.

7. The monitoring system of claim 1 wherein the task includes at least one of the following: performing a fall risk assessment of the patient; turning the patient; changing a dressing on a wound of the patient; performing therapy on the patient; visiting the patient; taking a vital sign measurement of the patient; administering medication to the patient; starting or stopping an IV of the patient; starting or stopping a compression device used to treat the patient; adjusting an angle of a head section of the patient support apparatus; and starting or stopping a ventilator used on the patient.

8. The monitoring system of claim 7 wherein, if the computer device determines that the task has been performed, the computer device is further adapted to communicate information to an electronic medical record indicating that the task has been performed.

9. The monitoring system of claim 1 wherein the task is activating an exit detection system associated with the patient support apparatus.

10. The monitoring system of claim 9 wherein the database includes a fall risk assessment associated with the patient of the patient support apparatus, and the computer device is adapted to automatically activate the exit detection system after the caregiver leaves the vicinity of the patient support apparatus if the fall risk assessment indicates that the patient is a fall risk.

11. The monitoring system of claim 9 wherein the database is adapted to include a fall risk assessment associated with the patient of the patient support apparatus, and the computer device is adapted to automatically activate the exit detection system after the caregiver leaves the vicinity of the patient support apparatus if the fall risk assessment is not present in the database.

12. The monitoring system of claim 1 wherein the reminder is transmitted to the patient support apparatus for display on a display of the patient support apparatus.

13. The monitoring system of claim 12 wherein the computer device sends the reminder to the caregiver after the computer device detects the presence of the caregiver within the vicinity of the patient support apparatus.

14. A monitoring system for a patient support apparatus comprising:
a person support apparatus having an aural alert;
a camera adapted to capture images of [a] the patient support apparatus and output image data representative of the images, the patient support apparatus including a head section adapted to pivot about a generally horizontal pivot axis;
a database containing patient care protocol data, the patient care protocol data defining an angular condition of the head section of the patient support apparatus to be met by a caregiver assigned to a patient of the patient support apparatus; and
a computer device in communication with the camera, the patient support apparatus, and the database, the computer device adapted to analyze the image data to detect a presence of the caregiver in a vicinity of the patient support apparatus, to determine if the head section of the patient support apparatus meets the angular condition defined in the patient care protocol data, to determine if the patient is slouching in the patient support apparatus, to issue an alert activation message to the patient support apparatus if the patient is slouching or the head section of the patient support apparatus does not meet the angular condition, and to issue an alert silence message to the patient support apparatus instructing the patient support apparatus to reduce a volume of the aural alert when the computer device detects the presence of the caregiver in the vicinity of the patient support apparatus.

15. The monitoring system of claim 14 wherein the computer device is further adapted to identify a location of the patient's head in the image data and automatically blur that location in the image data.

16. The monitoring system of claim 15 wherein the computer device is further adapted to store the image data with the blurred location and to not store any of the image data without the blurred location.

17. The monitoring system of claim 14 wherein the angular condition of the head section of the patient support apparatus defined in the patient care protocol data is selected to help prevent ventilator associated pneumonia.

18. The monitoring system of claim 14 wherein the patient care protocol data also defines a task to be performed by the caregiver and the computer device analyzes the image data to determine if the task has been performed by the caregiver.

19. The monitoring system of claim 18 wherein the task is activating an exit detection system associated with the patient support apparatus, and the computer device is further adapted to automatically send a message to the patient support apparatus to activate the exit detection system if the caregiver leaves the vicinity of the patient support apparatus without activating the exit detection system.

* * * * *